United States Patent
Peng et al.

(10) Patent No.: US 11,104,664 B2
(45) Date of Patent: Aug. 31, 2021

(54) 4,5,6-TRISUBSTITUTED INDAZOLE DERIVATIVES, AND PREPARATION METHOD AND PHARMACEUTICAL USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Jianbiao Peng, Shanghai (CN); Yang Liu, Shanghai (CN); Lixiao Wang, Shanghai (CN); Zhihua Fang, Shanghai (CN); Zonglei Fei, Shanghai (CN); Xi Chen, Shanghai (CN); Jiong Lan, Shanghai (CN)

(73) Assignees: SHANGHAI HAIYAN PHARMACEUTICAL TECHNOLOGY CO., LTD.; YANGTZE RIVER PHARMACEUTICAL GROUP CO., LTD.

( * ) Notice: Subject to any disclaimer, the term of this patent is extended or adjusted under 35 U.S.C. 154(b) by 305 days.

(21) Appl. No.: 16/305,369

(22) PCT Filed: Nov. 10, 2017

(86) PCT No.: PCT/CN2017/110465
§ 371 (c)(1),
(2) Date: Nov. 28, 2018

(87) PCT Pub. No.: WO2018/086592
PCT Pub. Date: May 17, 2018

(65) Prior Publication Data
US 2020/0262812 A1   Aug. 20, 2020

(30) Foreign Application Priority Data
Nov. 11, 2016   (CN) .......................... 201610994394.6

(51) Int. Cl.
*C07D 401/12* (2006.01)
*C07D 401/14* (2006.01)
*C07D 405/14* (2006.01)
*C07D 413/14* (2006.01)

(52) U.S. Cl.
CPC ......... *C07D 401/14* (2013.01); *C07D 401/12* (2013.01); *C07D 405/14* (2013.01); *C07D 413/14* (2013.01)

(58) Field of Classification Search
CPC ... C07D 401/12; C07D 401/14; C07D 405/14
See application file for complete search history.

(56) References Cited

FOREIGN PATENT DOCUMENTS

| CN | 104540500 A | 3/2013 |
|---|---|---|
| CN | 104968646 A | 10/2015 |
| WO | 2011/140325 A1 | 11/2011 |
| WO | 2012/118812 A2 | 9/2012 |
| WO | 2015/104677 A1 | 7/2015 |
| WO | 2015/110999 A1 | 7/2015 |

OTHER PUBLICATIONS

International Search Report for PCT/CN2017/1140465, dated Jan. 31, 2018, 3 pages.
Yang et al., "Structure-Activity Relationship Studies for Enhancer of Zeste Homologue 2 (EZH2) and Enhancer of Zeste Homologue 1 (EZH1) Inhibitors", J. Med. Chem. 2016, 59, 7617-7633.
Office Action for CN 201780008603.8, dated Aug. 12, 2020, with English translation, 14 pages.
Search report for CN Application No. 2017800086038, dated Jul. 27, 2018, 2 pages.

*Primary Examiner* — Laura L Stockton
(74) *Attorney, Agent, or Firm* — Adsero IP

(57) ABSTRACT

Provided are 4,5,6-tri-substituted indazoles derivatives, a preparation method therefor, and a use thereof in medicines. Specifically, provided are compounds of formula (I) or pharmaceutically acceptable salts, stereoisomers, solvates, or prodrugs thereof, a preparation method therefor, and a use thereof.

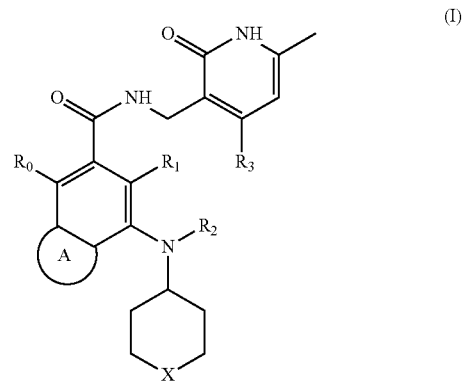

14 Claims, No Drawings

4,5,6-TRISUBSTITUTED INDAZOLE DERIVATIVES, AND PREPARATION METHOD AND PHARMACEUTICAL USE THEREOF

CROSS-REFERENCE TO RELATED APPLICATION

This application claims priority to and is a 35 U.S.C. § 371 national phase application of PCT/CN2017/110465 (WO 2018/086592 A1), filed on Nov. 10, 2017 entitled "4, 5, 6-TRI-SUBSTITUTED INDAZOLES DERIVATIVES, PREPARATION THEREOF AND USE THEREOF IN MEDICINES", which application claims priority to and the benefit of Chinese Application CN 201610994394.6 filed Nov. 11, 2016.

TECHNICAL FIELD

The present disclosure belongs to the field of medical technology. In particular, the present disclosure particularly relates to a 4,5,6-trisubstituted indazole derivative, its preparation method and use as an EZH2 inhibitor, and pharmaceutical compositions prepared therefrom.

BACKGROUND

The histone-lysine-N-methyltransferase EZH2 is involved in DNA methylation and, ultimately, transcription repression; EZH2 catalyzes and transfers a methyl group to histone H3 at lysine 27 by a cofactor S-adenosyl-L-methionine. This methylation promotes the formation of heterochromatin, and therefore triggers gene silencing.

EZH2 is a functional enzymatic part of PRC2, which controls and regulates development and differentiation through epigenetic maintenance of genes, thus ensuring healthy embryonic development. The mutation or overexpression of EZH2 is associated with the formation of many cancers. The EZH2 controls genes for controlling tumor development, the inhibition of EZH2 activity will slow the growth of the tumor. As a target inhibitor, EZH2 can regulate a variety of cancers including breast cancer, prostate cancer, melanoma and bladder cancer.

PCT applications WO2011140324A1 and WO2012075080A1 disclose indole compounds as EZH2 inhibitors for the treatment of cancer. The PCT application WO2012118812A2 discloses bicyclic heterocyclic compounds as EZH2 inhibitors for the treatment of cancer.

Therefore, the inhibition of EZH2 activity will effectively reduce cell proliferation and invasion, thereby providing a beneficial treatment for EZH2-mediated diseases or conditions. The compounds of the present disclosure provide solutions for the treatment of diseases or EZH2-mediated tumor as EZH2 inhibitors.

SUMMARY

An object of the present disclosure is to provide a structurally novel compound which can act as EZH2 inhibitors.

According to a first aspect of the present disclosure, a compound of formula (I), or a pharmaceutically acceptable salt, solvate, stereoisomer or prodrug thereof is provided:

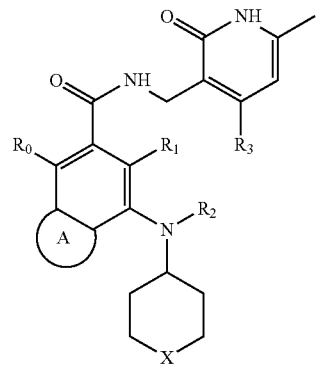

wherein, $R_0$ is hydrogen;

$R_1$ is CN, halogen (preferably fluorine, chlorine, bromine), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) or $C_{3-8}$ cycloalkoxy (preferably $C_{3-6}$ cycloalkoxy);

$R_2$ is hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl) or $C_{3-8}$ cycloalkyl (preferably $C_{3-6}$ cycloalkyl);

$R_3$ is hydrogen, halogen (preferably fluorine, chlorine, bromine), hydroxy, CN, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), $C_{1-8}$ alkoxy (preferably $C_{1-6}$ alkoxy, more preferably $C_{1-3}$ alkoxy), halogenated $C_{1-8}$ alkoxy (preferably halogenated $C_{1-6}$ alkoxy, more preferably halogenated $C_{1-3}$ alkoxy), $C_{3-8}$ cycloalkoxy (preferably $C_{3-6}$ cycloalkoxy), $C_{6-10}$ aryl(preferably phenyl), —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —CONR$_a$R$_b$ or NR$_a$R$_b$;

X is NR$_4$, CR$_5$R$_6$, O, S or S(O)$_2$;

$R_4$ is hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), C(O)$C_{1-8}$ alkyl (preferably C(O)$C_{1-6}$ alkyl, more preferably C(O)$C_{1-3}$ alkyl), C(O)O$C_{1-8}$ alkyl (preferably C(O)O$C_{1-6}$ alkyl, more preferably C(O)O$C_{1-3}$ alkyl), CONR$_{a1}$R$_{b1}$, $C_{3-8}$ cycloalkyl (preferably $C_{3-6}$ cycloalkyl), —SO$_2$$C_{1-10}$ alkyl (preferably —SO$_2$$C_{1-6}$ alkyl, more preferably —SO$_2$$C_{1-3}$ alkyl), —C(O)CH$_2$CN, —C(O)CH$_2$OH, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle;

$R_5$, $R_6$ are each independently hydrogen, halogen, hydroxy, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), NR$_{a2}$R$_{b2}$, 4 to 6 membered saturated heterocycle heteromonocycle, 5 to 6 membered monocylic heteroaryl ring, spiro, spiroheterocycle, bridged ring or bridged heterocycle;

$R_a$, $R_b$, $R_{a1}$, $R_{b1}$, $R_{a2}$, $R_{b2}$ are each independently hydrogen, $C_{1-8}$ alkyl (preferably $C_{1-6}$ alkyl, more preferably $C_{1-3}$ alkyl), or $C(O)C_{1-8}$ alkyl (preferably $C(O)C_{1-6}$ alkyl, more preferably $C(O)C_{1-3}$ alkyl);

ring A is a structure represented by formula (A-1), formula (A-2), formula (A-3) or formula (A-4):

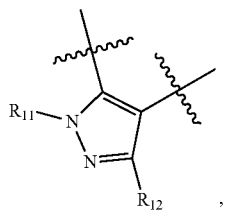
(A-1)

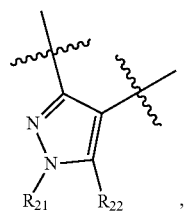
(A-2)

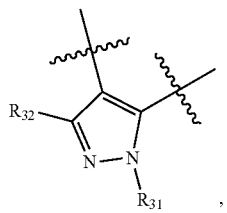
(A-3)

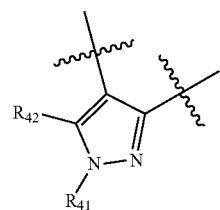
(A-4)

wherein, $R_{11}$, $R_{21}$, $R_{31}$, $R_{41}$ are each independently hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), 4 to 6 membered saturated heteromonocycle, 5 to 6 membered monocylic heteroaryl ring, spiro, spiroheterocycle, bridged ring or bridged heterocycle;

$R_{12}$, $R_{22}$, $R_{32}$, $R_{42}$ are each independently hydrogen, halogen (preferably fluorine, chlorine, bromine), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl) or $C_{3-8}$ cycloalkyl (preferably $C_{3-6}$ cycloalkyl); and the alkyl, alkoxy, cycloalkyl, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle are unsubstituted or substituted by 1, 2 or 3 substituents selected from the group consisting of CN, acetyl, hydroxy, hydroxymethyl, hydroxyethyl, carboxyl, —C(O)OC$_{1-6}$ alkyl, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), $NR_{a3}R_{b3}$, 4 to 6 membered saturated heteromonocycle, 5 to 6 membered monocylic heteroaryl ring, 8 to 10 membered bicyclic heteroaryl ring, spiro, spiroheterocycle, bridged ring and bridged heterocycle; wherein $R_a3$, $R_{b3}$ are each independently hydrogen, $C_{1-8}$ alkyl (preferably $C_{1-6}$ alkyl, more preferably $C_{1-3}$ alkyl) or $C_{1-8}$ alkyl substituted by $C_{1-8}$ alkoxy (preferably $C_{1-6}$ alkyl substituted by $C_{1-6}$ alkoxy, more preferably $C_{1-3}$ alkyl substituted by $C_{1-3}$ alkoxy).

In another preferred embodiment, $R_1$ is $C_{1-3}$ alkyl (preferably methyl or ethyl).

In another preferred embodiment, $R_2$ is hydrogen, $C_{1-3}$ alkyl or halogenated $C_{1-3}$ alkyl.

In another preferred embodiment, $R_2$ is $C_{1-3}$ alkyl (preferably methyl or ethyl).

In another preferred embodiment, $R_3$ is hydrogen, halogen, $C_{1-3}$ alkyl or $C_{1-3}$ alkoxy.

In another preferred embodiment, $R_3$ is hydrogen, fluorine, chlorine, methyl, ethyl, n-propyl, isopropyl, methoxy, ethoxy, propoxy, or isopropoxy.

In another preferred embodiment, $R_0$ is hydrogen and $R_1$ is $C_{1-3}$ alkyl (preferably methyl or ethyl).

In another preferred embodiment, $R_{11}$, $R_{21}$, $R_{31}$, $R_{41}$ are each independently hydrogen or —$(CH_2)_n$-$L_1$; wherein $L_1$ is CN, $NR_{a3}R_{b3}$, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), 4 to 6 membered saturated heteromonocycle, 5 to 6 membered monocylic heteroaryl ring, spiro, spiroheterocycle, bridged ring or bridged heterocycle; and n is 0, 1 or 2;

the alkyl, alkoxy, cycloalkyl, 4 to 6 membered saturated heteromonocycle, 5 to 6 membered monocylic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as previously defined.

In another preferred embodiment, n is 0 or 1.

In another preferred embodiment, the 4 to 6 membered saturated heteromonocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyran.

In another preferred embodiment, the 5 to 6 membered monocylic heteroaryl ring is thiophene, N-alkylpyrrole, furan, thiazole, imidazole, oxazole, pyrrole, pyrazol, triazole, tetrazole, isoxazole, oxadiazole, thiadiazole, pyridine, pyridazine, pyrimidine or pyrazine.

In another preferred embodiment, the azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide or tetrahydropyran in the substituents are unsubstituted or substituted by 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)O$C_{1-6}$ alkyl, and $NR_{a3}R_{b3}$; wherein $R_{a3}$, $R_{b3}$ are each independently hydrogen or $C_{1-3}$ alkyl.

In another preferred embodiment, $R_{11}$, $R_{21}$, $R_{31}$, $R_{41}$ are each independently hydrogen, methyl, ethyl, n-propyl, isopropyl, cyclopropyl, monofluoromethyl, difluoromethyl, trifluoromethyl, monofluoroethyl, difluoroethyl, or trifluoroethyl.

In another preferred embodiment, $R_{12}$, $R_{22}$, $R_{32}$, $R_{42}$ are each independently hydrogen, methyl, ethyl, n-propyl, or isopropyl.

In another preferred embodiment, $R_{12}$, $R_{22}$, $R_{32}$, $R_{42}$ are each independently hydrogen.

In another preferred embodiment, $R_4$ is hydrogen or —(CH$_2$)m-$L_2$; wherein $L_2$ is CN, $C_{1-8}$ alkyl (preferably $C_{1-6}$ alkyl, more preferably $C_{1-3}$ alkyl), $NR_{a3}R_{b3}$, $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), C(O)$C_{1-8}$ alkyl (preferably C(O)$C_{1-6}$ alkyl, more preferably C(O)$C_{1-3}$ alkyl), C(O)O$C_{1-8}$ alkyl (preferably C(O)O$C_{1-6}$ alkyl, more preferably C(O)O$C_{1-3}$ alkyl), CONR$_{a1}$R$_{b1}$, $C_{3-8}$ cycloalkyl (preferably $C_{3-6}$ cycloalkyl), —SO$_2$$C_{1-8}$ alkyl (preferably —SO$_2$$C_{1-6}$ alkyl, more preferably —SO$_2$$C_{1-3}$ alkyl), —C(O)CH$_2$CN, —C(O)CH$_2$OH, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle; and m is 0, 1 or 2; the alkyl, alkoxy, cycloalkyl, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as previously defined.

In another preferred embodiment, m is 0 or 1.

In another preferred embodiment, $R_4$ is —(CH$_2$)$_m$-$L_2$; wherein $L_2$ is halogenated $C_{1-8}$ alkyl (preferably halogenated $C_{1-6}$ alkyl, more preferably halogenated $C_{1-3}$ alkyl) or 4 to 6 membered saturated heteromonocycle; and m is 0 or 1.

In another preferred embodiment, $R_4$ is —CH$_2$-$L_2$; wherein $L_2$ is halogenated $C_{1-8}$ alkyl (preferably halogenated $C_{1-6}$ alkyl, more preferably halogenated $C_{1-3}$ alkyl).

In another preferred embodiment, $R_4$ is $L_2$; wherein $L_2$ is 4 to 6 membered saturated heteromonocycle.

In another preferred embodiment, the 4 to 6 membered saturated heteromonocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyran.

In another preferred embodiment, the 5 to 6 membered monocylic heteroaryl ring is thiophene, N-alkylpyrrole, furan, thiazole, imidazole, oxazole, pyrrole, pyrazol, triazole, tetrazole, isoxazole, oxadiazole, thiadiazole, pyridine, pyridazine, pyrimidine or pyrazine.

In another preferred embodiment, the azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide or tetrahydropyran in the substituents are unsubstituted or substituted by 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)O$C_{1-6}$ alkyl, and $NR_{a3}R_{b3}$; wherein $R_{a}$3, $R_{b3}$ are each independently hydrogen or $C_{1-3}$ alkyl.

In another preferred embodiment, $R_4$ is hydrogen, or halogenated $C_{1-3}$ alkyl.

In another preferred embodiment, $R_5$ is hydrogen and $R_6$ is —(CH$_2$)$_p$-$L_3$; $L_3$ is CN, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), $NR_{a3}R_{b3}$, 4 to 6 membered saturated heteromonocycle, 5 to 6 membered monocylic heteroaryl ring, spiro, spiroheterocycle, bridged ring or bridged heterocycle; and p is 0, 1 or 2;

the alkyl, alkoxy, cycloalkyl, 4 to 6 membered saturated heteromonocycle, 5 to 6 membered monocylic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as previously defined.

In another preferred embodiment, p is 0, 1 or 2; $L_3$ is $NR_{a3}R_{b3}$ or 4 to 6 membered saturated heteromonocycle; $R_{a3}$, $R_{b3}$ are each independently hydrogen, $C_{1-3}$ alkyl or $C_{1-3}$ alkyl substituted by $C_{1-3}$ alkoxy; and the alkyl, alkoxy or 4 to 6 membered saturated heteromonocycle are unsubstituted or substituted by one substituent selected from the group consisting of acetyl, hydroxy, hydroxymethyl, hydroxyethyl, carboxyl, —C(O)OCH$_3$, —C(O)OCH$_2$CH$_3$, —C(O)OC(CH$_3$)$_3$, —C(O)OCH(CH$_3$)$_2$, methyl, ethyl, n-propyl, isopropyl, methoxy, ethoxy, propoxy, isopropoxy, monofluoromethyl, difluoromethyl, trifluoromethyl, monofluoroethyl, difluoroethyl, trifluoroethyl, cyclopropyl, cyclobutyl, cyclopentyl, cyclohexyl, N(CH$_3$)$_2$, N(CH$_2$CH$_3$)$_2$, N(CH$_2$CH$_3$)(CH$_3$), azetidine, oxetane, tetrahydrofuran, tetrahydrothiophene, pyrrolidine, piperidine, piperazine, dioxolane, dioxane, morpholine, thiomorpholine, thiomorpholine-1,1-dioxide, and tetrahydropyran.

In another preferred embodiment, the 4 to 6 membered saturated heteromonocycle is azetidine, oxetane, tetrahydrofuran, tetrahydrothiophene, pyrrolidine, piperidine, piperazine, morpholine, thiomorpholine, thiomorpholine-1,1-dioxide or tetrahydropyran.

In another preferred embodiment, the 5 to 6 membered monocylic heteroaryl ring is thiophene, N-alkylpyrrole, furan, thiazole, imidazole, oxazole, pyrrole, pyrazol, triazole, tetrazole, isoxazole, oxadiazole, thiadiazole, pyridine, pyridazine, pyrimidine or pyrazine.

In another preferred embodiment, the azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide or tetrahydropyran in the substituents are unsubstituted or substituted by 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)O$C_{1-6}$ alkyl, and $NR_{a3}R_{b3}$; wherein $R_{a3}$, $R_{b3}$ are each independently hydrogen or $C_{1-3}$ alkyl.
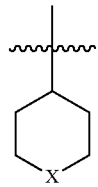
In another preferred embodiment, x is selected from the following group:
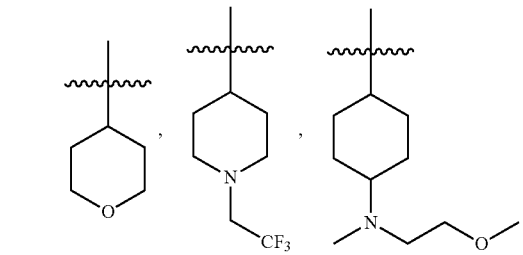
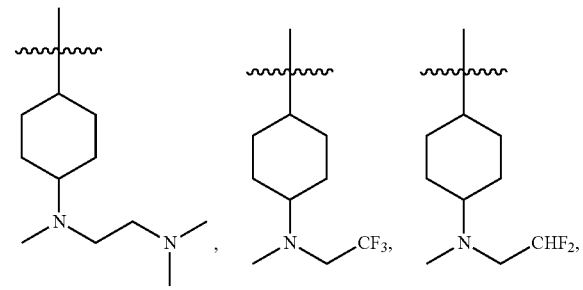
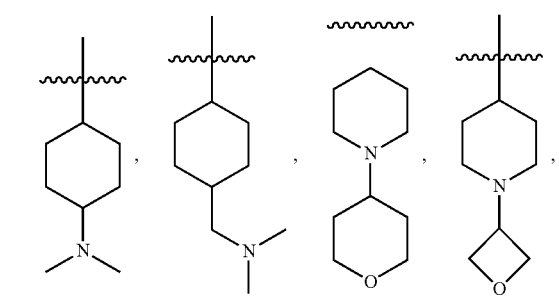
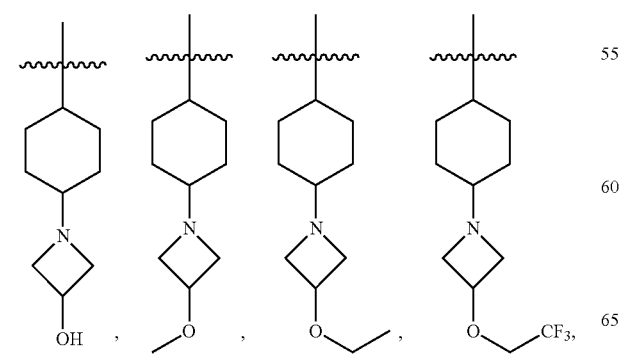
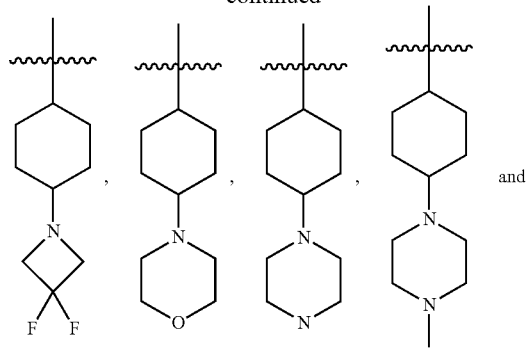 and
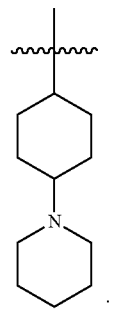
In another preferred embodiment,
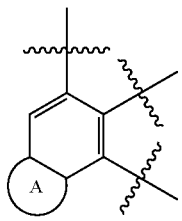
is a structure represented by formula (B-1), formula (B-2) formula (B-3) or formula (B-4):
(B-1)
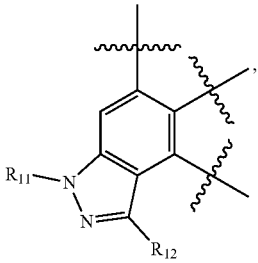
(B-2)
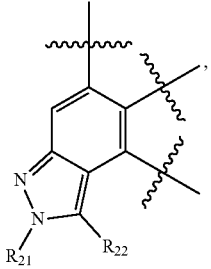

-continued
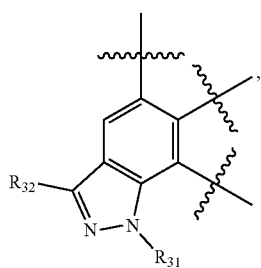
(B-3)
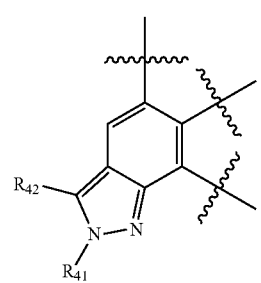
(B-4)
wherein $R_{11}$, $R_{12}$, $R_{21}$, $R_{22}$, $R_{31}$, $R_{32}$, $R_{41}$, $R_{42}$ are as previously defined.
In another preferred embodiment,
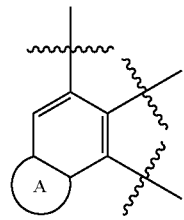
is a structure represented by formula (B-1).
In another preferred embodiment, the compound is selected from Table A below:
TABLE A
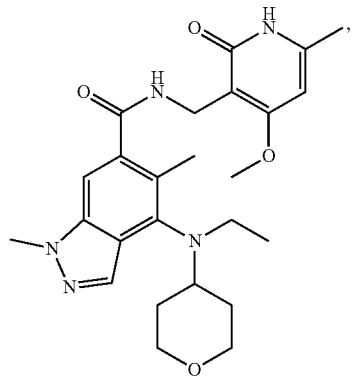
TABLE A-continued
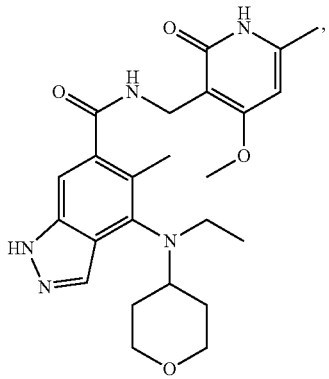 [SMILES: CCN(c1c(C)c(C(=O)NCc2c(OC)cc(C)[nH]c2=O)cc2[nH]ncc12)C1CCOCC1]
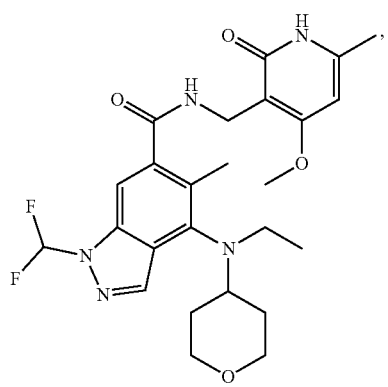 [SMILES: CCN(c1c(C)c(C(=O)NCc2c(OC)cc(C)[nH]c2=O)cc2c1cnn2C(F)F)C1CCOCC1]
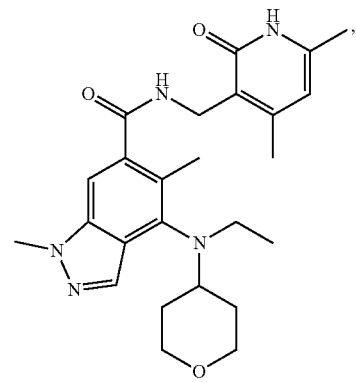
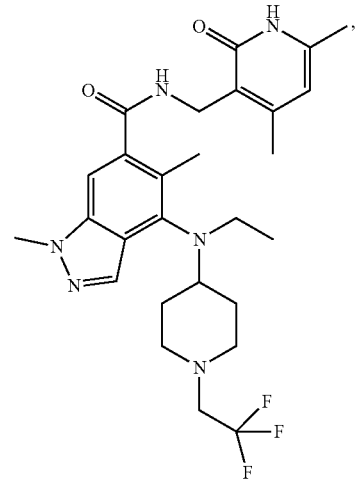

TABLE A-continued
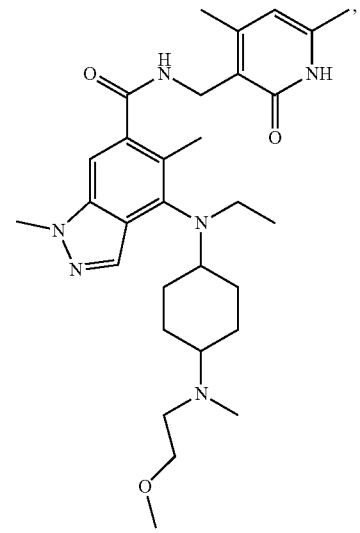
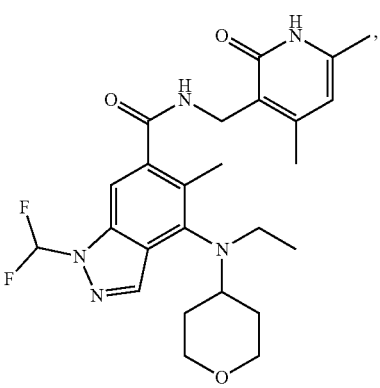 [SMILES: CCN(c1c(C)c(C(=O)NCc2c(C)cc(C)[nH]c2=O)cc2c1cnn2C(F)F)C1CCOCC1]
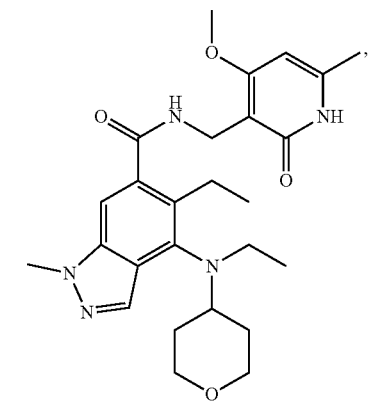
TABLE A-continued
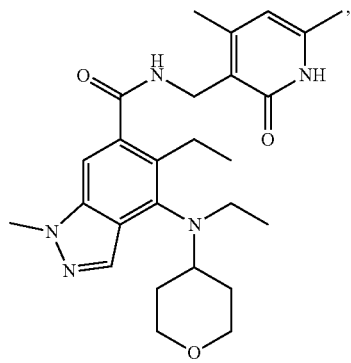
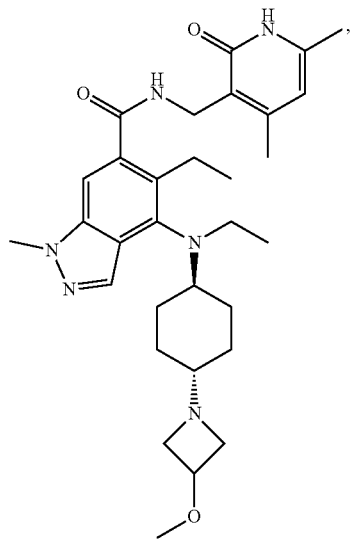
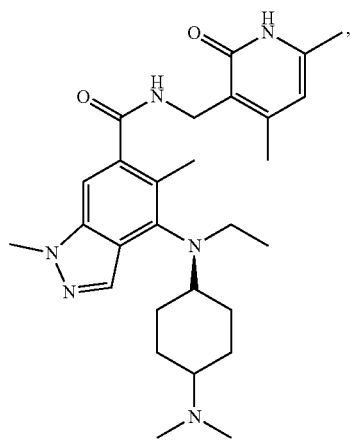

TABLE A-continued
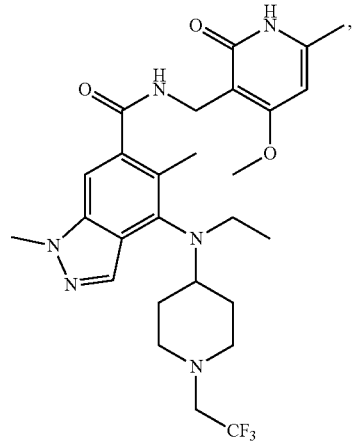
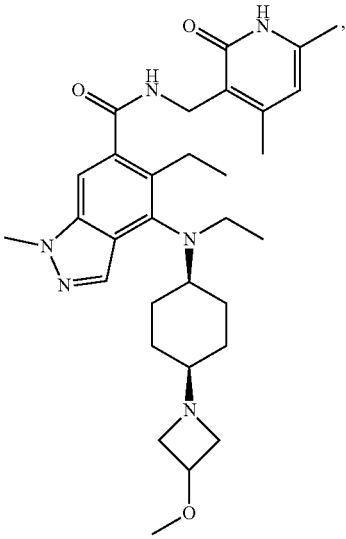

TABLE A-continued
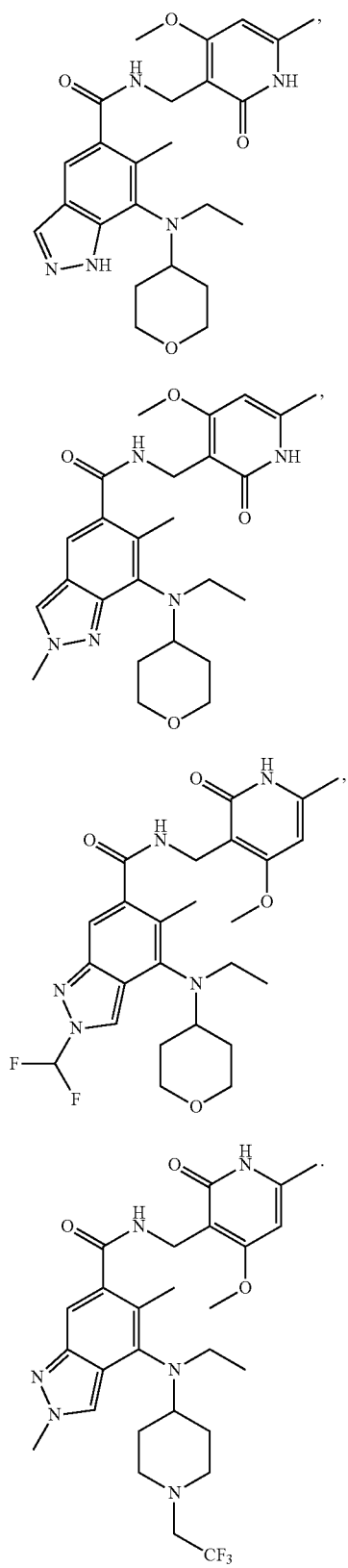
TABLE B
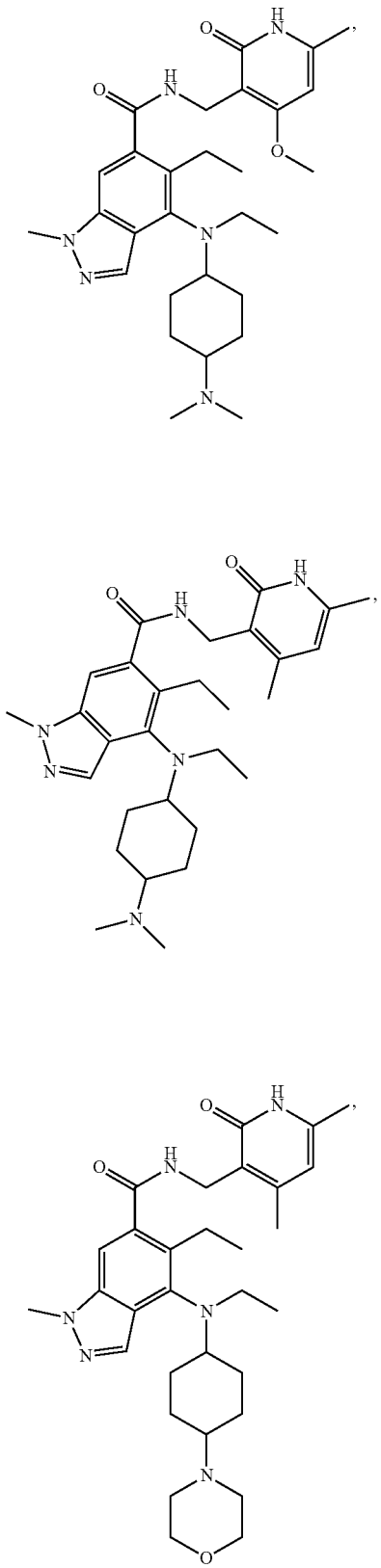
In another preferred embodiment, the compound is selected from Table B below:

TABLE B-continued
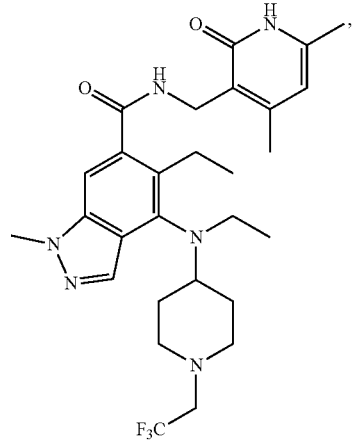
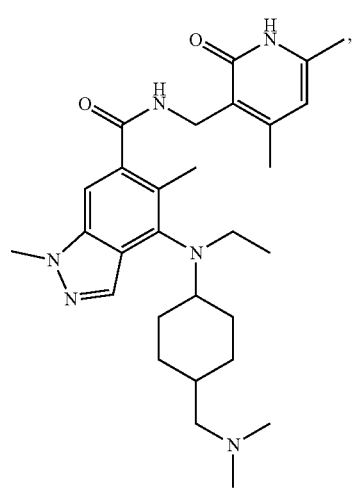
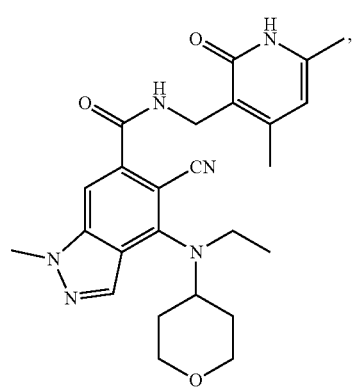
TABLE B-continued
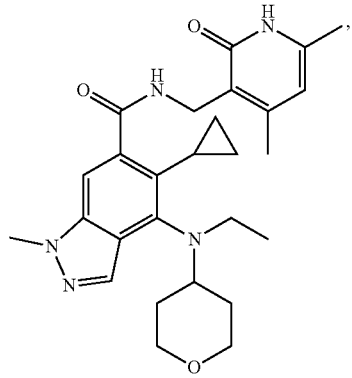
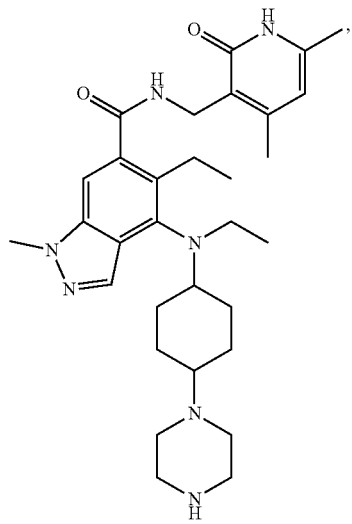
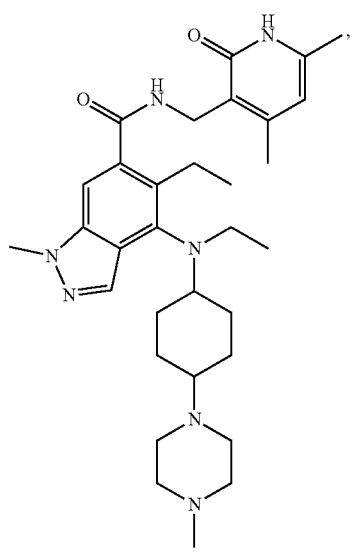

TABLE B-continued
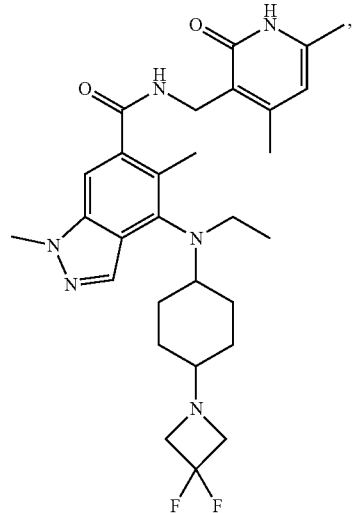
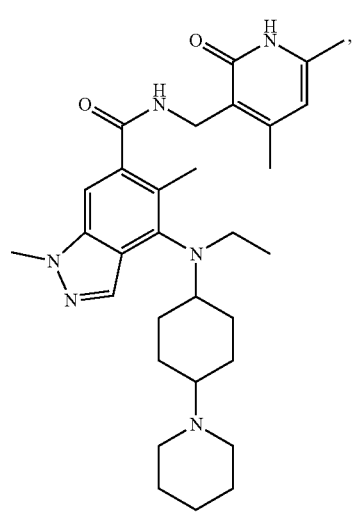
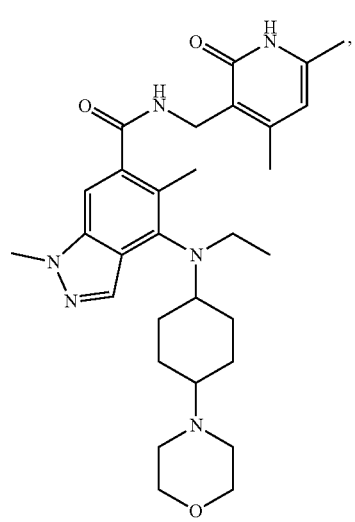
TABLE B-continued
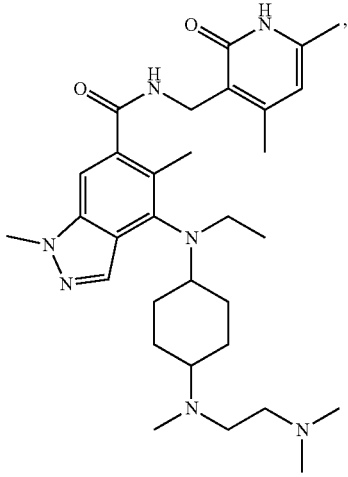
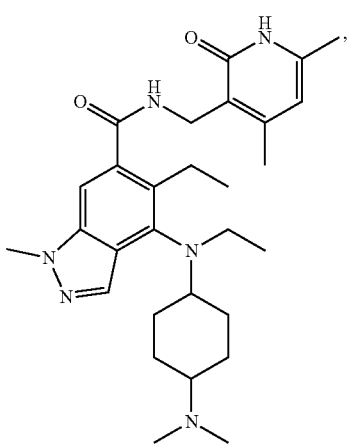
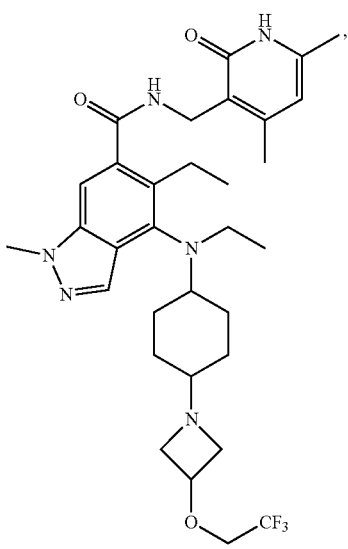

TABLE B-continued
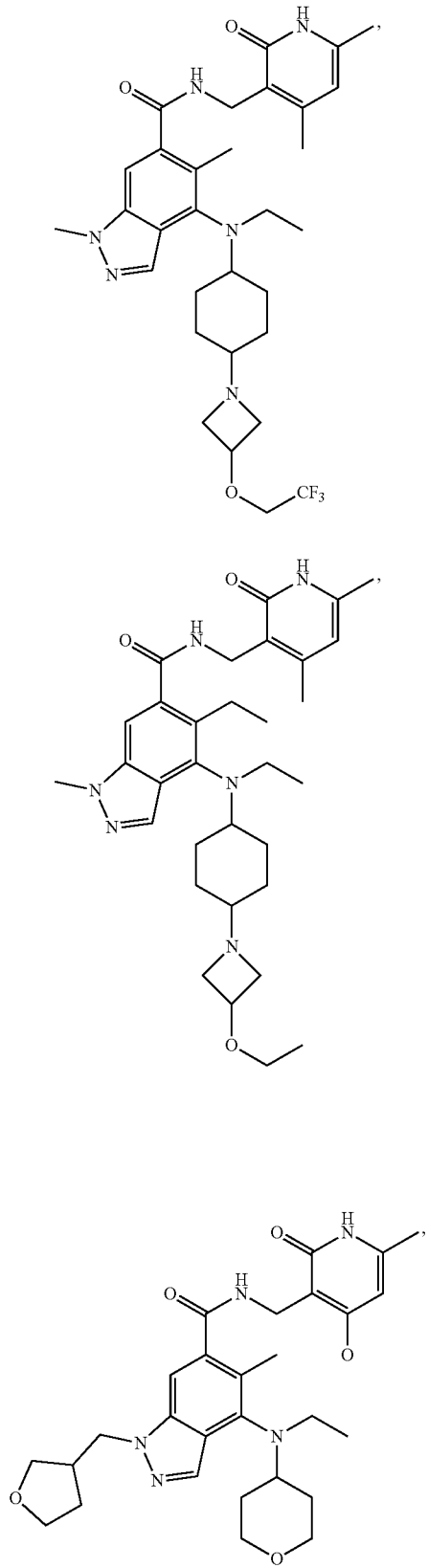
TABLE B-continued
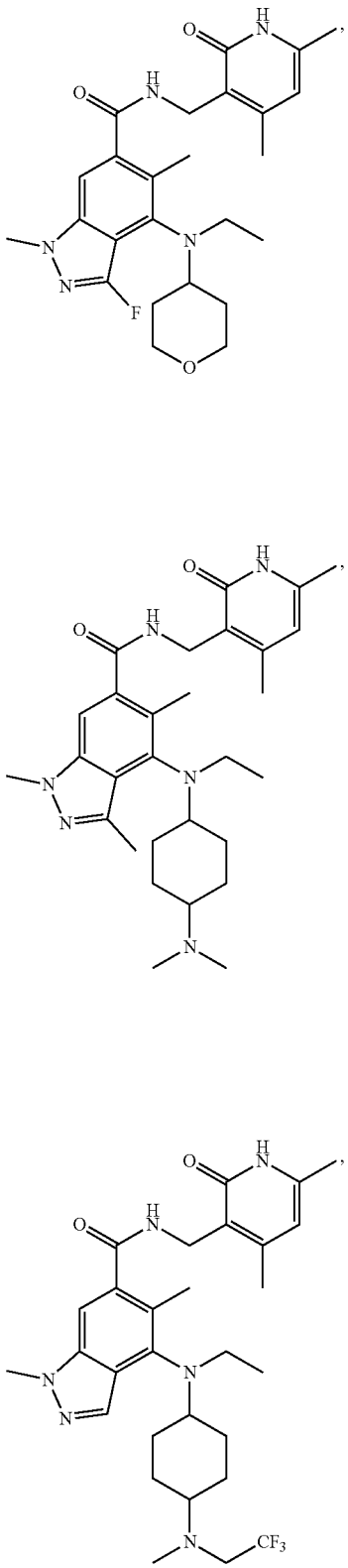

TABLE B-continued

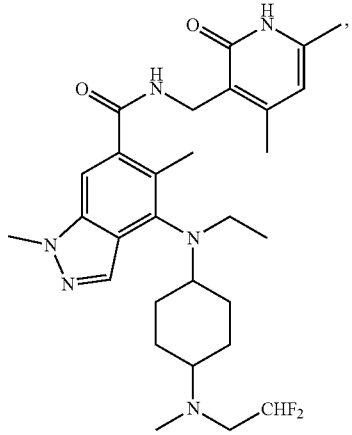

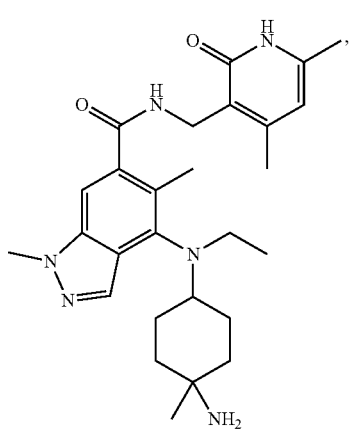

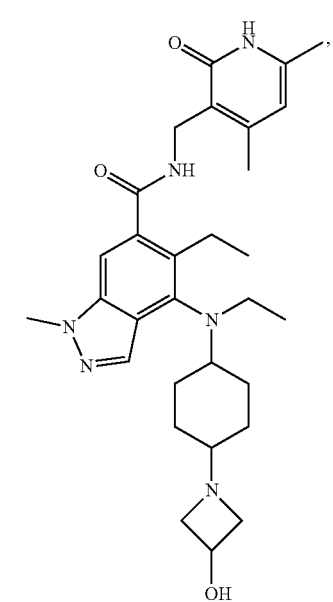

TABLE B-continued

According to a second aspect of the present disclosure, a pharmaceutical composition is provided. The pharmaceutical composition comprises the compound of the first aspect of the present disclosure, or the pharmaceutically acceptable salt, solvate, stereoisomer or prodrug thereof; and a pharmaceutically acceptable carrier.

According to a third aspect of present disclosure, there is provided use of the compound of the first aspect of the present disclosure, or the pharmaceutically acceptable salt, solvate, stereoisomer or prodrug thereof or the pharmaceutical composition of the second aspect of the present disclosure for preparation of EZH2 inhibitors.

According to a third aspect of the present disclosure, there is provided use of the compound of the first aspect of the present disclosure, or the pharmaceutically acceptable salt, solvate, stereoisomer or prodrug thereof or the pharmaceutical composition of the second aspect of the present disclosure for preparation of a drug for EZH2-mediated diseases or conditions.

According to a fourth aspect of the present disclosure, there is provided a method of treating a disease or condition mediated by EZH2, wherein in the method includes administering to a patient in need thereof a therapeutically effective amount of the compound of the first aspect of the present disclosure, or the pharmaceutically acceptable salt, solvate, stereoisomer or prodrug thereof, or the pharmaceutical composition of the second aspect of the present disclosure.

According to a fifth aspect of the present disclosure, there is provided a method of treating a disease or condition mediated by EZH2, comprising administering to a patient in need thereof a therapeutically effective amount of the compound of the first aspect of the present disclosure, or the pharmaceutically acceptable salt, solvate, stereoisomer or prodrug thereof, and another therapeutically active agent.

In another preferred embodiment, the disease or condition mediated by EZH2 is selected from: cancer, pulmonary arterial hypertension, myelofibrosis, human immunodeficiency virus (HIV) disease, graft versus host disease (GVHD), Weaver syndrome, psoriasis vulgaris or liver fibrosis.

In another preferred embodiment, the disease or condition mediated by EZH2 is cancer.

In another preferred embodiment, the cancer mediated by EZH2 includes, but are not limited to, thyroid cancer, cardiac sarcoma, lung cancer, gastrointestinal cancer, genitourinary tract tumor, liver cancer, mantle cell lymphoma, osteosarcoma, nervous system sarcoma, gynecological cancer, hematological system tumor, adrenal neuroblastoma, skin cancer, astrocytic tumor, breast cancer, colorectal cancer, endometrial cancer, head and neck cancer, oral cavity cancer.

It should be understood that each of the above technical features of the present disclosure and each technical feature specifically described below (such as in Embodiments) can be combined with each other within the scope of the present disclosure so as to constitute new or preferred technical solutions which need not be specified again herein.

DETAILED DESCRIPTION OF THE EMBODIMENTS

The inventors have conducted extensive and intensive studies and have unexpectedly found that such 4,5,6-trisubstituted indazole derivatives, particularly the 4,5,6-trisubstituted indazole derivatives in which the 7-position of indazole is unsubstituted, have high inhibitory activities against enzymes such as EZH2 Y641F and the like, and cells such as SU-DHL-6, SU-DHL-10 and the like. Therefore, this series of compounds are hopefully developed as a drug for the treatment of tumors. Based on this, the inventors completed the present disclosure.

Definition of Terms

As used herein, "alkyl" refers to straight and branched saturated aliphatic hydrocarbon groups, $C_{1-8}$ alkyl is an alkyl containing 1 to 8 carbon atoms, preferably $C_{1-6}$ alkyl, more preferably $C_{1-3}$ alkyl with similar definitions; non-limiting examples of alkyl include: methyl, ethyl, n-propyl, isopropyl, n-butyl, isobutyl, tert-butyl, sec-butyl, n-pentane, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl, and their various branched isomers.

As used herein, "cycloalkyl" refers to a saturated or partially unsaturated monocyclic cyclic hydrocarbon group, "$C_{3-8}$ cycloalkyl" refers to a cyclic hydrocarbon group containing 3 to 8 carbon atoms, preferably a $C_{3-6}$ cycloalkyl with similar definition; non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl. cyclooctyl and the like, preferably cyclopropyl, cyclopentyl, cyclohexenyl.

As used herein, "spiro" refers to a polycyclic group in which two monocycles share one carbon atom (spiro atom), wherein these polycyclic groups may contain one or more double bonds, but none of the rings have a completely conjugated π electron system. According to the number of rings, the spiros are divided into bicyclic spiros or polycyclic spiros, wherein the preferably bicyclic spiros are preferable. Moreover, 4 membered/5 membered, 5 membered/5 membered, or 5 membered/6 membered bicyclic spiros are more preferable. For example:

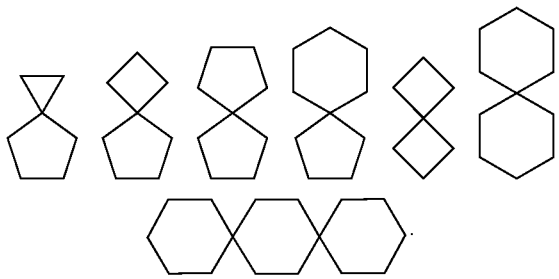

As used herein, "spiroheterocycle" refers to a polycyclic hydrocarbon in which two monocycles share one atom (spiro atom), wherein one or two ring atoms are selected from heteroatoms such as nitrogen, oxygen, or $S(O)_n$ (wherein n is an integer from 0 to 2), the remaining ring atoms are carbon atoms. These spiroheterocycles may contain one or more double bonds, but none of the rings have a completely conjugated π-electron system. According to the number of rings, the spiroheterocycles are divided into bicyclic spiroheterocycles or polycyclic spiroheterocycles, wherein bicyclic spiroheterocycles are preferable. Moreover, 4 membered/5 membered, 5 membered/5 membered, or 5 membered/6 membered bicyclic spiroheterocycles are more preferable. For example:

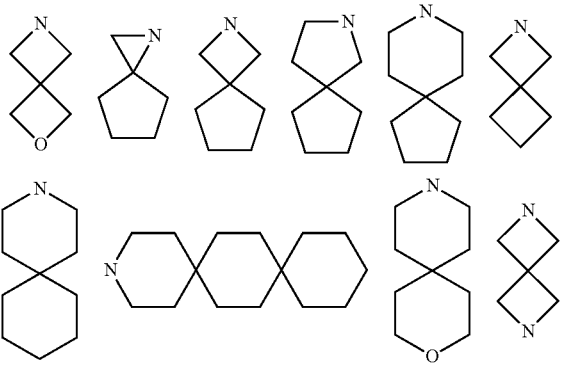

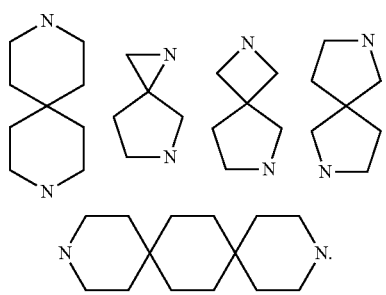

As used herein, "bridged ring" refers to a polycyclic group which shares two or more carbon atoms. The shared carbon atoms are known as bridgehead carbons. Between two bridgehead carbons there may be a carbon chain, or a bond, which is called as a bridge. These bridged rings may contain one or more double bonds, but none of the rings have a completely conjugated π-electron system. Bicyclic or tricyclic bridged rings are preferred. For example:

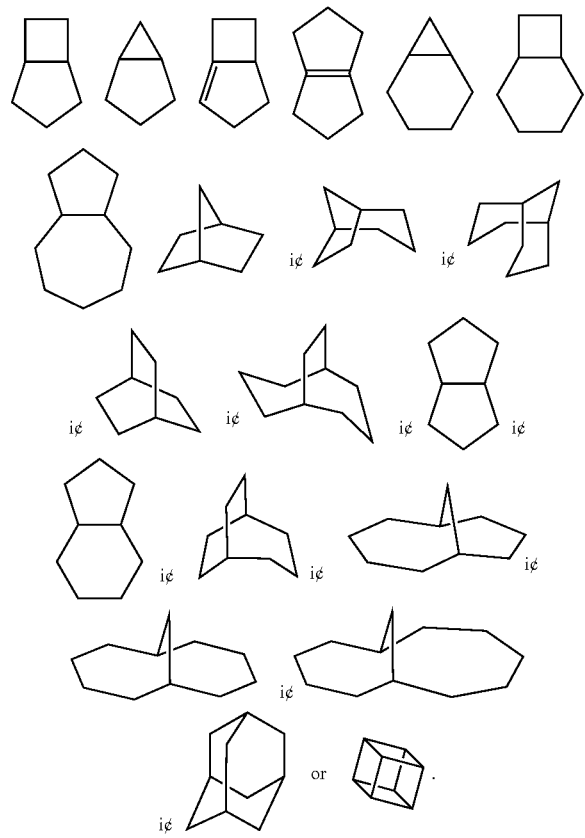

As used herein, "bridged heterocycle" refers to a polycyclic group that shares two or more atoms, wherein one or more ring atoms are selected from heteroatoms such as nitrogen, oxygen, or S(O)$_n$ (wherein n is an integer from 0 to 2), and the remaining ring atoms are carbon atoms. These bridged heterocycles may contain one or more double bonds, but none of the rings have a completely conjugated π-electron system. Bicyclic or tricyclic bridged heterocycles are preferred. For example:

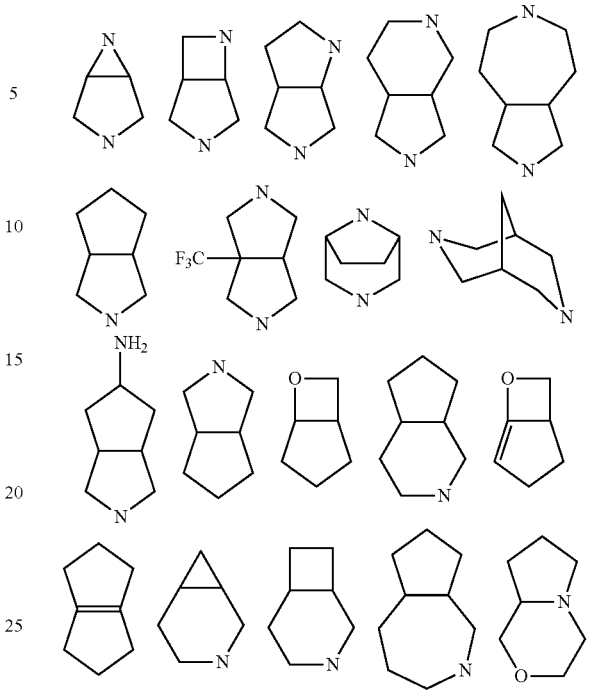

As used herein, "8 to 10 membered bicyclic ring" refers to a two-ring-containing bridged ring containing 8 to 10 ring atoms. The bicyclic ring may be a saturated full-carbon bicyclic or partially unsaturated full-carbon bicyclic ring. Examples of bicyclic ring include (but not limited to):

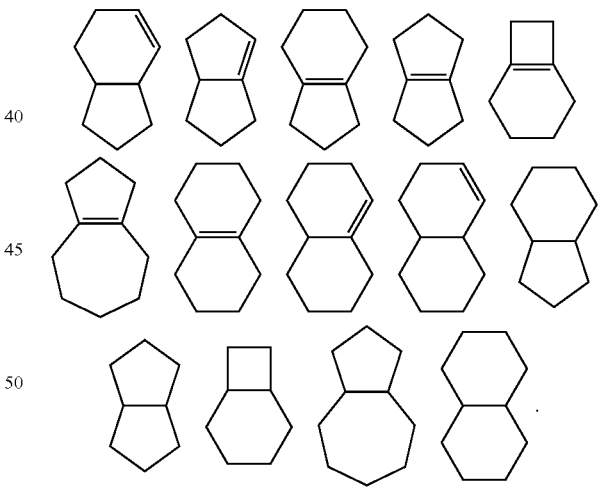

As used herein, "8 to 10 membered bicyclic heterocycle" refers to a two-ring-containing bridged heterocycle containing 8 to 10 ring atoms, wherein 1, 2, 3, 4 or 5 carbon ring atoms are replaced by heteroatoms selected from nitrogen, oxygen or sulfur. Examples of bicyclic heterocycles include, but are not limited to, tetrahydroquinoline ring, tetrahydroisoquinoline ring, decahydroquinoline ring, and the like.

As used herein, "C$_{1-8}$ alkoxy" refers to —O—(C$_{1-8}$ alkyl), wherein alkyl is as defined above. C$_{1-6}$ alkoxy is preferred, and C$_{1-3}$ alkoxy is more preferred. Non-limiting examples include methoxy, ethoxy, propoxy, isopropoxy, butoxy, tert-butoxy, isobutoxy, pentoxy, and the like.

As used herein, "$C_{3-8}$ cycloalkoxy" refers to —O—($C_{3-8}$ cycloalkyl), wherein cycloalkyl is as defined above. $C_{3-6}$ cycloalkoxy is preferred. Non-limiting examples include cyclopropyloxy, cyclobutyloxy, cyclopentoxy, cyclohexyloxy, etc.

As used herein, "$C_{6-10}$ aryl" refers to a full-carbon monocyclic or fused polycyclic (ie, ring that shares an adjacent pair of carbon atoms) group having a conjugated xi-electron system, and refers to an aryl containing 6 to 10 carbon atoms; a phenyl and a naphthyl are preferred, a phenyl is more preferred.

As used herein, "a bond" means that two groups connected thereto are linked by a covalent bond.

As used herein, "halogen" refers to fluorine, chlorine, bromine, or iodine.

As used herein, "halogenated" means that one or more (e.g., 1, 2, 3, 4 or 5) hydrogens in a group are substituted by a halogen.

For example, "halogenated $C_{1-8}$ alkyl" means that the alkyl is substituted by one or more (e.g., 1, 2, 3, 4 or 5) halogens, wherein the alkyl is as defined above. Halogenated $C_{1-6}$ alkyl is preferred, halogenated $C_{1-3}$ alkyl is more preferred. Examples of halogenated $C_{1-8}$ alkyl include, but not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

For another example, "halogenated $C_{1-8}$ alkoxy" means that the alkoxy is substituted by one or more (e.g., 1, 2, 3, 4 or 5) halogens, wherein the alkoxy is as defined above. Halogenated $C_{1-6}$ alkoxy is preferred, and halogenated $C_{1-3}$ alkoxy is more preferred, including, but not limited to, trifluoromethoxy, trifluoroethoxy, monofluoromethoxy, monofluoroethoxy, difluoromethoxy, difluoroethoxy, and the like.

For another example, "halogenated $C_{3-8}$ cycloalkyl" means that a cycloalkyl is substituted by one or more (e.g., 1, 2, 3, 4 or 5) halogens, wherein the cycloalkyl is as defined above. Halogenated $C_{3-6}$ cycloalkyl is preferred. Include, but not limited to, trifluorocyclopropyl, monofluorocyclopropyl, monofluorocyclohexyl, difluorocyclopropyl, difluorocyclohexyl and the like.

As used herein, "deuterated $C_{1-8}$ alkyl" means that an alkyl is substituted by one or more (e.g., 1, 2, 3, 4, or 5) deuterium atoms, wherein the alkyl is as defined above. Deuterated $C_{1-6}$ alkyl is preferred, deuterated $C_{1-3}$ alkyl is more preferred. Examples of deuterated $C_{1-8}$ alkyl include, but not limited to, monodeuterated methyl, monodeuterated ethyl, dideuterated methyl, dideuterated ethyl, trideuterated methyl, trideuterated ethyl and the like.

As used herein, "amino" refers to $NH_2$, "cyano" refers to CN, "nitro" refers to $NO_2$, "benzyl" refers to —$CH_2$-phenyl, "oxo" refers to =O, "carboxyl" refers to —C(O)OH, "acetyl" refers to —C(O)$CH_3$, "hydroxymethyl" refers to —$CH_2$OH, "hydroxyethyl" refers to —$CH_2CH_2$OH, "hydroxy" refers to —OH, "thiol" refers to SH, and the structure of "cyclopropylidene" is:

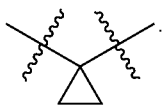 [SMILES: *C1(*)CC1]

As used herein, "heteroaryl ring" and "heteroaryl" can be used interchangeably, and refer to a monocyclic heteroaryl having 5 to 10 ring atoms, preferably 5 or 6 membered monocyclic heteroaryl, or a 8 to 10 membered bicyclic heteroaryl; 6, 10 or 14 it electrons are shared in the ring array; and have 1 to 5 heteroatoms in addition to the carbon atom. "Heteroatom" refers to nitrogen, oxygen or sulfur.

As used herein, "3 to 6 membered saturated or partially unsaturated monocyclic ring" refers to a saturated or partially unsaturated full-carbon monocyclic ring containing 3 to 6 ring atoms.

Examples of monocyclic rings include, but not limited to, cyclopropyl ring, cyclobutyl ring, cyclopentyl ring, cyclopentenyl ring, cyclohexyl ring, cyclohexenyl ring, cyclohexadienyl ring, cycloheptyl ring, cycloheptatrienyl ring, cyclooctyl ring and the like.

As used herein, "3 to 6 membered saturated monocyclic ring" means a 3 to 6 membered monocycle in which 1, 2 or 3 carbon atoms are substituted by a heteroatom selected from nitrogen, oxygen, or $S(O)_t$ (wherein t is an integer from 0 to 2), but which does not include a ring portion of —O—O—, —O—S— or —S—S— is not included, and the remaining ring atoms of which are carbon; 4 to 6 membered is preferred, and 5 to 6 membered is more preferred. Examples of saturated heteromonocycles include, but not limited to, epoxypropane, azetidine, oxetane, tetrahydrofuran, tetrahydrothiophene, pyrrolidine, piperidine, pyrroline, oxazolidine, piperazine, dioxolane, dioxane, morpholine, thiomorpholine, thiomorpholine-1,1-dioxide, tetrahydropyran and the like.

As used herein, "5 to 6 membered monocylic heteroaryl ring" refers to a monocylic heteroaryl ring containing 5 to 6 ring atoms, examples include but are not limited to, thiophene ring, N-alkylpyrrole ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

As used herein, "8 to 10 membered bicyclic heteroaryl ring" refers to a bicyclic heteroaryl ring containing 8 to 10 ring atoms, including, for example, but not limited to, benzofuran, benzothiophene, indole, isoindole, quinoline, isoquinoline, indazole, benzothiazole, benzimidazole, quinazoline, quinoxaline, cinnoline, phthalizine.

As used herein, "substituted" means that one or more hydrogen atoms, preferably 1-5 hydrogen atoms in a group are independently substituted by a corresponding number of substituents, and more preferably 1 to 3 hydrogen atoms are independently substituted by a corresponding number of substituents. It goes without saying that the substituents are only in their possible chemical positions, and those skilled in the art can determine (by experiment or theory) the possible or impossible substitutions without undue effort. For example, an amino or hydroxy with a free hydrogen may be unstable when combined with a carbon atom having an unsaturated (eg olefinic) bond.

As used herein, any one of the groups herein may be substituted or unsubstituted. When the above groups are substituted, the substituents are preferably 1 to 5 groups independently selected from the group consisting of CN, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), amino substituted by $C_{1-8}$ alkyl, amino, amino substituted by halogenated C$_{1-8}$ alkyl, 4 to 6 membered saturated heteromonocycle, 5 to 6 membered monocylic heteroaryl ring, 8 to 10 membered bicyclic heteroaryl ring, spiro, spiroheterocycle, bridged ring and bridged heterocycle.

The above-mentioned various substituents themselves of the present disclosure can also be substituted by the groups described herein.

When 4 to 6 membered saturated heteromonocycles described herein are substituted, the positions of the substituents may be at their possible chemical positions, and representative substitutions of the exemplary heteromonocycles are shown below:

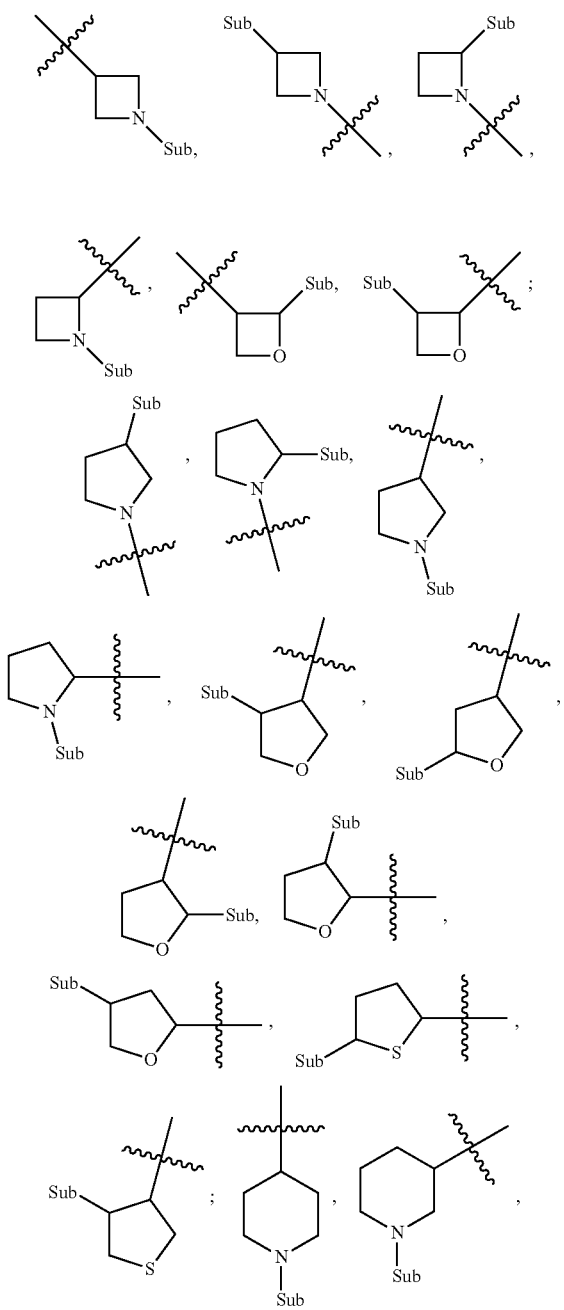

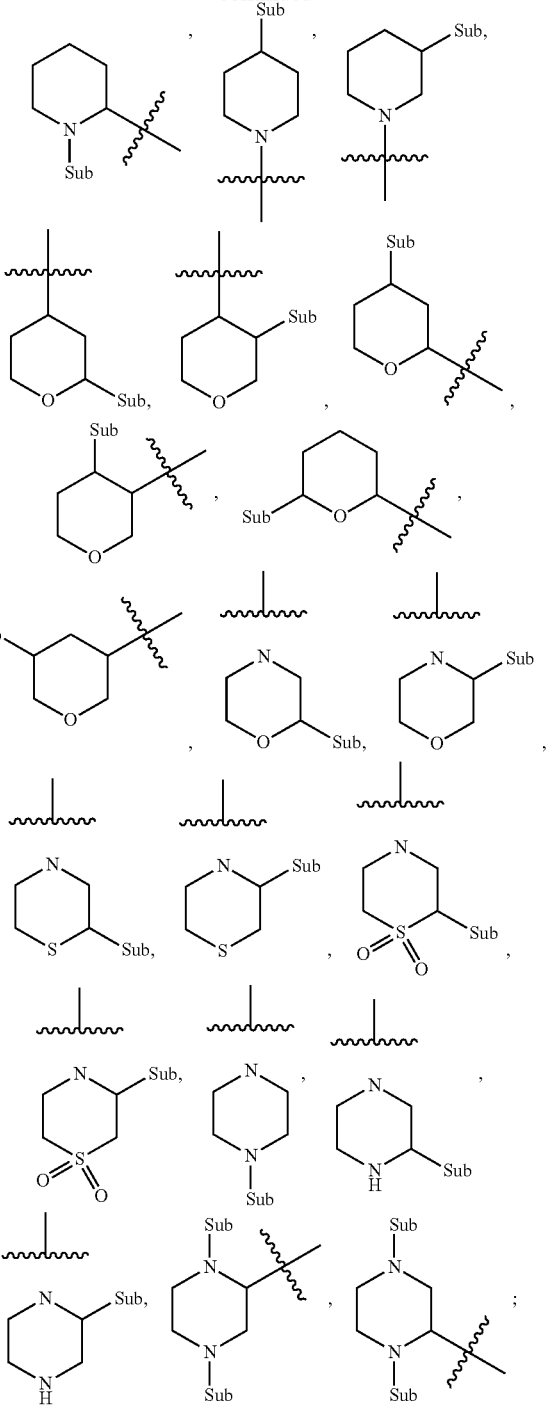

wherein "Sub" represents the various types of substituents described herein; "〜〜〜" represents connections with other atoms.

As used herein, "EZH2 inhibitor" refers to an agent that can inhibit increased expression of the histone lysine N-methyltransferase EZH2 (refers to a compound of formula (I) in the present disclosure). EZH2 is a catalytic functional subunit of PRC2, and is responsible for the methylation of specific histone H3 at Lys27 (H3K27) and essential for stem cell self-renewal.

As used herein, "disease or condition mediated by EZH2" refers to an abnormal condition in a patient resulting from an abnormal epigenetic modification caused by abnormal expression of the histone lysine N-methyltransferase EZH2.

As used herein, "therapeutically effective amount" refers to an amount of the compound of the present disclosure that will elicit the biological or medical response to an individual, for example, reduction or inhibition of an enzyme or a protein activity, or amelioration of a symptom, alleviation of a condition, slowing or delaying disease progression, or prevention of a disease, etc.

As used herein, "pharmaceutically acceptable carrier" refers to a non-toxic, inert, solid, semi-solid substance or liquid filler, diluent, encapsulating material or auxiliary formulation or any type of excipient that is compatible with the patient who is preferably a mammal and more preferably a human. It is suitable for delivering an active agent to a target without stopping the activity of the agent.

As used herein, "patient" refers to an animal, preferably a mammal, and more preferably a human. The term "mammal" refers to a warm-blooded vertebrate mammal, including, for example, cat, dog, rabbit, bear, fox, wolf, monkey, deer, rat, pig and human.

As used herein, "treating" refers to alleviating, delaying progression, attenuating, preventing, or maintaining an existing disease or condition (eg, cancer). Treatment also includes curing one or more symptoms of the disease or condition, preventing its development or reducing to some extent.

Preparation Method

The present disclosure provides a method of preparing the compound of formula (I), the compound of the present disclosure can be prepared by a variety of synthetic operations, exemplary methods of preparing these compounds may include (but not limited to) the processes described below.

Preferably, the compound of formula (I) can be prepared through the following schemes and exemplary methods described in embodiments, as well as the related publications available for those skilled in the art.

In the specific operation process, The steps of method can be extended or combined as desired.

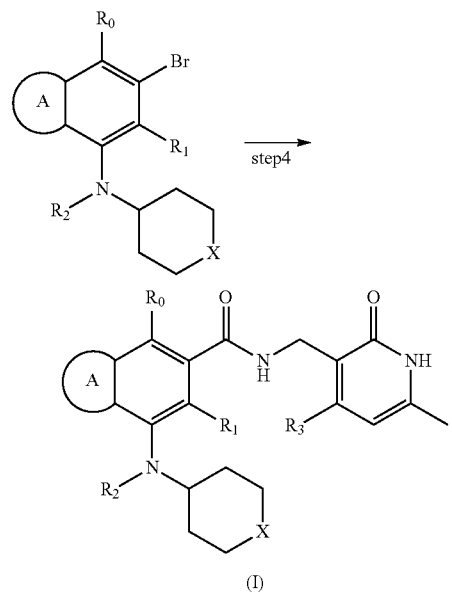

Step 1: a nitro compound was converted into a corresponding amine compound, and the amine compound was reduced using a metal (which can be but not limited to iron powder, zinc powder) under acidic conditions, or reduced by palladium-carbon catalyzed hydrogenation.

Step 2: a nucleophilic addition of an amino group at the 4-position of the indazole compound and a ketone can be catalysted by a catalyst (which may be but not limited to sodium triacetoxyborohydride) under acidic conditions.

Step 3: reaction conditions for the nucleophilic addition of the amino group and an aldehyde were the same as those in step 2.

Step 4: a bromo group in an aromatic ring of the indazole compound was subjected to carbonylation with for example, molybdenum hexacarbonyl under the action of palladium catalyst, followed by condensation with an amine to obtain the target compound (I); the palladium catalyst used may be but is not limited to Pd (dppf)Cl$_2$, and the base used may be but not limited to triethylamine.

Scheme 1

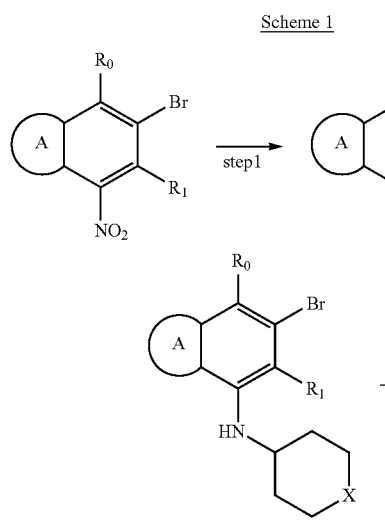

Scheme 2

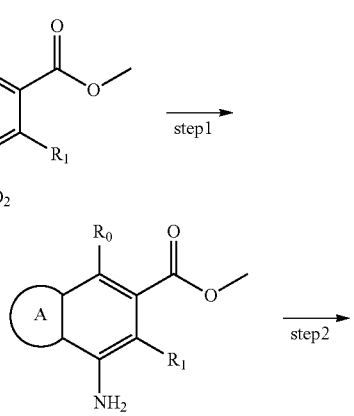

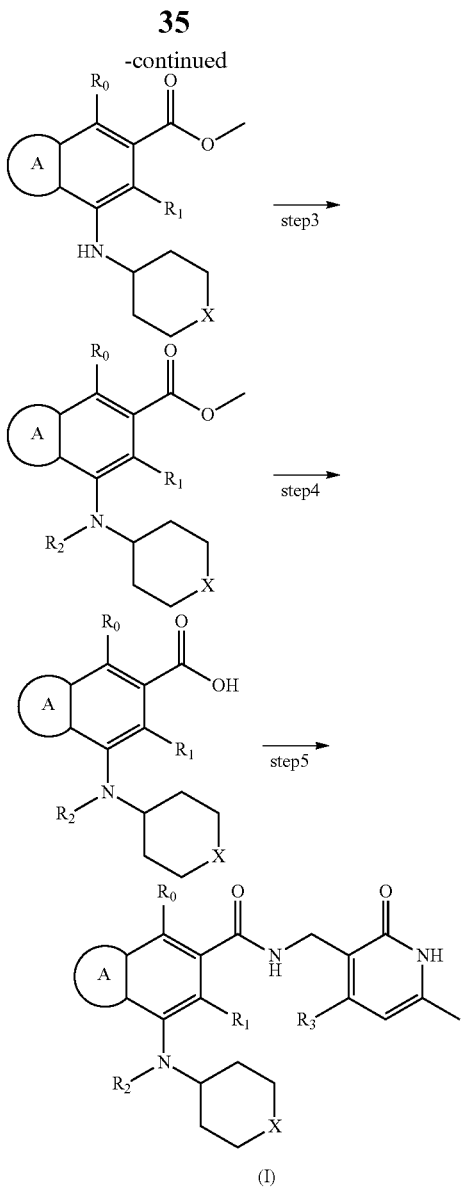

Step 1: a nitro compound was converted into a corresponding amine compound, and the corresponding amine compound was reduced using a metal (which can be but not limited to iron powder, zinc powder) under acidic conditions, or reduced by palladium-carbon catalyzed hydrogenation.

Step 2: a nucleophilic addition of an amine at the 4-position of the indazole compound and a ketone can be catalysted by a catalyst (which may be but not limited to sodium triacetoxyborohydride) under acidic conditions.

Step 3: reaction conditions for the nucleophilic addition of the amino group and aldehyde were the same as those in step 2.

Step 4: Hydrolysis of an ester, the compound can be hydrolyzed in, for example, an alkaline solution of methanol. The base used can be but is not limited to sodium hydroxide.

Step 5: a carbonyl group of the indazole compound was condensed with an amine under the action of a condensing agent to form an amide compound (I).

The reactions in the above steps are all conventional reactions known to those skilled in the art.

Unless otherwise specified, the reagents and raw material compounds used in the synthetic route are all commercially available, or can be prepared by those skilled in the art by referring to known methods according to the different compound structures designed.

Compared with the prior art, the main advantages of the present disclosure are to provide a series of novel 4,5,6-trisubstituted indazole derivatives which have high inhibitory activity against EZH2 and can be used as drugs for the treatment of tumors.

The present disclosure will be further illustrated below with reference to the specific examples. It should be understood that these examples are only to illustrate the present disclosure but not to limit the scope of the present disclosure. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present disclosure.

As used herein, DMB refers to 2,4-dimethoxybenzyl, THF refers to tetrahydrofuran, EA refers to ethyl acetate, PE refers to petroleum ether, $Ac_2O$ refers to acetic anhydride, NBS refers to N-bromosuccinimide, DCM refers to dichloromethane, AIBN refers to azodiisobutyronitrile, $Pd(dppf)Cl_2$ refers to [1,1'-bis(diphenylphosphino)ferrocene]palladium dichloride, TFA refers to trifluoroacetic acid, TBSCl refers to tert-butyldimethylchlorosilane, NCS refers to N-chlorosuccinimide, DHP refers to dihydrogenpyran, $LiAlH_4$ refers to lithium aluminium hydride, PMB refers to p-methoxybenzyl, LiHMDS refers to lithium bistrimethylsilylamide, $Pd_2(dba)_3$ refers to tris(dibenzylideneacetone)dipalladium, RuPhos refers to 2-dicyclohexylphosphoryl-2',6'-diisopropoxy-1,1'-biphenyl, DMAP refers to 4-dimethylaminopyridine, THP refers to tetrahydropyran, n-BuLi refers to n-butyllithium, TMsOTf refers to trimethylsilyl trifluoromethanesulfonate, TEBAC refers to triethylbenzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIEA refers to N,N-diisopropylethylamine, BINAP refers to (2R,3S)-2,2'-bis diphenylphosphino-1,1'-binaphthyl.

As used herein, room temperature refers to about 20-25° C.

Preparation of Intermediate 1a

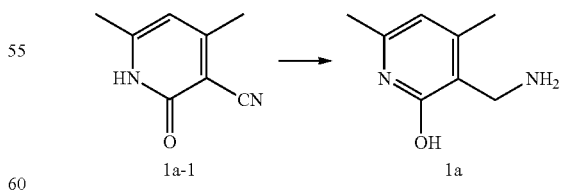

To a solution of compound 1a-1 (22.5 g, 152 mmol) in tetrahydrofuran (500 mL) was slowly added lithium aluminum hydride (11.5 g, 0.3 mol) under ice-bath, and the mixture was stirred at room temperature overnight. 15 mL of water and 30 mL of sodium hydroxide solution (15%) were added to the system respectively, then the system was filtered, and the filtrate was concentrated to give compound 1a as a white solid. MS m/z (ESI): N/A.

Preparation of Intermediate 2a

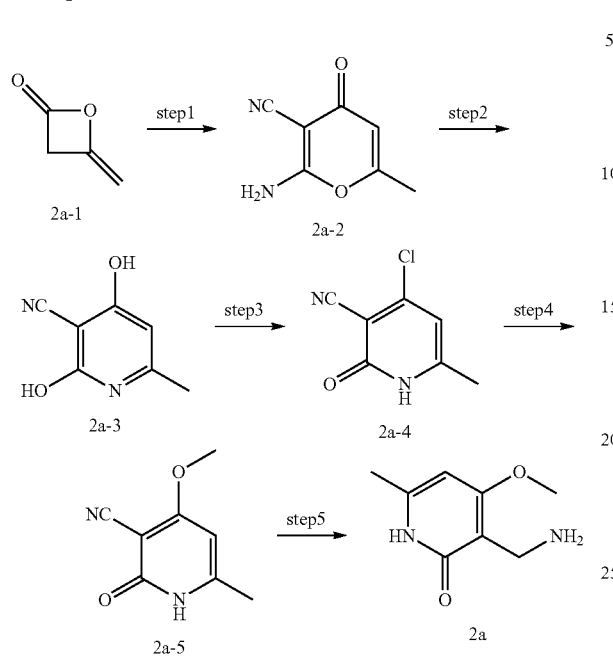

Step 1: a solution of compound malononitrile (12 g, 181.7 mmol) in dry tetrahydrofuran (225 mL) was stirred in an ice bath for 1 hour, sodium hydride (4.8 g, 199.8 mmol) was added in batchs and stirred for 2 hours, compound 2a-1 (16.8 g, 199.8 mmol) was added dropwise, and the mixture was slowly warmed to room temperature and reacted for 1 hour. The reaction solution was quenched with hydrochloric acid solution and extracted with ethyl acetate, and the organic layer was dried and concentrated to give compound 2a-2 as a yellow solid, which was used directly for the next step. MS m/z (ESI): 151 [M+H]$^+$.

Step 2: a mixture of compound 2a-2 (28 g, 181.7 mmol), hydrochloric acid (23.2 g, 4 M, 636.4 mmol) and water (160 mL) was stirred under reflux for 5 hours. The reaction solution was filtered, and the solid residue was recrystallized from methanol to obtain 25 g of compound 2a-3. MS m/z (ESI): 151 [M+H]$^+$.

Step 3: to compound 2a-3 (80 mg, 0.53 mmol) was added 2 mL of phosphorus oxychloride, and the mixture was stirred at 100° C. for 2 hours. The reaction was followed by LC-MS until completion. The mixture was cooled and poured into ice water, adjusted to pH 8 with aqueous ammonia, extracted with ethyl acetate, dried and concentrated to give 100 mg of compound 2a-4 as a white solid. MS m/z (ESI): 169 [M+H]$^+$.

Step 4: a mixture of compound 2a-4 (300 mg, 1.78 mmol), sodium methoxide (481 mg, 8.9 mmol) and methanol (15 mL) was microwaved at 100° C. for 16 hours. The reaction was followed by LC-MS until completion. The reaction solution was concentrated to remove the solvent. Water was added to the residue, adjusted to pH 7 and filtered to obtain 225 mg of compound 2a-5 as a solid. MS m/z (ESI): 419 [M+H]$^+$.

Step 5: the preparation method was the same as that of compound 1a, except that compound 1a-1 in the preparation method of compound 1a was replaced with compound 2a-5. MS m/z (ESI): 152 [M+H]$^+$.

Preparation of Intermediate 3a

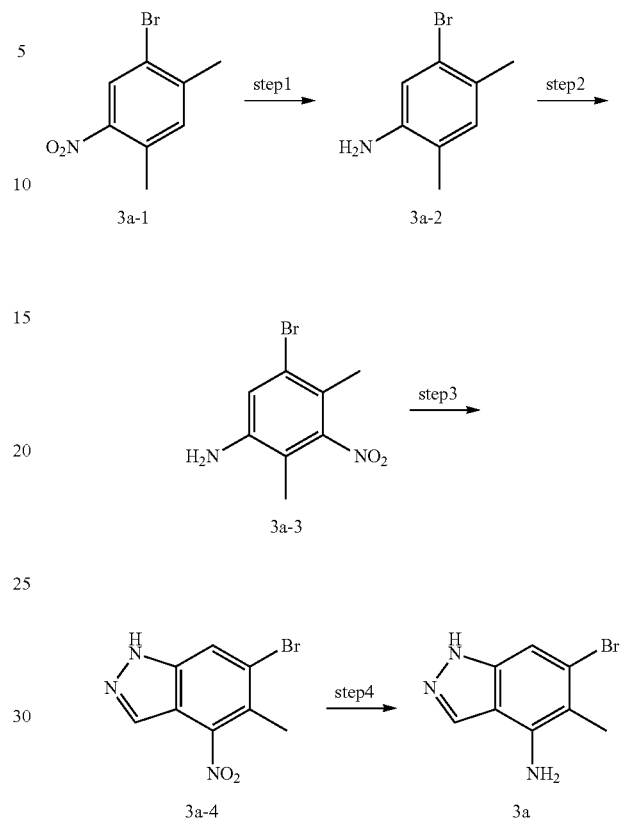

Step 1: to a solution of compound 3a-1 (1 g, 4.35 mmol) in ethanol (10 mL) was added a solution of ammonium chloride (697 mg, 13.04 mmol) in water (2 mL) and iron powder (364 mg, 6.52 mmol). The mixture was stirred under reflux for 2 hours. The reaction was followed by LC-MS until completion. The reaction solution was filtered, the filtrate was concentrated and the residue was dissolved in water and filtered again to give 700 mg of compound 3a-2 as a white solid. MS m/z (ESI): 202 [M+H]$^+$.

Step 2: a solution of compound 3a-2 (500 mg, 45 mmol) in sulfuric acid (7.5 mL) was added potassium nitrate (278 mg, 2.75 mmol) in batchs at −5° C. and the mixture reacted at this temperature for 1 hour. The reaction was followed by LC-MS until completion. The mixture was poured into ice water and the pH was adjusted to 8. The precipitated solid was filtered to give 400 mg of compound 3a-3. MS m/z (ESI): 247 [M+H]$^+$.

Step 3: to a solution of compound 3a-3 (2 g, 8.16 mmol) in acetic acid (30 mL) was added dropwise a solution of sodium nitrite (619 mg, 8.98 mmol) in water (5 mL) at 40° C. and the mixture was stirred at 40° C. for 1 h. The reaction was followed by LC-MS until completion. The reaction solution was poured into water, extracted with ethyl acetate, dried and concentrated to obtain 2 g of compound 3a-4 as a solid. MS m/z (ESI): 256 [M+H]$^+$.

Step 4: the preparation method was the same as that of compound 3a-2, except that compound 3a-1 in the preparation method of compound 3a-2 was replaced with compound 3a-4, and after purification by combiflash, compound 3a as a red solid (800 mg, 45%) was obtained. MS m/z (ESI): 226[M+H]$^+$.

Preparation of Intermediate 4a

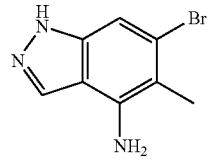

3a

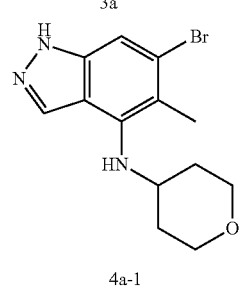

4a-1

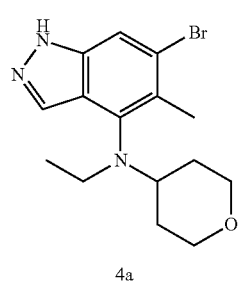

4a

Step 1: a solution of compound 3a (800 mg, 3.54 mmol), tetrahydropyrone (708 mg, 7.08 mmol), and 5 mL of trifluoroacetic acid in 1,4-dioxane (50 mL) was stirred at room temperature for 2 hours, sodium triacetoxyborohydride (2.25 mg, 10.62 mmol) was added, and then the mixture was stirred at room temperature for 4 hours. The reaction was followed by LC-MS until completion. The reaction solution was poured into water, and the mixture was adjusted to pH 8 with sodium bicarbonate solution, extracted with ethyl acetate, dried and concentrated to give 1 g of compound 4a-1. MS m/z (ESI): 312.2 [M+H]$^+$.

Step 2: a solution of compound 4a-1 (1 g, 3.22 mmol), acetaldehyde (710 mg, 16.12 mmol), and 3 mL of acetic acid in 1,4-dioxane (30 mL) was stirred at room temperature for 2 hours, sodium triacetoxyborohydride (2.05 g, 9.67 mmol) was added, and the mixture was stirred overnight at room temperature. The reaction was followed by LC-MS until completion. The reaction solution was poured into water, adjusted to pH 8 with sodium bicarbonate solution, extracted with ethyl acetate and concentrated, purified by combiflash to give red compound 4a (280 mg, 26%). MS m/z (ESI): 340.1 [M+H]$^+$.

Preparation of Intermediate 5a

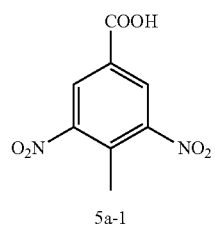

5a-1

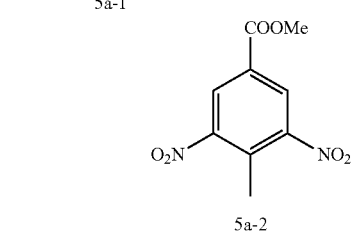

5a-2

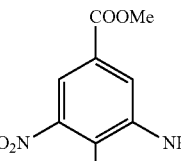

5a-3

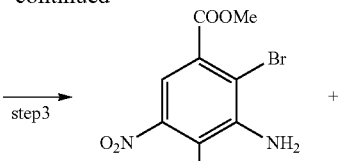

5a-4-1

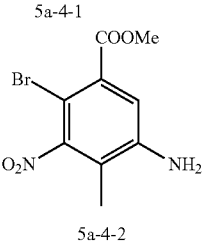

5a-4-2

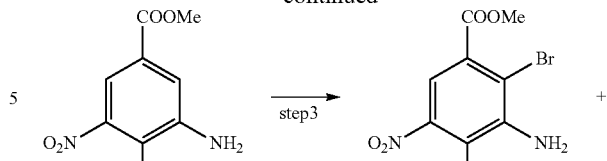

5a-4-1

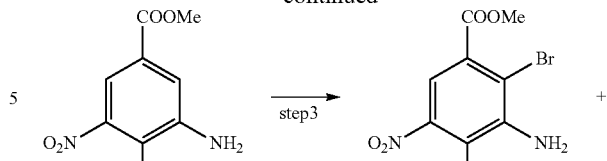

5a-5

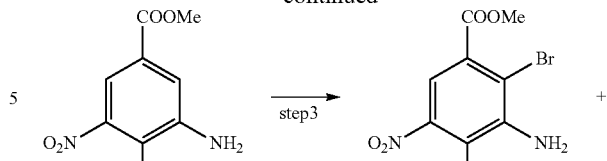

5a-6

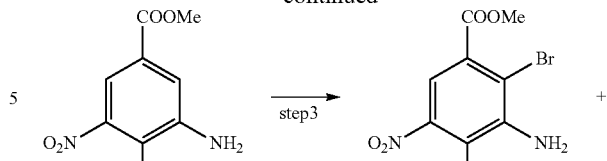

5a-7

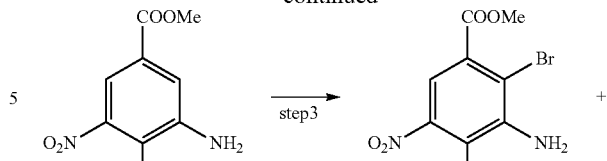

5a-8

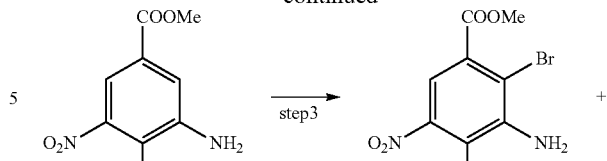

5a

Step 1: to a solution of compound 5a-1 (8 g, 35.3 mmol) in anhydrous methanol (100 mL) was added thionyl chloride (7.7 mL, 106.1 mmol), and the mixture was stirred under reflux for 20 hours.

The reaction was followed by LC-MS until completion. The reaction solution was cooled and concentrated to remove most of the solvent, and filtered, and the filter cake was dried in vacuo to give 7.5 g of compound 5a-2. MS m/z (ESI): 241 [M+H]$^+$.

Step 2: to a solution of compound 5a-2 (7.6 g, 31.64 mmol) in acetic acid (150 mL) was added iron powder (14 g, 253 mmol) in batchs. The reaction temperature was controlled at 20-30° C. After completion of the addition, the mixture was stirred continuously for 10 min. The reaction was followed by LC-MS until completion. The reaction solution was filtered, the filtrate was poured into water and extracted with ethyl acetate, and the organic layer was concentrated and purified by combiflash to give compound 5a-3 as a yellow solid (3.5 g, 52.6%). MS m/z (ESI): 211[M+H]$^+$.

Step 3: to a solution of compound 5a-3 (850 mg, 4.04 mmol) in DMSO (20 mL) was added dropwise a solution of NBS (756 mg, 4.25 mmol) in DMSO (1.5 mL), and the mixture was stirred at room temperature for 16 hours. The reaction was followed by LC-MS until completion. The reaction solution was poured into water and extracted with ethyl acetate. The organic phase was washed with saturated brine, dried over anhydrous sodium sulfate, concentrated and purified by column chromatography to give compound 5a-4-1 (800 mg, 68%) and compound 5a-4-2 (178 mg, 15%), MS m/z (ESI): 290.8 [M+H]$^+$.

Step 4: the preparation method was the same as that of compound 3a-4, except that compound 3a-3 in the preparation method of compound 3a-4 was replaced with compound 5a-4-1. MS m/z (ESI): 299.8 [M+H]$^+$.

Step 5: a solution of compound 5a-45 (3 g, 0.01 mol), methyl iodide (4.2 g, 0.03 mol), and potassium carbonate (2.2 g, 0.015 mol) in DMF was stirred at room temperature for 2 hours. The reaction was followed by LC-MS until completion. The reaction solution was poured into water (150 ml), stirred for 30 min, filtered, and the filter cake was dried in vacuo to give compound 5a-6 (2.7 g, 86%), MS m/z (ESI): 316.1 [M+H]$^+$.

Step 6: the preparation method was the same as that of compound 3a-4, except that compound 3a-3 in the preparation method of 3a-4 was replaced with compound 5a-6. MS m/z (ESI): 284[M+H]$^+$.

Step 7: a mixed solution of compound 5a-67 (8 g, 0.026 mol), potassium trifluorovinyl borate (7 g, 0.052 mol), Pd(dppf)Cl$_2$ (0.95 g, 0.0013 mol), sodium carbonate (5.5 g, 0.052 mol) in dioxane/water (100 ml/10 ml) was stirred at 100° C. overnight. The reaction was followed by LC-MS until completion. The reaction solution was cooled to room temperature, and filtered, the filtrate was extracted with ethyl acetate, and the organic phase was dried over anhydrous sodium sulfate, filtered and concentrated, purified by column chromatography to obtain compound 5a-78 as a beige solid (2.7 g, 40%). MS m/z (ESI): 2632.2 [M+H]$^+$.

Step 8: a solution of compound 5a-78 (1 g, 4.4 mmol) and platinum dioxide (100 mg, 0.22 mmol) in ethyl acetate (20 ml) was stirred at room temperature under a hydrogen atmosphere for 3 hours. The reaction was followed by LC-MS until completion. The reaction solution was filtered, and the filtrate was concentrated and purified by column chromatography to give compound 5a as a yellow solid (600 mg, 59%). MS m/z (ESI): 234.2 [M+H]$^+$.

Preparation of Intermediate 6a

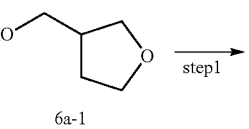

6a-1

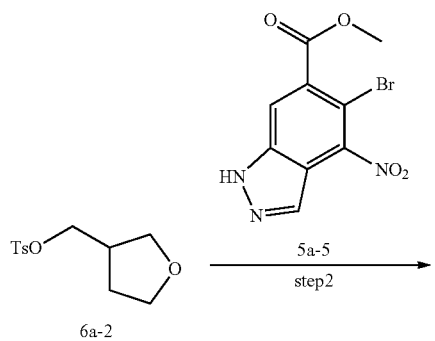

6a-2

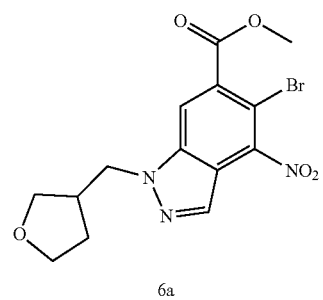

6a

Step 1: to a solution of compound 6a-1 (2 g, 102 mmol) in dichloromethane (40 ml) was added triethylamine (3.96 g, 39.17 mmol) and TsCl (4.48 g, 23.50 mmol), and the reaction solution was stirred overnight at room temperature. The reaction solution was poured into water and extracted with dichloromethane. The organic phase was dried over anhydrous sodium sulfate, filtered, concentrated, and purified by column chromatography to give compound 6a-2 as an oil (3 g, 60%). MS m/z (ESI): 257.0 [M+H]$^+$.

Step 2: a solution of compound 5a-5 (2 g, 6.67 mmol), compound 6a-2 (2.56 g, 10 mmol), potassium carbonate (1.84 g, 13.33 mmol), and potassium iodide (1.66 g, 10 mmol) in acetone was refluxed for 8 h. The reaction solution was cooled to room temperature, filtered, and the filtrate was concentrated and purified by column chromatography to give compound 6a as a brown solid (600 mg, 23%). MS m/z (ESI): 386.1 [M+H]$^+$.

Preparation of Intermediate 7a-9a

Compounds 6a and 5a-6 was used as raw materials, with reference to the preparation method of intermediate 5a, except that potassium trifluorovinyl borate in step 6 was replaced with methyl boronic acid and cyclopropyl boronic acid, the base in step 6 was replaced with barium carbonate and potassium carbonate, and the platinum dioxide in step 7 was re laced with palladium carbon.

| Intermediate No. | structure | MS m/z(ESI) |
| --- | --- | --- |
| 7a | 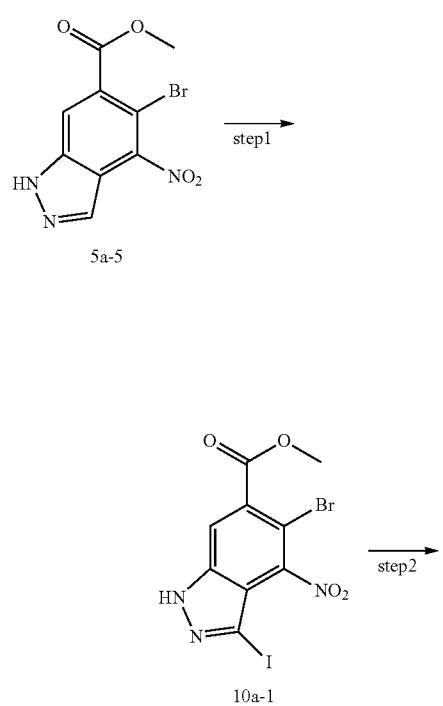 | 290.2 |
| 8a | 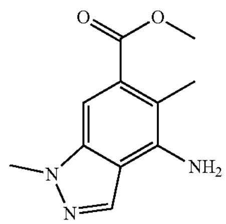 | 220.1 |
| 9a | 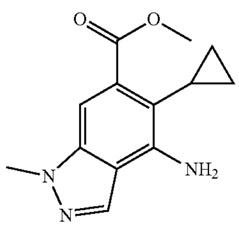 [SMILES: COC(=O)c1cc2c(cnn2C)c(N)c1C1CC1] | 246.2 |

Preparation of Intermediate 10a

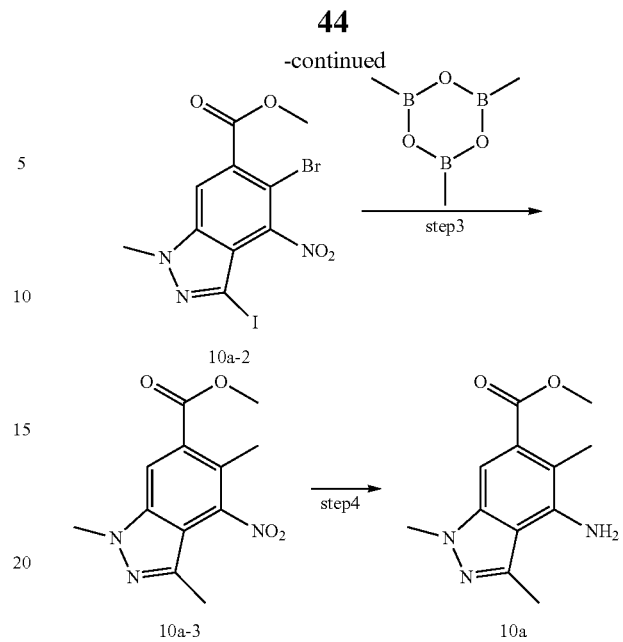

Step 1a: a solution of compound 5a-5 (20 g, 0.067 mol) and NIS (16.6 g, 0.074 ml) in DMF was stirred at 60° C. for 3 h, and the reaction was followed by LC-MS until completion. The reaction solution was cooled to room temperature and poured into water (600 ml), stirred for 30 min, filtered, and the filter cake was washed with water and dried to give compound 10a-1 (25 g), MS m/z (ESI): 425.7 [M+H]$^+$.

Step 2: a solution of compound 10a-1 (25 g, 0.059 mol), potassium carbonate (12.3 g, 0.09 mol), and methyl iodide (12.8 g, 0.09 mol) in DMF (100 ml) was stirred at room temperature for 2 h, and the reaction was followed by LC-MS until completion. The reaction solution was poured into water, filtered, and the filter cake was washed with water and dried to give compound 10a-2 (17 g), MS m/z (ESI): 439.8 [M+H]$^+$.

Step 3: to a mixed solution of compound 10a-2 (400 mg, 0.91 mmol) and trimethyl cyclotriboroxane (568 mg, 4.55 mmol), potassium carbonate (376 mg, 2.73 mmol) in dioxane/water (5 ml/1 ml) was added a catalytic amount of Pd(dppf)Cl$_2$, and the reaction solution was stirred under nitrogen at 105° C. for 16 hours. The reaction was followed by LC-MS until completion. Water was added to the reaction solution, and the mixture was extracted with ethyl acetate. The organic phase was dried over anhydrous sodium sulfate, filtered, concentrated, and purified by column chromatography to give compound 10a-3 (200 mg, 83%). MS m/z (ESI): 264 [M+H]$^+$.

Step 4: the same as the preparation method of step 2 of intermediate 7a, MS m/z (ESI): 234 [M+H]$^+$.

Preparation of Intermediate 11a

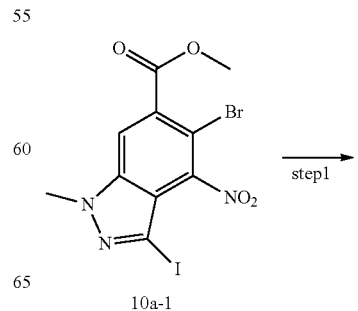

-continued

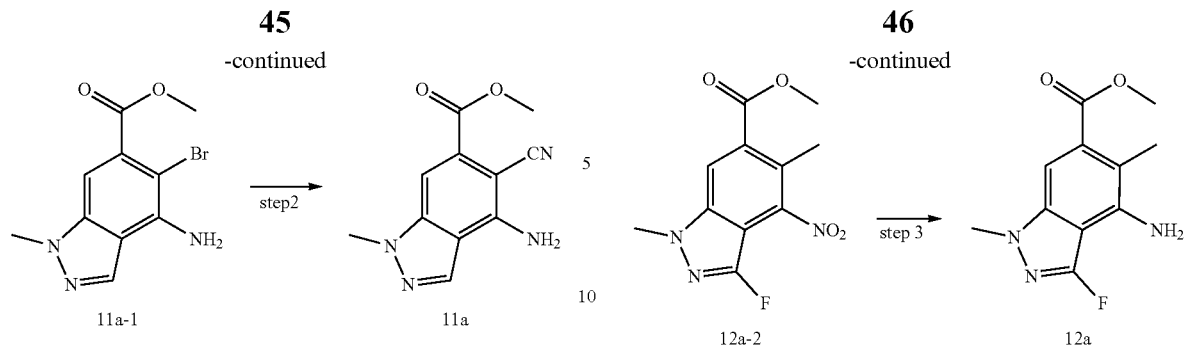

Step 1: to a mixed solution of compound 10a-1 (16.4 g, 37.3 mmol) in methanol/glacial acetic acid (400 ml/400 ml) was slowly added zinc powder at −5 to 0° C. and the reaction solution was stirred at 0° C. for 20 min, and then stirred at room temperature for 20 min. The reaction was followed by LC-MS until completion. The reaction solution was filtered through celite. The filtrate was added with water (1 L) and the pH was adjusted to 7-8 with saturated sodium carbonate solution. The mixture was extracted with dichloromethane, the organic phase was washed with saturated brine, dried, filtered, and concentrated, and purified by column chromatography to obtain compound 11a-1 as a gray solid (5.3 g, 50%), MS m/z (ESI): 284.1[M+H]⁺.

Step 2: a solution of compound 11a-1 (300 mg, 1.06 mmol), zinc cyanide (250 mg, 2.21 mmol), and tetrakis(triphenylphosphine) palladium (128 mg, 0.11 mmol) in DMF (4 ml) was microwaved under nitrogen protection at 150° C. for 30 min. The reaction was followed by LC-MS until completion. Water and ethyl acetate were added to the reaction solution, and the organic phase was separated, washed with saturated brine, dried over anhydrous sodium sulfate, filtered, and concentrated. The crude product was recrystallized from ethyl acetate to give compound 11a as a gray solid (210 mg, 64%), MS m/z (ESI): 231.2 [M+H]⁺.

Preparation of Intermediate 12a

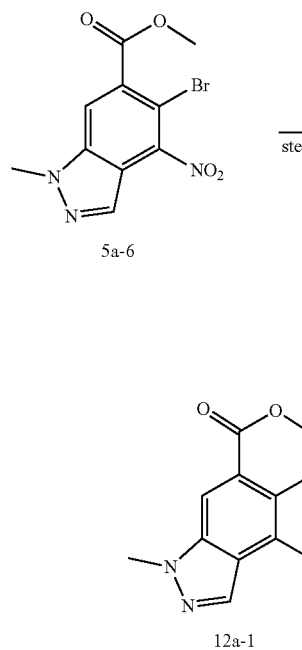

Step 1: referring to the preparation method of compound 5a-7, except that potassium trifluorovinyl borate was replaced with methyl boric acid, and sodium carbonate was replaced with barium carbonate. MS m/z (ESI): 250.3 [M+H]⁺.

Step 2: to a solution of compound 12a-1 (672 mg, 2.7 mmol) in acetic acid (20 ml) was added Selectfluor (2.86 g, 8.09 mmol) and was microwave heated at 160° C. for 30 min. The reaction was followed by LC-MS until completion. The reaction solution was filtered and the filtrate was concentrated to give compound 12a-2 (700 mg), MS m/z (ESI): 268.3 [M+H]⁺.

Step 3: to a solution of compound 12a-2 (700 mg, 2.62 mmol) in methanol (25 ml) was added iron powder (440 mg, 7.86 mmol) and acetic acid (2 ml). The reaction solution was refluxed for 4 h. The reaction was followed by LC-MS until completion. The reaction solution was filtered, and the filtrate was concentrated and purified by column chromatography to give compound 12a (350 mg, 56%). MS m/z (ESI): 238.3 [M+H]⁺.

Preparation of Intermediate 13a

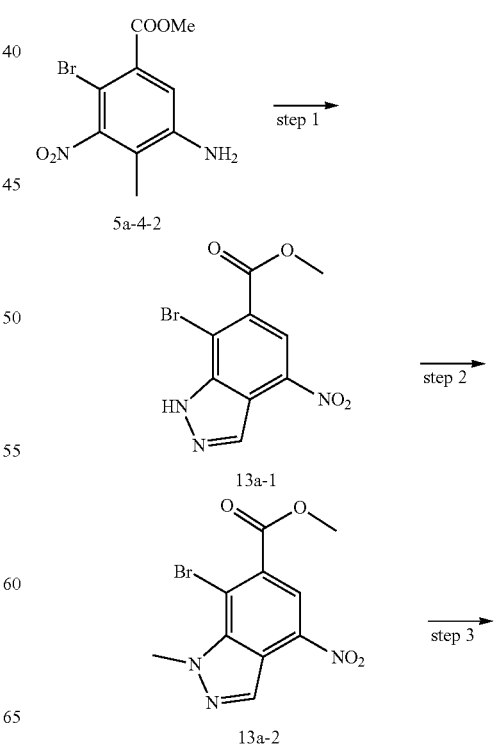

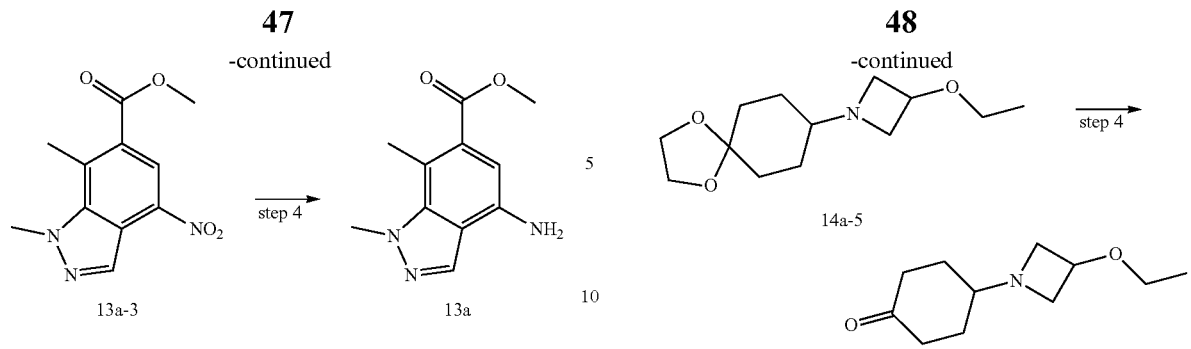

Step 1: the preparation method was the same as that of compound 3a-4, except that compound 3a-3 in the preparation method of compound 3a-4 was replaced with compound 5a-4-2. MS m/z (ESI): 299.8 [M+H]$^+$.

Step 2: the preparation method was the same as that of compound 5a-6, except that compound 5a-5 in the preparation method of compound 5a-6 was replaced with compound 13a-1. MS m/z (ESI): 316.1 [M+H]$^+$.

Step 3: to a solution of compound 13a-2 (110 mg, 0.35 mmol), trimethylcyclotriboroxane (0.15 ml, 1.05 mmol), and cesium carbonate (228 mg, 0.7 mmol) in dioxane/water (5 ml/0.2 ml) was added a catalytic amount of Pd(dppf)Cl$_2$, and the reaction was stirred under nitrogen atmosphere at 90° C. for 10 hours. The reaction was followed by LC-MS until completion. The reaction solution was filtered and the filtrate was concentrated and purified by column chromatography to give compound 13a-3 (70 mg, 83%), MS m/z (ESI): 250.2 [M+H]$^+$.

Step 4: to a solution of compound 13a-3 (70 mg, 0.28 mmol) in methanol (5 ml) was added palladium on carbon (7 mg). The mixture was stirred under hydrogen atmosphere at room temperature for 10 h. The reaction solution was filtered and the filtrate was concentrated to give compound 13a (55 mg, 90%), MS m/z (ESI): 220.1 [M+H]$^+$.

Preparation of Intermediate 14a

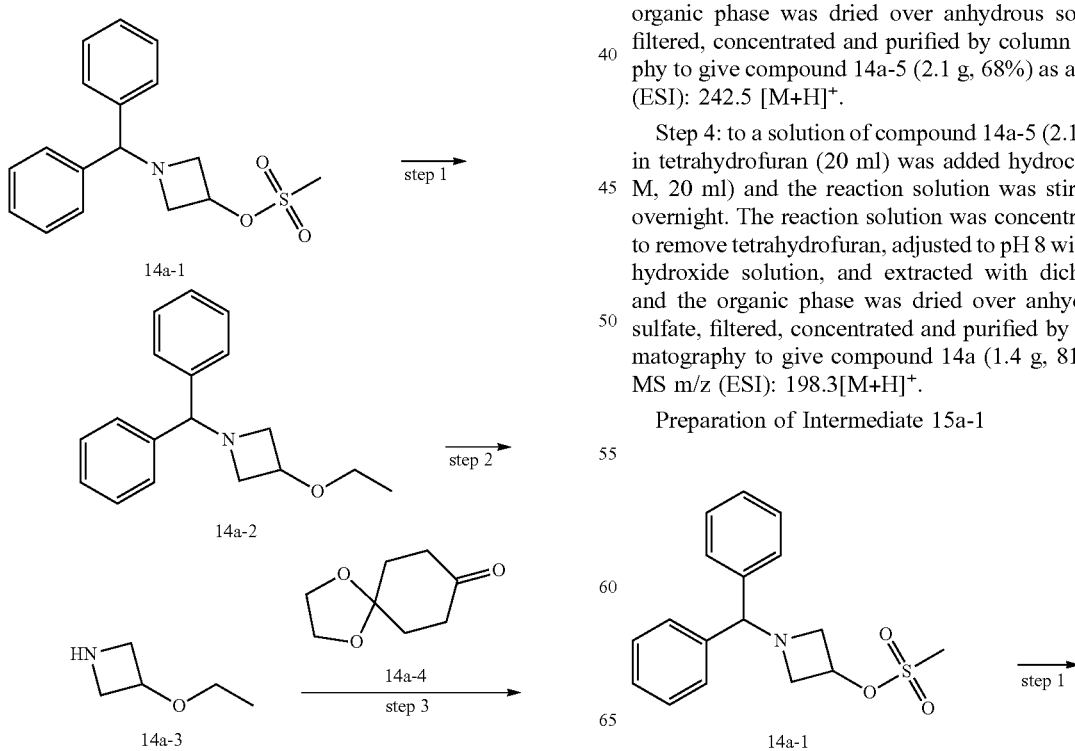

Step 1: to a solution of compound 14a-1 (2.5 g, 7.88 mmol) in ethanol (50 ml) was added sodium ethoxide (1.34 g, 19.69 mmol) and the mixture was stirred at 80° C. for 5 h. After vacuum distillation to remove part of the ethanol, the residue was poured into water and filtered. The filter cake was dried to give compound 14a-2 as a white solid (1.9 g, 90%). MS m/z (ESI): 266.5 [M+H]$^+$.

Step 2: to a solution of compound 14a-2 (1.9 g, 7.11 mmol) in methanol/acetic acid (50 ml/2.5 ml) was added palladium hydroxide (200 mg, 10%) and the mixture was stirred under hydrogen atmosphere at 50° C. for 6 h. The reaction solution was cooled to room temperature and filtered. The filtrate was concentrated to give compound 14a-3 as an oil (1.0 g).

Step 3: a solution of compound 14a-3 (3.2 g, 12.81 mmol) and compound 14a-4 (2.0 g, 12.81 mmol) in dichloromethane/acetic acid (100 ml/2 ml) was stirred at room temperature for 30 min. Sodium triacetoxyborohydride (8.14 g, 36.42 mmol) was added at 0° C. and the mixture was stirred overnight at room temperature. The reaction solution was poured into water and extracted with dichloromethane. The organic phase was dried over anhydrous sodium sulfate, filtered, concentrated and purified by column chromatography to give compound 14a-5 (2.1 g, 68%) as an oil, MS m/z (ESI): 242.5 [M+H]$^+$.

Step 4: to a solution of compound 14a-5 (2.1 g, 8.7 mmol) in tetrahydrofuran (20 ml) was added hydrochloric acid (7 M, 20 ml) and the reaction solution was stirred at 70° C. overnight. The reaction solution was concentrated in vacuo to remove tetrahydrofuran, adjusted to pH 8 with 4M sodium hydroxide solution, and extracted with dichloromethane, and the organic phase was dried over anhydrous sodium sulfate, filtered, concentrated and purified by column chromatography to give compound 14a (1.4 g, 81%) as an oil, MS m/z (ESI): 198.3[M+H]$^+$.

Preparation of Intermediate 15a-1

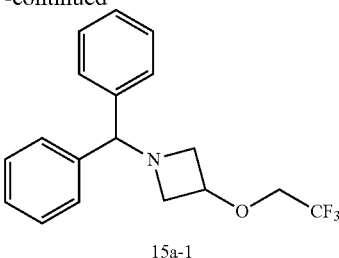

15a-1 to trifluoroethanol (20 ml) was added sodium hydride (1.13 g, 28.76 mmol) at 0° C., the mixture was stirred at 0° C. for 30 min, and compound 14a-1 (3 g, 9.45 mmol) was added to the mixture. The mixture was stirred at 80° C. for 6 h. The reaction solution was cooled to room temperature and extracted with dichloromethane. The organic phase was dried over anhydrous sodium sulfate, filtered, concentrated, and purified by column chromatography to give compound as an oil 15a-1 (2.9 g, 95%). MS m/z (ESI): 322.4 [M+H]$^+$.

Preparation of Intermediate 15a-20a

The preparation method was the same as that of intermediate 14a, compound 14a-3 was replaced with the corresponding amine.

| Compound No. | Structure |
|---|---|
| 15a | 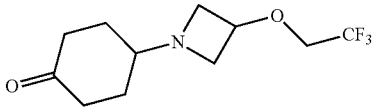 [SMILES: O=C1CCC(N2CC(OCC(F)(F)F)C2)CC1] |
| 16a | 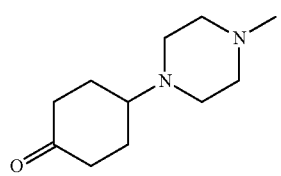 |
| 17a | 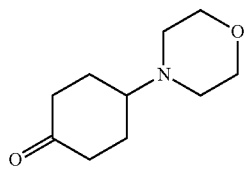 [SMILES: O=C1CCC(N2CCOCC2)CC1] |
| 18a | 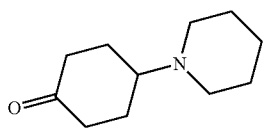 [SMILES: O=C1CCC(N2CCCCC2)CC1] |
| 19a | 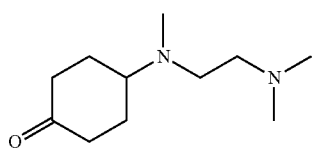 |
| 20a | 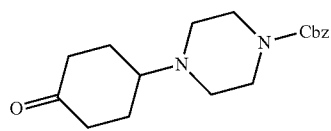 [SMILES: O=C1CCC(N2CCN(C(=O)OCc3ccccc3)CC2)CC1] |

| Compound No. | Structure |
|---|---|
| 21a | 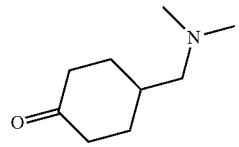 |

Preparation of Intermediate 22a

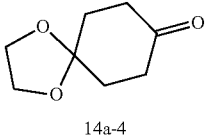

14a-4

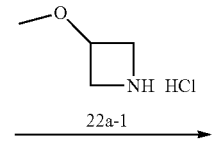

22a-1

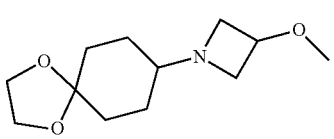

22a-2

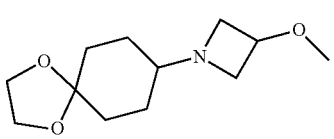

22a

Step 1: to a solution of compound 14a-4 (1.36 g, 8.71 mmol) and compound 22a-1 (900 mg, 7.26 mmol) in 1,2-dichloroethane was added sodium acetate (1.48 g, 10.9 mmol). After the reaction was stirred for 20 min at room temperature, sodium triacetoxyborohydride (4.6 g, 21.8 mmol) was added, and the reaction solution was stirred at room temperature overnight. The reaction was followed by LC-MS until completion. The reaction solution was quenched with a saturated sodium hydroxide aqueous solution, adjusted to pH 8-9, and extracted with dichloromethane. The organic phase was washed with saturated brine, dried over anhydrous sodium sulfate, filtered, and concentrated to give compound 22a-2 as a yellow solid (1.4 g, 85%), MS m/z (ESI): 228[M+H]$^+$.

Step 2: to a solution of compound 22a-2 (1.4 g, 6.2 mmol) in water (10 ml) was added trifluoroacetic acid (2 ml) and the reaction was stirred overnight at room temperature. The reaction was followed by LC-MS until completion. Saturated sodium bicarbonate solution was added to the reaction solution until the pH was 8-9, and the mixture was extracted with dichloromethane. The organic phase was washed with saturated brine, dried over anhydrous sodium sulfate, filtered, concentrated, and purified by column chromatography to give compound 22a as a yellow oil (500 mg, 44%). MS m/z (ESI): 184[M+H]$^+$.

Preparation of Compound 23a

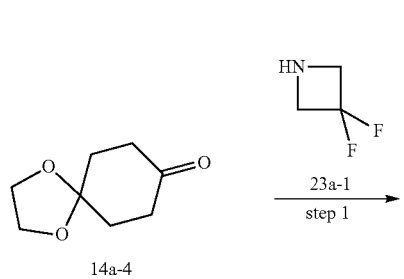

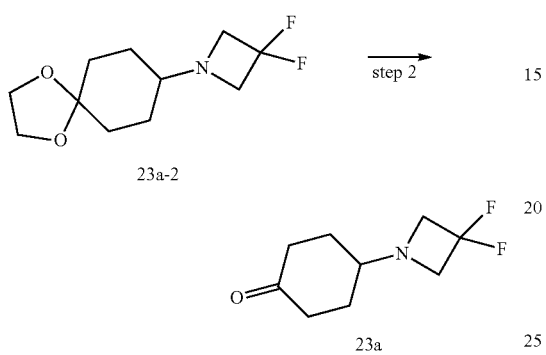

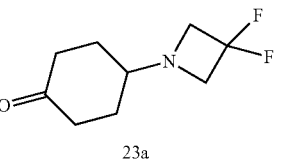

Step 1: a solution of compound 14a-4 (1 g, 6.4 mmol), compound 23a-1 (0.83 g, 6.4 mmol) and DIEA (0.82 g, 6.4 mmol) in methanol (20 ml) was stirred at room temperature for 1 h and sodium triacetoxyborohydride (2.7 g, 12.8 mmol) was added. The mixture was stirred overnight at room temperature. The reaction was followed by LC-MS until completion. The reaction was quenched with saturated sodium bicarbonate, and the pH was adjusted to 8-9. The reaction solution was extracted with dichloromethane. The organic phase was washed with saturated brine, dried over anhydrous sodium sulfate, filtered, and concentrated to give compound 23a-2 (1.1 g). MS m/z (ESI): 234 [M+H]$^+$.

Step 2: a solution of compound 23a-2 (1.1 g, 4.7 mmol) in hydrochloric acid (5 M, 20 ml) was stirred at room temperature for 16 h. The reaction was followed by TLC until completion. Saturated sodium bicarbonate solution was added to the reaction solution until pH was 8-9, and the resulting mixture was extracted with dichloromethane. The organic phase was washed with saturated brine, dried over anhydrous sodium sulfate, filtered, and concentrated to give compound 23a (300 mg).

Preparation of Intermediate 24a

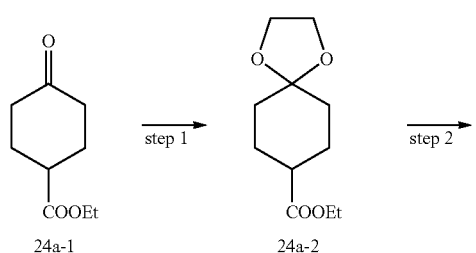

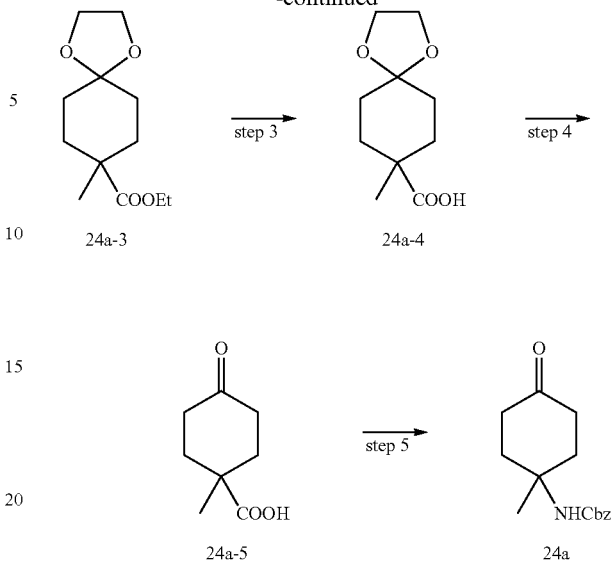

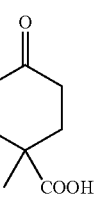

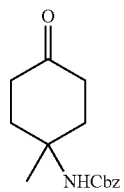

Step 1: to a solution of compound 24a-1 (8.6 g, 50.5 mmol) in toluene was added ethylene glycol (3.86 ml, 75.8 mmol) and p-toluenesulfonic acid (170 mg, 1.01 mmol), and the mixture was refluxed for 10 h to remove water. The reaction solution was concentrated and purified by column chromatography to give compound 24a-2 (5.5 g, 51%).

Step 2: to a solution of compound 24a-2 (4.05 g, 18.9 mmol) in tetrahydrofuran was added dropwise LDA (2 M, 14.1 ml) at −78° C., and the reaction solution was stirred at this temperature for 30 min before methyl iodide (2.35 ml, 37.8 mmol) was added. The reaction solution was spontaneously warmed to room temperature, and stirred for 2 h. The reaction was followed by TLC until completion. After the reaction was quenched with water, the mixture was extracted with ethyl acetate. The organic phase was washed with saturated brine and dried over sodium sulfate, filtered, concentrated, and purified by column chromatography to give compound 24a-3 (3.5 g, 72%).

Step 3: to a solution of compound 24a-3 (3.0 g, 13.1 mmol) in ethanol/water (20 ml/20 ml) was added sodium hydroxide (1.58 g, 39.4 mmol), and the mixture was stirred at 60° C. for 10 h. The reaction was followed by TLC until completion. After being cooled to room temperature, the reaction solution was adjusted to pH 3 with 1 M hydrochloric acid, and extracted with ethyl acetate. The organic phase was washed with saturated brine, dried over anhydrous sodium sulfate, filtered, and concentrated to obtain compound 24a-4 (2.5 g, 95%).

Step 4: to a solution of compound 24a-4 (2.2 g, 11 mmol) in dioxane was added hydrochloric acid (4 M, 30 ml) and the mixture was stirred at 65° C. for 3 h. After being cooled to room temperature, the reaction solution was extracted with ethyl acetate. The organic phase was washed with saturated brine, dried over anhydrous sodium sulfate, filtered, and concentrated to give compound 24a-5 (2.0 g, 100%).

Step 5: to a solution of compound 24a-5 (1 g, 6.41 mmol) in toluene was added DPPA (1.66 ml, 7.69 mmol), triethylamine (1.33 ml, 9.62 mmol) and benzyl alcohol (0.8 ml, 7.69 mmol). The reaction solution was refluxed for 10 h, and concentrated to give compound 24a (700 mg, 42%), MS m/z (ESI): 262.1 [M+H]$^+$.

Example 1: Preparation of 4-(ethyl (tetrahydro-2H-pyran-4-yl) amino)-N-((4-methoxy-6-methyl-2-oxo-1,2-dihydropyridin-3-yl)methyl)-1,5-dimethyl-1H-indazole-6-carboxamide (Compound p-1)

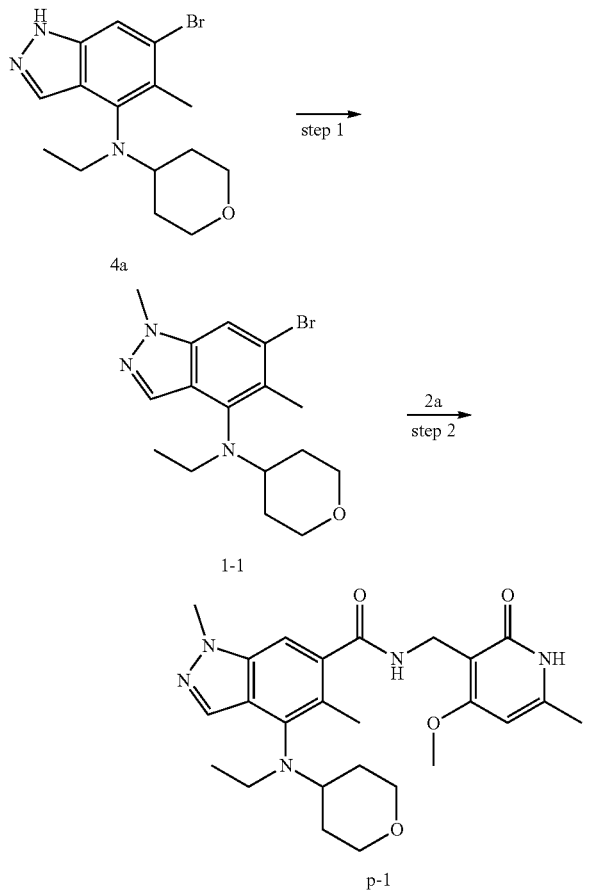

Step 1: to a solution of compound 4a (100 mg, 0.296 mmol) in 5 mL of N,N-dimethylcarboxamide was added sodium hydride (24 mg, 0.591 mmol) in an ice bath and stirred for 30 minutes in an ice bath. Methyl iodide (84 mg, 0.591 mmol) was added, and the mixture was stirred for another 2 hours. The reaction was followed by LC-MS until completion. The reaction solution was poured into water, extracted with ethyl acetate, dried, and concentrated to give 60 mg of compound 1-1. MS m/z (ESI): 354.2 [M+H]$^+$.

Step 2: a solution of compound 1-1 (50 mg, 0.14 mmol), compound 2a (50 mg, 0.21 mmol), $C_6MoO_6$ (50 mg, 0.21 mmol), Pd(dppf)Cl$_2$ (10 mg, 0.01 mmol) and triethylamine (60 mg, 0.57 mmol) in 3 mL of N,N-dimethylcarboxamide was microwaved and reacted under argon atmosphere at 140° C. for 40 min. The reaction was followed by LC-MS until completion. The reaction solution was poured into water, extracted with ethyl acetate, concentrated and purified by Prep-HPLC to give compound p-1 as a white solid (7.5 mg, 11.3%). MS m/z (ESI): 468.3[M+H]$^+$; $^1$H NMR (400 MHz, DMSO): δ 11.41 (s, 1H), 8.05 (d, 1H), 7.90 (t, 1H), 7.28 (s, 1H), 6.07 (s, 1H), 4.22 (d, 2H), 3.94 (s, 3H), 3.88-3.65 (m, 5H), 3.28-3.13 (m, 5H), 2.27 (s, 3H), 2.14 (s, 3H), 1.93-1.77 (m, 1H), 1.58-1.24 (m, 3H), 0.74 (t, 3H).

Example 2: Preparation of 4-(ethyl(tetrahydro-2H-pyran-4-yl)amino)-N-((4-methoxy-6-methyl-2-oxo-1,2-dihydropyridin-3-yl)methyl)-5-methyl-1H-indazole-6-carboxamide (Compound p-2)

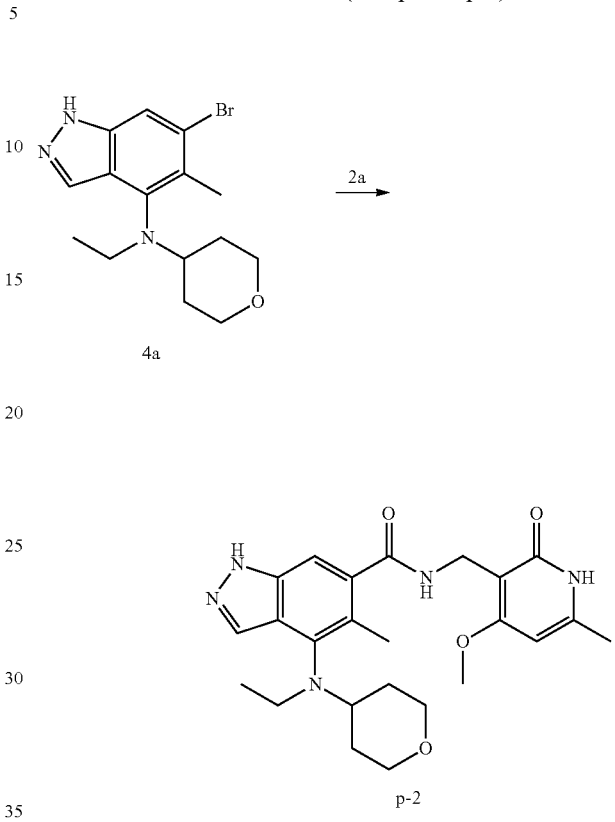

The preparation method was the same as that of compound p-1, except that compound 1-1 in the preparation method of compound p-1 was replaced with compound 4a. After purification by Prep-HPLC, compound p-2 (5 mg, 3.7%) was obtained as a white solid. MS m/z (ESI): 454.3 [M+H]$^+$; 1H NMR (400 MHz, DMSO-6) δ 12.99 (s, 1H), 11.40 (s, 1H), 8.09 (s, 1H), 7.93 (t, 1H), 7.14 (s, 1H), 6.07 (s, 1H), 4.20 (d, 2H), 3.82-3.65 (m, 5H), 3.29-3.14 (m, 5H), 2.27 (s, 3H), 2.14 (s, 3H), 1.88-1.77 (m, 1H), 1.57-1.46 (m, 1H), 1.39-1.25 (m, 2H), 0.74 (t, 3H).

Example 3: Preparation of 7-(ethyl(tetrahydro-2H-pyran-4-yl)amino)-N-((4-methoxy-6-methyl-2-oxo-1,2-dihydropyridin-3-yl)methyl)-6-methyl-1H-imidazole-5-carboxamide (Compound p-3)

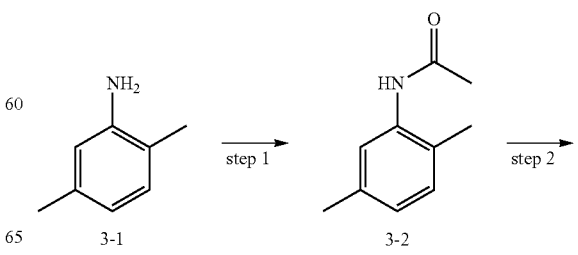

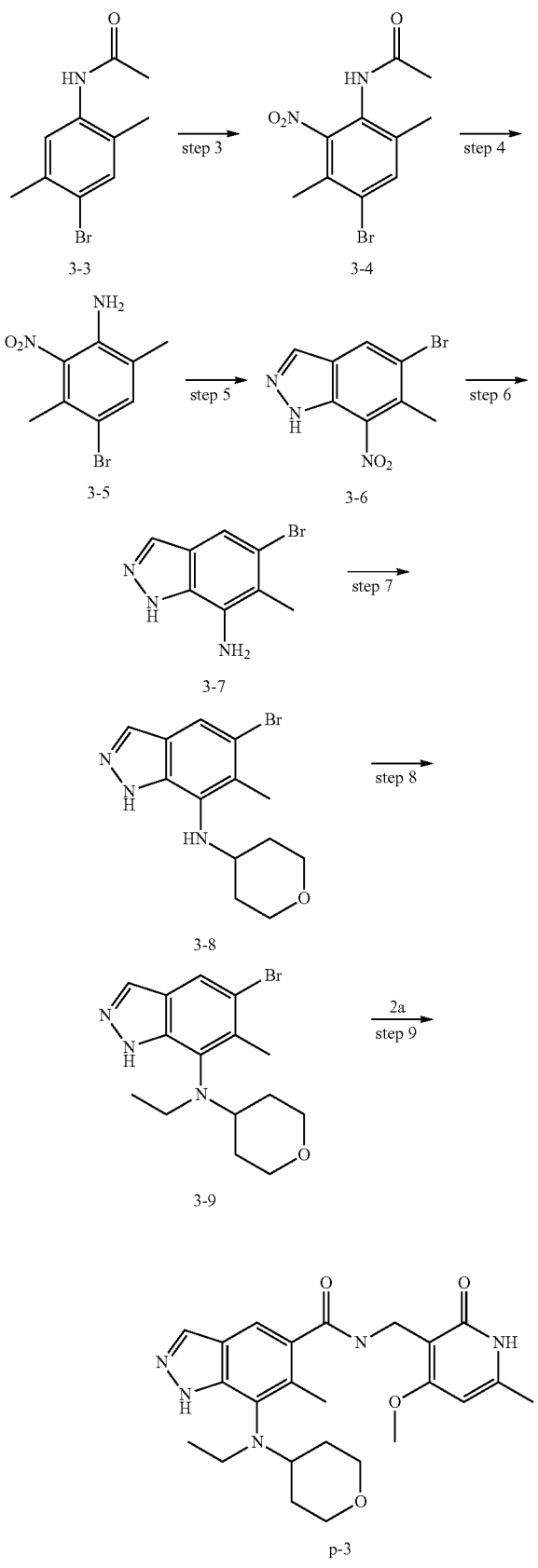

Step 1: to a solution of compound 3-1 (20 g, 0.16 mol) in 200 mL of dichloromethane was added acetic anhydride (17.7 g, 0.17 mol) and triethylamine (18.4 g, 0.18 mol) at 0° C. under argon atmosphere, and the mixture was stirred at room temperature for 2 hours. Water was added to the reaction solution, and the organic layer was separated, dried and concentrated to obtain 25.4 g compound 3-2 as a white solid. MS m/z (ESI): 164.1 [M+H]$^+$.

Step 2: to a solution of compound 3-2 (25.3 g, 0.15 mol) in 250 mL of acetic acid was added dropwise a solution of Br$_2$ (25.2 g, 0.15 mol) in 50 mL of acetic acid at 10° C. The mixture was stirred at 55° C. for 16 hours. The reaction solution was filtered. Water was added to the filtrate and the mixture was filtered. The filter cakes from the two filtrations were blended and washed with ethanol. The filter cake was dried in vacuo below 50° C. to give 32.0 g of compound 3-3 as a yellow solid. MS m/z (ESI): 242 [M+H]$^+$.

Step 3: a solution of compound 3-3 (32 g, 0.13 mol) in sulfuric acid (13.02 g, 0.13 mol) was added nitric acid (14.54 g, 0.15 mol, 61%) in an ice bath under an argon atmosphere. The mixture was stirred continuously in an ice bath for 2 hours. The reaction was followed by LC-MS until completion. The reaction solution was poured into ice water and filtered. The filter cake was washed with water and dried in vacuo below 50° C. to give 40.0 g of compound 3-4 as a solid. MS m/z (ESI): 287[M+H]$^+$.

Step 4: a solution of compound 3-4 (16 g, 35 mmol) in sulfuric acid (170 mL, 50%) was stirred at 100° C. for 6 hours. The reaction was followed by LC-MS until completion. Water was added to the reaction solution, and the mixture was filtered. The filter cake was washed with ethanol, dried in vacuo below 50° C. to give 5.0 g of compound 3-5 as a solid. MS m/z (ESI): 245 [M+H]$^+$.

Step 5: the preparation method was the same as that of compound 3a-4, except that compound 3a-3 in the preparation method of compound 3a-4 was replaced with compound 3-5. MS m/z (ESI): 256[M+H]$^+$.

Step 6: the preparation method was the same as that of compound 3a-2, except that compound 3a-1 in the preparation method of compound 3a-2 was replaced with compound 3-6. MS m/z (ESI): 228[M+H]$^+$.

Step 7: the preparation method was the same as that of compound 4a-1, except that compound 3a in the preparation method of compound 4a-1 was replaced with compound 3-7. MS m/z (ESI): 312[M+H]$^+$.

Step 8: the preparation method was the same as that of compound 4a, except that compound 4a-1 in the preparation method of compound 4a was replaced with compound 3-8. MS m/z (ESI): 312[M+H]$^+$.

Step 9: the preparation method was the same as that of compound p-1, except that compound 1-1 in the preparation method of compound p-1 was replaced with compound 3-9. After purification by Prep-HPLC, compound p-3 (4 mg, 2%) was obtained as a white solid. MS m/z (ESI): 454.3[M+H]$^+$; 1H NMR (400 MHz, DMSO-6) δ 12.81 (s, 1H), 11.39 (s, 1H), 8.41 (s, 1H), 8.00 (s, 1H), 7.83 (t, 1H), 7.43 (s, 1H), 6.07 (s, 1H), 4.20 (d, 2H), 3.93-3.61 (m, 5H), 3.29-3.10 (m, 5H), 2.37 (s, 3H), 2.15 (s, 3H), 1.83-1.80 (m, 1H), 1.47-1.44 (m, 1H), 1.29-1.23 (m, 2H), 0.74 (t, 3H).

Example 4: Preparation of 7-(ethyl(tetrahydro-2H-pyran-4-yl)amino)-N-((4-methoxy-6-methyl-2-oxo-1,2-dihydropyridin-3-yl)methyl)-1,6-dimethyl-1H-imidazole-5-carboxamide (Compound p-4)

Step 1: to a solution of compound 3-9 (150 mg, 0.443 mmol) in DMF (10 mL) was added potassium carbonate (122 mg, 0.886 mmol) and methyl iodide (125 mg, 0.886 mmol), and the mixture was stirred at room temperature overnight. The reaction was followed by LC-MS until completion. The reaction solution was poured into water, and extracted with ethyl acetate. The organic layer was concentrated and purified by combiflash to give compound 4-1 (80 mg, 51%). MS m/z (ESI): 354.2 [M+H]$^+$.

Step 2: the preparation method was the same as that of compound p-1, except that compound 1-1 in the preparation method of compound p-1 was replaced with compound 4-1. After purification by Prep-HPLC, compound p-4 (2 mg, 2%) was obtained as a white solid. MS m/z (ESI): 468.3[M+H]$^+$; $^1$H NMR (400 MHz, DMSO-6) δ 11.39 (s, 1H), 8.25 (s, 1H), 7.80 (t, 1H), 7.36 (s, 1H), 6.07 (s, 1H), 4.19 (d, 2H), 4.08 (s, 3H), 3.92-3.59 (m, 6H), 3.53-3.46 (m, 2H), 3.13-3.00 (m, 2H), 2.32 (s, 3H), 2.15 (s, 3H), 1.54-1.43 (m, 1H), 1.33-1.02 (m, 3H), 0.70 (t, 3H).

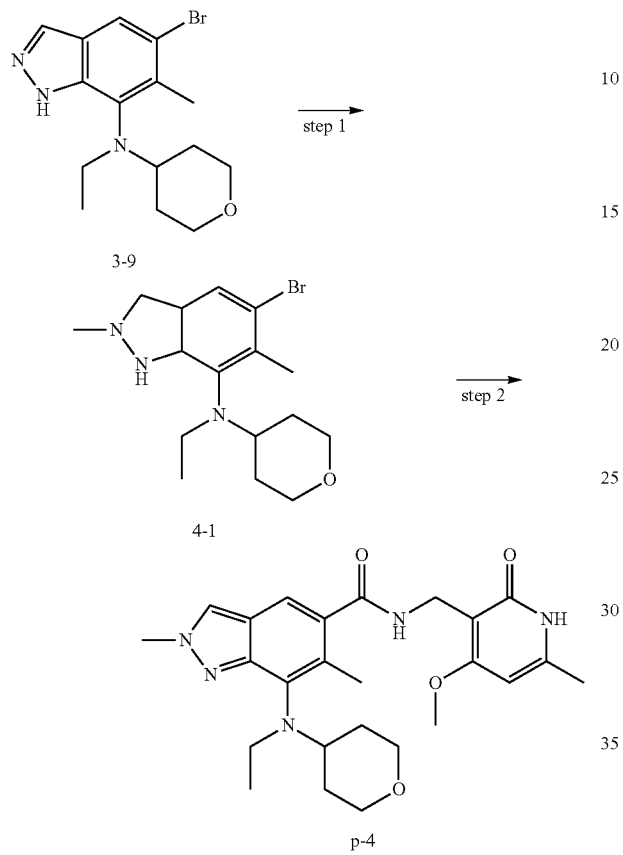

Example 5: Preparation of 1-(difluoromethyl)-4-(ethyl(tetrahydro-2H-pyran-4-yl)amino)-N-((4-methoxy-6-methyl-2-oxo-1,2-dihydropyridin-3-yl)methyl)-5-methyl-1H-indazole-6-carboxamide (Compound p-5)

Example 6: Preparation of 2-(difluoromethyl)-4-(ethyl(tetrahydro-2H-pyran-4-yl)amino)-N-((4-methoxy-6-methyl-2-oxo-1,2-dihydropyridin-3-yl)methyl)-5-methyl-2H-indazole-6-carboxamide (Compound p-6)

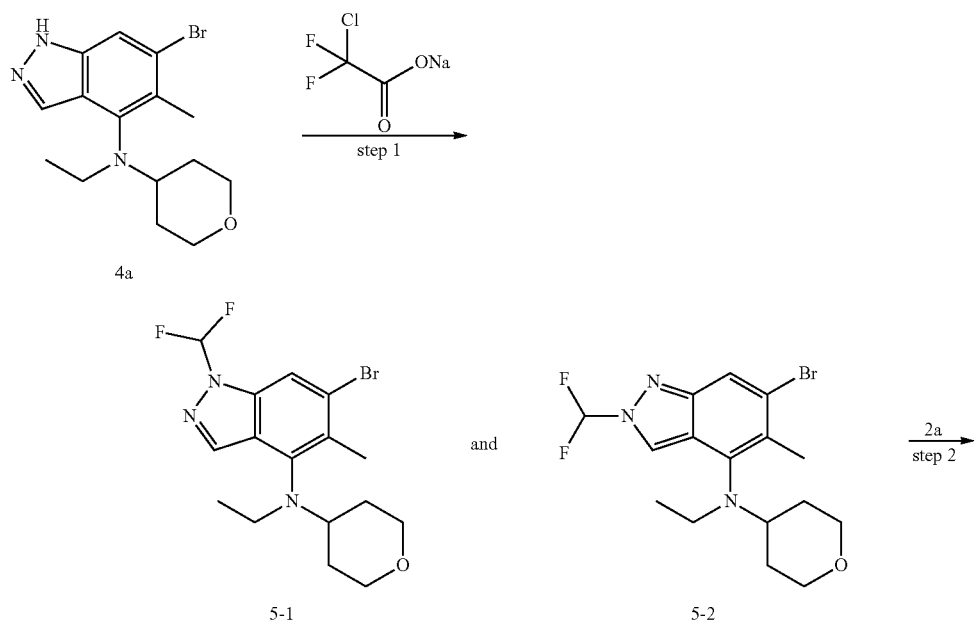

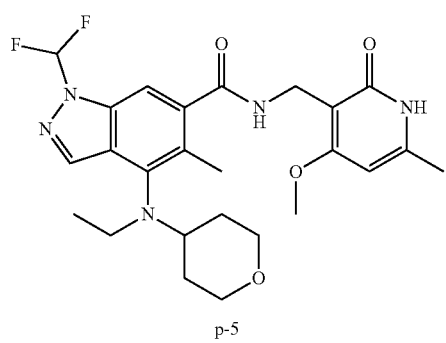

p-5

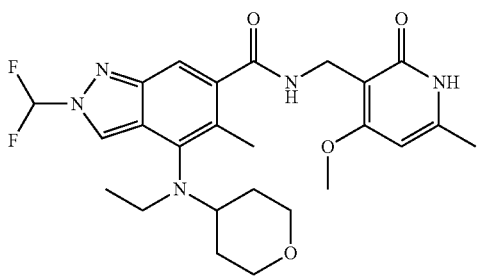

p-6 and

Step 1: the preparation method was the same as that of compound 1-1, except that compound methyl iodide in the preparation method of compound 1-1 was replaced with sodium difluorochloroacetate to give a mixture of compound 5-1 and compound 5-2. MS m/z (ESI): 388.1[M+H]$^+$.

Step 2: the preparation method was the same as that of compound p-1, except that compound 1-1 in the preparation method of compound p-1 was replaced with a mixture of compound 5-1 and compound 5-2. After purification by Prep-HPLC, compound p-5 (10 mg, 6.4%) was obtained as a white solid. $^1$H NMR (400 MHz, DMSO-6) δ 11.40 (s, 1H), 8.91 (s, 1H), 8.16-7.86 (m, 2H), 7.31 (s, 1H), 6.07 (s, 1H), 4.21 (d, 2H), 3.86-3.66 (m, 5H), 3.24-3.10 (m, 5H), 2.26 (s, 3H), 2.15 (s, 3H), 1.92-1.75 (m, 1H), 1.56-1.24 (m, 3H), 0.74 (t, 3H). compound p-6 (12 mg, 7.7%; $^1$H NMR (400 MHz, DMSO-6) δ 11.40 (s, 1H), 8.48 (s, 1H), 8.12 (t, 1H), 8.07 (t, 1H), 7.44 (s, 1H), 6.06 (s, 1H), 4.22 (d, 2H), 3.81-3.72 (m, 5H), 3.25-3.05 (m, 5H), 2.28 (s, 3H), 2.14 (s, 3H), 1.87-1.70 (m, 1H), 1.54-1.27 (m, 3H), 0.76 (t, 3H). MS m/z (ESI): 504[M+H]$^+$.

Example 50: Preparation of 4-(ethyl(tetrahydro-2H-pyran-4-yl)amino)-N-((4-methoxy-6-methyl-2-oxo-1,2-dihydropyridin-3-yl)methyl)-2,5dimethyl-2H-indazole-6-carboxamide (Compound p-50)

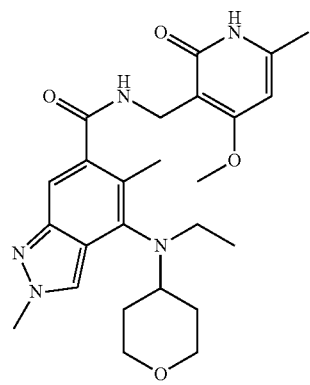

P-50

The preparation method was the same as that of compound P-6, wherein step 1 refers to the preparation of compound 1-1. MS m/z (ESI): 468.2[M+H]$^+$.

Example 7: Preparation of N-((4,6-dimethyl-2-oxo-1,2-dihydropyridin-3-yl) methyl)-4-(ethyl(tetrahydro-2H-pyran-4-yl)amino)-1,5-dimethyl-1H-indazole-6-carboxamide (Compound p-7)

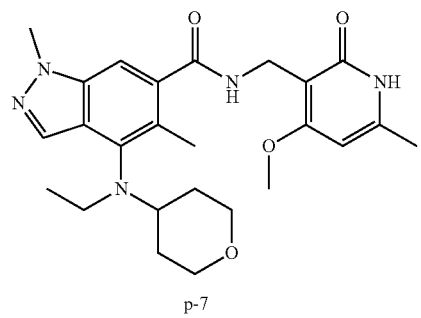

p-7

The preparation method was the same as that of compound p-1, except that compound 2a in the preparation method of compound p-1 was replaced with compound 1a. After purification by Prep-HPLC, compound p-7 (9 mg, 7.8%) was obtained as a white solid. MS m/z (ESI): 452 [M+H]$^+$; $^1$H NMR (400 MHz, DMSO-6) δ 11.44 (s, 1H), 8.10 (t, 1H), 8.06 (s, 1H), 7.29 (s, 1H), 5.84 (s, 1H), 4.27 (d, 2H), 3.95 (s, 3H), 3.85-3.65 (m, 2H), 3.28-3.00 (m, 5H), 2.26 (s, 3H), 2.20 (s, 3H), 2.08 (s, 3H), 1.93-1.73 (m, 1H), 1.56-1.24 (m, 3H), 0.74 (t, 3H).

Example 8: Preparation of N-((4,6-dimethyl-2-oxo-1,2-dihydropyridin-3-yl) methyl)-4-(ethyl(1-(2, 2, 2-trifluoroethyl) piperidin-4-yl) amino)-1,5-dimethyl-1H-indazole-6-carboxamide (Compound p-8)

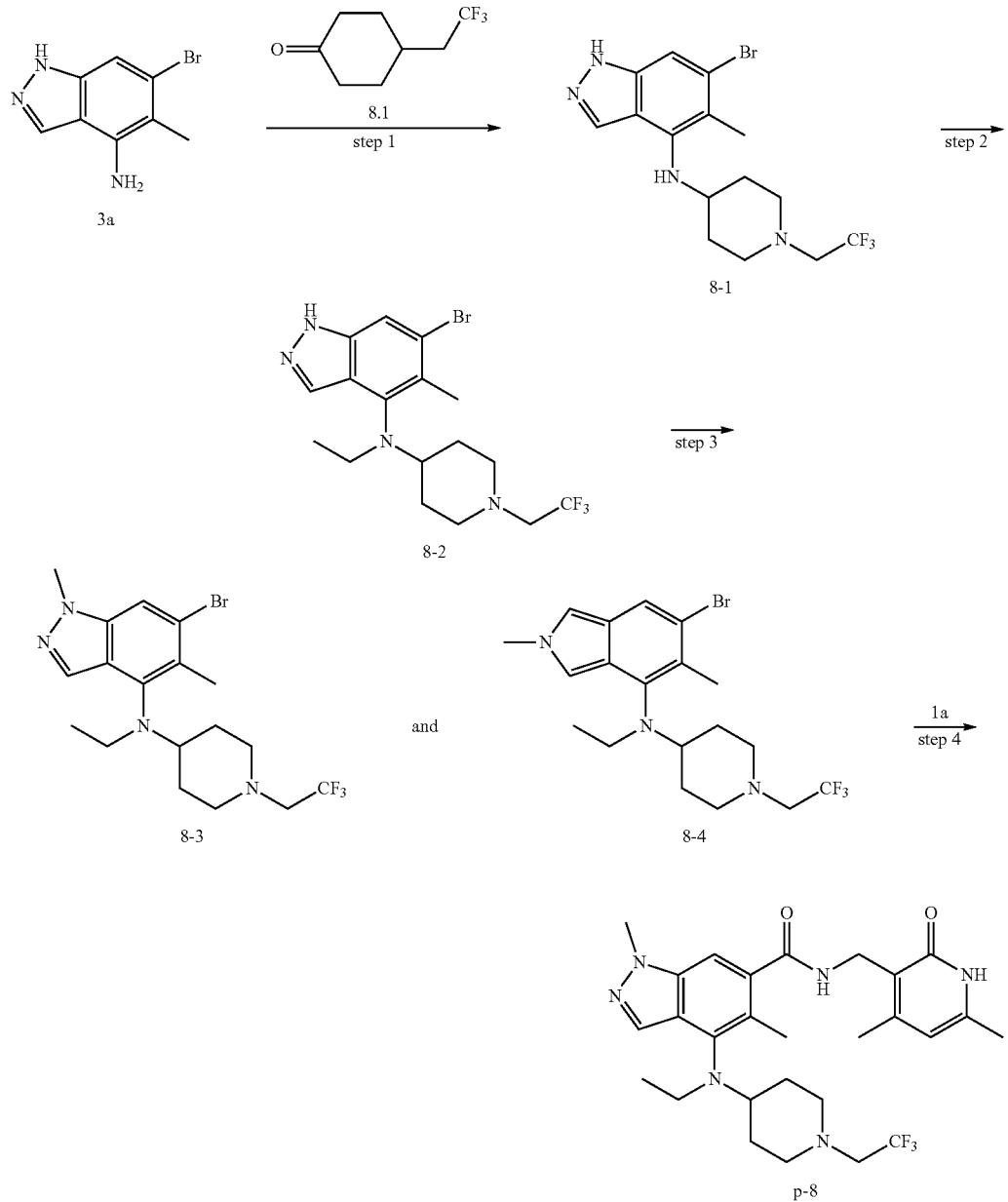

Step 1: the preparation method was the same as that of compound 4a-1, except that tetrahydropyrone in the preparation method of compound 4a-1 was replaced with compound 8.1. MS m/z (ESI): 390[M+H]⁺.

Step 2: the preparation method was the same as that of compound 4a, except that compound 4a-1 in the preparation method of compound 4a was replaced with compound 8-1. MS m/z (ESI): 418 [M+H]⁺.

Step 3: the preparation method was the same as that of compound 1-1, except that compound 4a in the preparation method of compound 1-1 was replaced with compound 8-2. MS m/z (ESI): 434.9[M+H]⁺.

Step 4: the preparation method was the same as that of compound p-1, except that compound 1-1 and compound 2a in the preparation method of compound p-1 were replaced with compound 8-3 & 8-4 and 1a. After purification by Prep-HPLC, compound p-8 (8 mg, 8%) was obtained as a white solid. MS m/z (ESI): 533[M+H]⁺; $^1$H NMR (400 MHz, DMSO-6) δ 11.47 (s, 1H), 8.13 (t, 1H), 8.09 (s, 1H), 7.33 (s, 1H), 5.85 (s, 1H), 4.29 (d, 2H), 3.99-3.94 (m, 5H), 3.43-3.11 (m, 5H), 3.05-2.91 (m, 2H), 2.27 (s, 3H), 2.21 (s, 3H), 2.09 (s, 3H), 1.74-1.57 (m, 2H), 1.52-1.36 (m, 2H), 0.75 (t, 3H).

Example 9: Preparation of N-((4,6-dimethyl-2-oxo-1,2-dihydropyridin-3-yl) methyl)-4-(ethyl (4-((2-methoxyethyl)(methyl) amino) cyclohexyl)amino)-1,5-dimethyl-1H-indazole-6-carboxamide (Compound p-9)

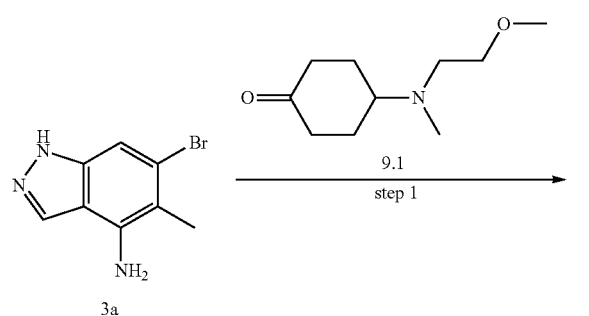

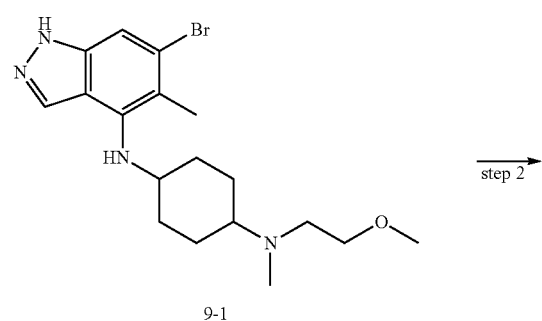

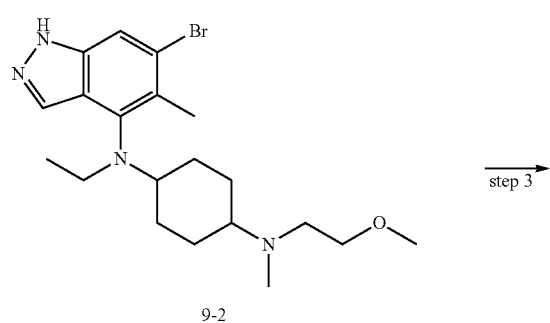

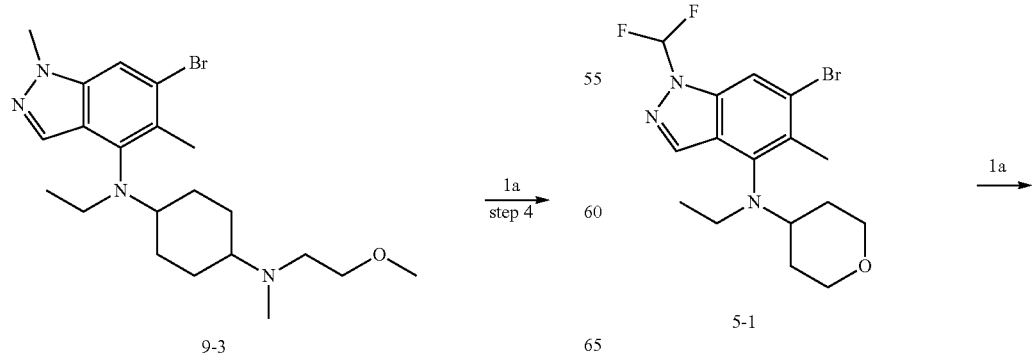

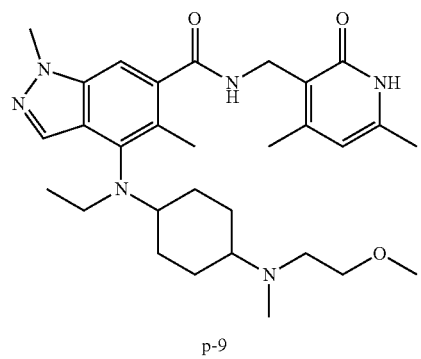

Step 1: the preparation method was the same as that of compound 4a-1, except that tetrahydropyrone in the preparation method of compound 4a-1 was replaced with compound 9.1. MS m/z (ESI): 390[M+H]⁺.

Step 2: the preparation method was the same as that of compound 4a, except that compound 4a-1 in the preparation method of compound 4a was replaced with compound 9-1. MS m/z (ESI): 418[M+H]⁺.

Step 3: the preparation method was the same as that of compound 1-1, except that compound 4a in the preparation method of compound 1-1 was replaced with compound 9-2. MS m/z (ESI): 434.9[M+H]⁺.

Step 4: the preparation method was the same as that of compound p-1, except that compound 1-1 and compound 2a in the preparation method of compound p-1 were replaced with compound 9-3 and compound 1a. After purification by Prep-HPLC, compound p-9 (4 mg, 3.6%) was obtained as a white solid. MS m/z (ESI): 537.1[M+H]⁺; ¹H NMR (400 MHz, DMSO-6) δ 11.44 (s, 1H), 8.09 (t, 1H), 8.02 (s, 1H), 7.26 (s, 1H), 5.84 (s, 1H), 4.28 (d, 2H), 3.95 (s, 3H), 3.29-3.27 (m, 4H), 3.17 (s, 3H), 2.94-2.85 (m, 1H), 2.45-2.41 (m, 2H), 2.24 (s, 3H), 2.20 (s, 3H), 2.10 (s, 3H), 2.08 (s, 3H), 1.70-1.54 (m, 3H), 1.35-1.05 (m, 5H), 0.73 (t, 3H).

Example 10: Preparation of 1-(difluoromethyl)-N-((4,6-dimethyl-2-oxo-1,2-dihydropyridin-3-yl) methyl)-4-(ethyl(tetrahydro-2H-pyran-4-yl)amino)-5-methyl-1H-indazole-6-carboxamide (Compound p-10)

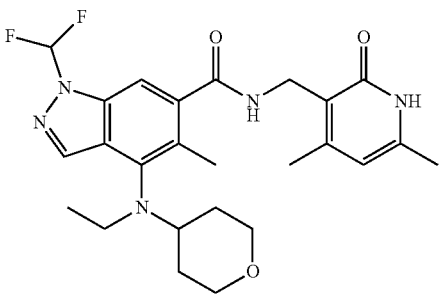

p-10

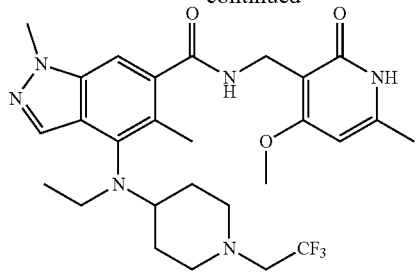

p-11

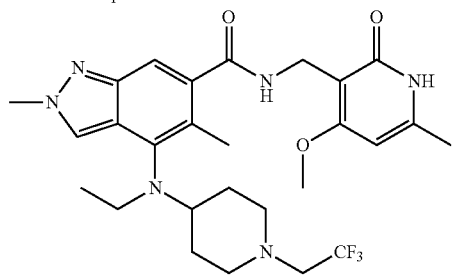

p-12

The preparation method was the same as that of compound p-1, except that compound 1-1 and compound 2a in the preparation method of compound p-1 were replaced with compound 5-1 and compound 1a. After purification by Prep-HPLC, compound p-10 (16 mg, 16%) was obtained as a white solid. MS m/z (ESI): 488[M+H]$^+$; $^1$H NMR (400 MHz, DMSO-6) δ 11.47 (s, 1H), 8.50 (s, 1H), 8.31 (t, 1H), 8.14 (t, 1H), 7.46 (s, 1H), 5.85 (s, 1H), 4.28 (d, 2H), 3.85-3.69 (m, 2H), 3.39-3.11 (m, 5H), 2.28 (s, 3H), 2.20 (s, 3H), 2.09 (s, 3H), 1.59-1.22 (s, 4H), 0.77 (t, 3H).

Example 11: Preparation of 4-(ethyl(1-(2, 2, 2-trifluoroethyl)piperidin-4-yl)amino)-N-((4-methoxy-6-methyl-2-oxo-1,2-dihydropyridin-3-yl)methyl)-1,5-dimethyl-1H-indazole-6-carboxamide (Compound p-11)

Example 12: Preparation of 4-(ethyl(1-(2, 2, 2-trifluoroethyl)piperidin-4-yl)amino)-N-((4-methoxy-6-methyl-2-oxo-1,2-dihydropyridin-3-yl)methyl)-2,5-dimethyl-2H-indazole-6-carboxamide (Compound p-12)

The preparation method was the same as that of compound p-1, except that compound 1-1 in the preparation method of compound p-1 was replaced with a mixture of compound 8-3 and compound 8-4. After purification by Prep-HPLC, compound p-11 (9 mg, 12%) was obtained as a white solid; $^1$H NMR (400 MHz, DMSO-6) δ 11.41 (s, 1H), 8.04 (s, 1H), 7.90 (t, 1H), 7.28 (s, 1H), 6.07 (s, 1H), 4.23 (d, 2H), 3.95 (s, 3H), 3.79 (s, 3H), 3.29-2.51 (m, 9H), 2.27 (s, 3H), 2.15 (s, 3H), 1.90-1.73 (m, 1H), 1.56-1.31 (m, 3H), 0.74 (t, 3H). p-12 (3 mg, 4%); $^1$H NMR (400 MHz, DMSO-6) δ 11.40 (s, 1H), 8.39 (s, 1H), 7.89 (t, 1H), 7.22 (s, 1H), 6.07 (s, 1H), 4.20 (d, 2H), 4.09 (s, 3H), 3.79 (s, 3H), 3.24-2.64 (m, 9H), 2.25 (s, 3H), 2.15 (s, 3H), 1.92-1.83 (m, 1H), 1.62-1.50 (m, 1H), 1.38-1.21 (m, 2H), 0.72 (t, 3H). MS m/z (ESI): 549[M+H]$^+$.

Example 13: Preparation of N-((4,6-dimethyl-2-oxo-1,2-dihydropyridin-3-yl)methyl)-4-(((1S, 4S)-4-(dimethylamino)cyclohexyl)(ethyl)amino)-1,5-dimethyl-1H-indazole-6-carboxamide (Compound p-13)

Example 14: Preparation of N-((4,6-dimethyl-2-oxo-1,2-dihydropyridin-3-yl)methyl)-4-(((1R, 4R)-4-(dimethylamino)cyclohexyl)(ethyl)amino)-1,5-dimethyl-1H-indazole-6-carboxamide (Compound p-14)

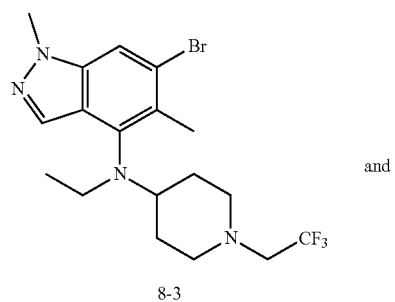

8-3

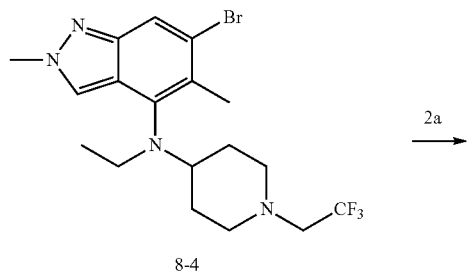

8-4

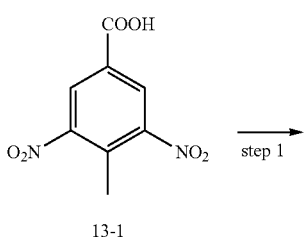

13-1

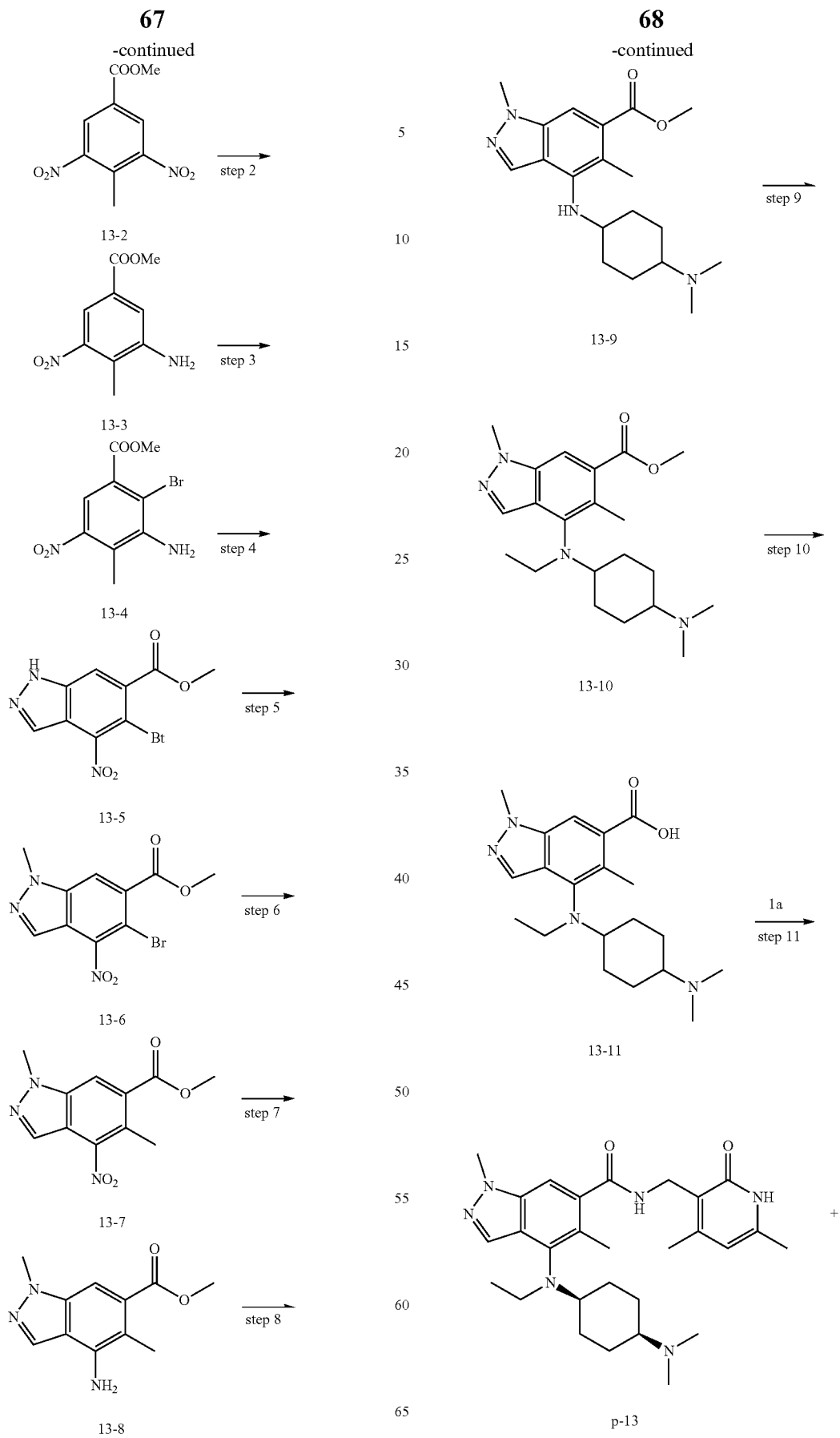

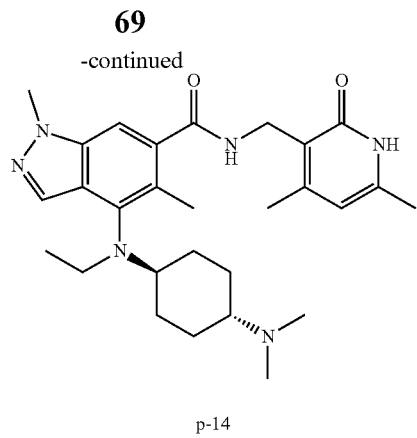

p-14

Step 1: to a solution of compound 13-1 (8 g, 35.3 mmol) in anhydrous methanol (100 mL) was added thionyl chloride (7.7 mL, 106.1 mmol). The mixture was stirred under reflux at room temperature for 20 hours. The reaction was followed by TLC until completion. The reaction solution was cooled and concentrated to remove most of the solvent. After filtration, the filter cake was dried in vacuo to give 7.5 g of compound 13-2. MS m/z (ESI): 241 [M+H]$^+$.

Step 2: to a solution of compound 13-2 (7.6 g, 31.64 mmol) in acetic acid (150 mL) was added iron powder (14 g, 253 mmol) in batchs. After the addition, the reaction solution was filtered. The filtrate was poured into water and extracted with ethyl acetate. The organic layer was concentrated, and purified by combiflash to give compound 13-3 as a yellow solid (3.5 g, 52.6%). MS m/z (ESI): 211 [M+H]$^+$.

Step 3: to a solution of compound 13-3 (1 g, 4.76 mmol) in DMSO (20 mL) was added dropwise a solution of NBS (931 mg, 5.23 mmol) in DMSO (1.5 mL), and the mixture was stirred at room temperature for 2 hours. The reaction was followed by LC-MS until completion. The reaction solution was poured into water and filtered. The filter cake was dried in vacuo to give 700 mg of compound 13-4 as a yellow solid. MS m/z (ESI): 290.8 [M+H]$^+$.

Step 4: the preparation method was the same as that of compound 3a-4, except that compound 3a-3 in the preparation method of compound 3a-4 was replaced with compound 13-4. MS m/z (ESI): 299.8 [M+H]$^+$.

Step 5: the preparation method was the same as that of compound 1-1, except that compound 4a in the preparation method of compound 1-1 was replaced with compound 13-5. MS m/z (ESI): 315.8[M+H]$^+$.

Step 6: a mixture of compound 13-6 (900 mg, 2.87 mmol), methyl boric acid (343 mg, 5.73 mmol), Pd(dppf)Cl$_2$ (210 mg, 0.286 mmol), sodium carbonate (607 mg, 5.73 mmol), 1, 4-dioxane (20 mL) and 2 mL of water was microwaved and reacted at 100° C. under an argon atmosphere for 8 hours. The reaction was followed by LC-MS until completion. The reaction solution was poured into water, extracted with ethyl acetate, concentrated, and purified by combiflash to give compound 13-7 as a yellow solid (300 mg, 20%). MS m/z (ESI): 249.9 [M+H]$^+$.

Step 7: the preparation method was the same as that of compound 13-3, except that compound 13-2 in the preparation method of compound 13-3 was replaced with compound 13-7, and the mixture was heated to 90° C. and stirred for 7 hours. MS m/z (ESI): 220[M+H]$^+$.

Step 8: the preparation method was the same as that of compound 4a-1, except that tetrahydropyrone in the preparation method of compound 4a-1 was replaced with 4-dimethyl aminocyclohexanone. MS m/z (ESI): 345.1[M+H]$^+$.

Step 9: the preparation method was the same as that of compound 4a, except that compound 4a-1 in the preparation method of compound 4a was replaced with compound 13-9. MS m/z (ESI): 373.1[M+H]$^+$.

Step 10: to a solution of compound 13-10 (270 mg, 0.724 mmol) in THF (10 mL) was added methanol (4 mL) and sodium hydroxide (4 mL, 3M), and the mixture was stirred at room temperature overnight. The reaction was followed by LC-MS until completion. The reaction solution was adjusted to pH 6, and extracted with ethyl acetate for removal of impurity. The aqueous layer was concentrated. The residue was washed with DCM:MeOH=10:1. After filtration, the filtrate was concentrated to give 200 mg of compound 13-11. MS m/z (ESI): 357.3[M+H]$^+$.

Step 11: to a solution of compound 13-11 (80 mg, 0.223 mmol) in DMF (3 mL) was added HATU (127 mg, 0.335 mmol), DIPEA (115 mg, 0.892 mmol) and compound 1a (84 mg, 0.446 mmol). The mixture was stirred at room temperature overnight. The reaction was followed by LC-MS until completion. The reaction solution was extracted with ethyl acetate/water and the organic layer was concentrated and purified by combiflash to give compound p-13 as a white solid (3 mg, 2.7%); 1H NMR (400 MHz, DMSO) δ 11.46 (s, 1H), 8.12 (t, 1H), 8.03 (s, 1H), 7.26 (s, 1H), 5.83 (s, 1H), 4.26 (d, 2H), 3.93 (s, 3H), 3.57 (s, 1H), 3.18-2.98 (m, 3H), 2.28-2.18 (m, 12H), 2.07 (s, 3H), 1.71 (s, 2H), 1.41-1.19 (m, 6H), 0.77 (t, 3H)*D p-14 (9 mg, 8%). MS m/z (ESI): 493.4[M+H]$^+$; $^1$H NMR (400 MHz, DMSO-6) δ 11.44 (s, 1H), 8.09 (t, 1H), 8.02 (s, 1H), 7.26 (s, 1H), 5.84 (s, 1H), 4.28 (d, 2H), 3.95 (s, 3H), 3.28-3.03 (m, 2H), 2.95-2.84 (m, 2H), 2.28 (s, 3H), 2.20 (s, 3H), 2.15-1.99 (m, 9H), 1.74-1.64 (m, 4H), 1.34-1.20 (m, 2H), 1.12-0.99 (m, 2H), 0.73 (t, 3H).

Example 15: Preparation of 4-(ethyl(4-((2-methoxyethyl) (methyl)amino)cyclohexyl)amino)-N-((4-methoxy-6-methyl-2-oxo-1,2-dihydropyridin-3-yl) methyl)-1,5-dimethyl-1H-indazole-6-carb oxamide (Compound p-15)

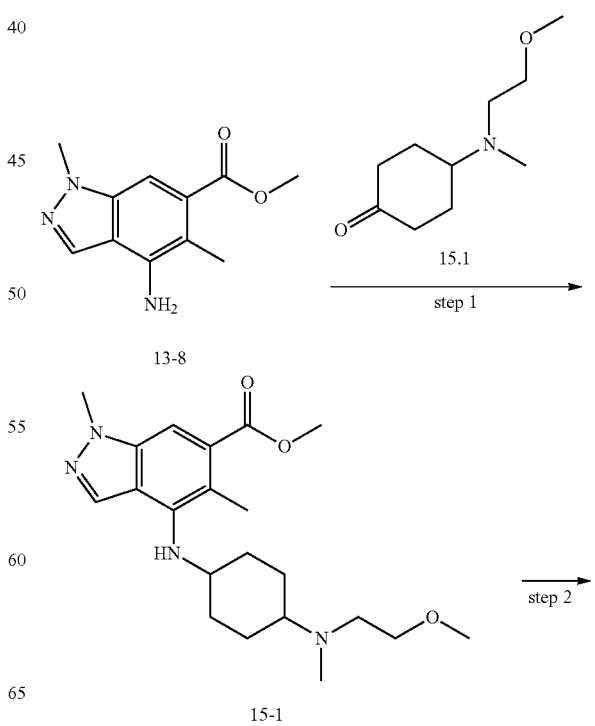

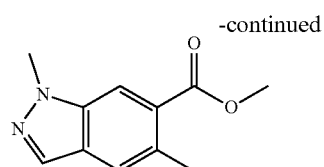

15-2

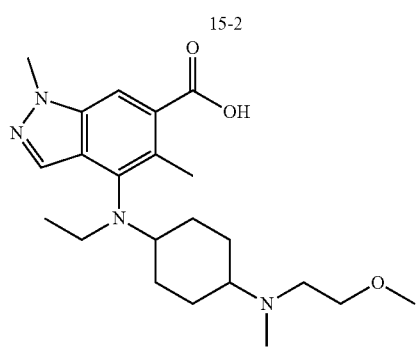

15-3

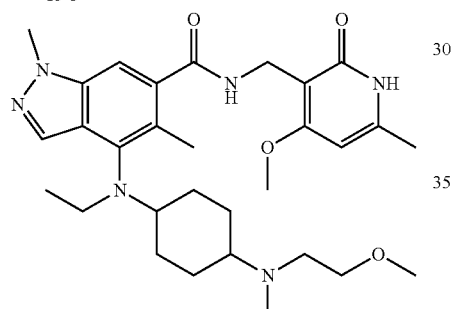

p-15

Step 1: the preparation method was the same as that of compound 4a-1, except that tetrahydropyrone in the preparation method of compound 4a-1 was replaced with compound 15.1. MS m/z (ESI): 389.1[M+H]⁺.

Step 2: the preparation method was the same as that of compound 4a, except that compound 4a-1 in the preparation method of compound 4a was replaced with compound 15-1. MS m/z (ESI): 417.4[M+H]⁺.

Step 3: the preparation method was the same as that of compound 13-11, except that compound 13-10 in the preparation method of compound 13-11 was replaced with compound 15-2. MS m/z (ESI): 403.4[M+H]⁺.

Step 4: the preparation method was the same as that of compound p-13, except that compound 13-11 in the preparation method of compound p-13 was replaced with compound 15-3. After purification by Prep-HPLC, compound p-15 (25 mg, 10%) was obtained as a white solid. MS m/z (ESI): 553.3[M+H]⁺; ¹H NMR (400 MHz, DMSO-6) 611.39 (s, 1H), 8.02 (s, 1H), 7.88 (t, 1H), 7.25 (s, 1H), 6.07 (s, 1H), 4.23 (d, 2H), 3.97 (s, 3H), 3.79 (s, 3H), 3.51-3.41 (m, 2H), 3.29-3.27 (m, 2H), 3.20-3.15 (m, 4H), 2.94-2.84 (m, 1H), 2.46-2.43 (m, 2H), 2.24 (s, 3H), 2.15 (s, 3H), 2.10 (s, 3H), 1.72-1.57 (m, 3H), 1.33-1.07 (m, 5H), 0.73 (t, 3H).

Example 16: Preparation of 5-ethyl-4-(ethyl(tetrahydro-2H-pyran-4-yl) amino)-N-((4-methoxy-6-methyl-2-oxo-1,2-dihydropyridin-3-yl)methyl)-1-methyl-1H-indazole-6-carboxamide (Compound p-16)

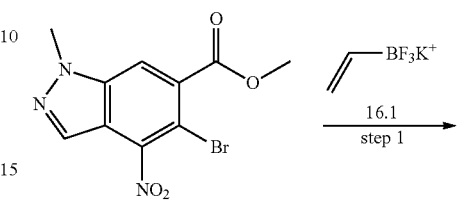

13-6

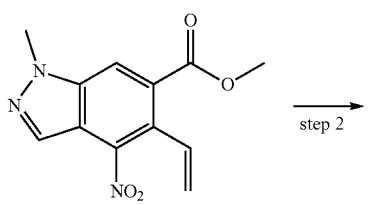

16-1

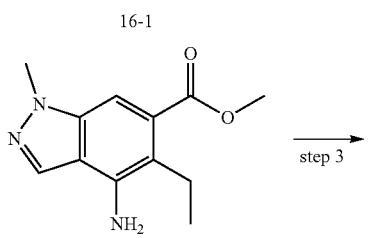

16-2

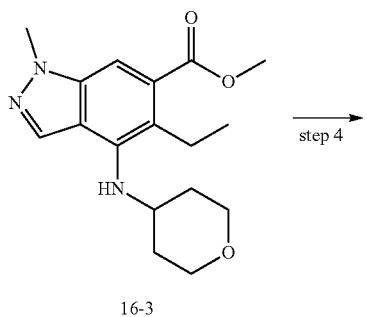

16-3

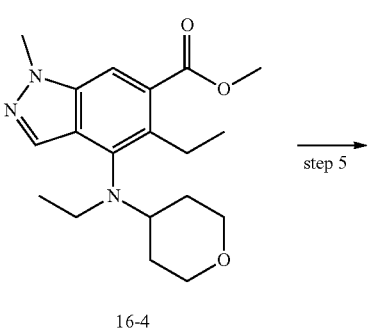

16-4

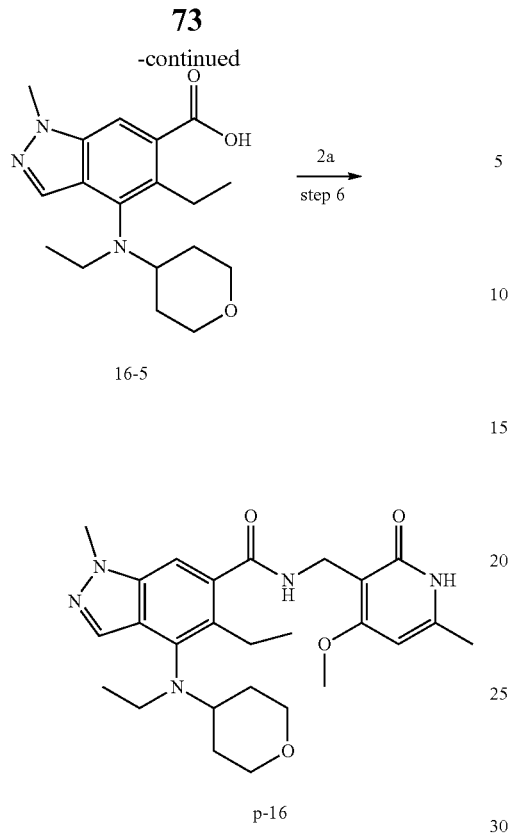

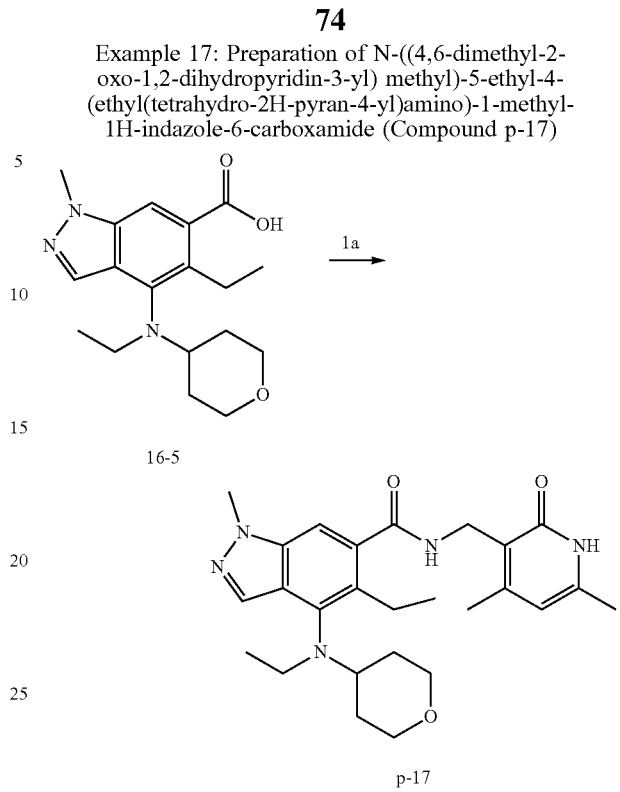

Example 17: Preparation of N-((4,6-dimethyl-2-oxo-1,2-dihydropyridin-3-yl) methyl)-5-ethyl-4-(ethyl(tetrahydro-2H-pyran-4-yl)amino)-1-methyl-1H-indazole-6-carboxamide (Compound p-17)

Step 1: the preparation method was the same as that of compound 13-7, except that methyl boronic acid in the preparation method of compound 13-7 was replaced with compound 16.1. MS m/z (ESI): 262.1 [M+H]+.

Step 2: to a solution of compound 16-1 (50 mg, 0.2 mmol) in methanol (5 mL) and 1 mL of tetrahydrofuran was added palladium on carbon (15 mg) and the mixture was stirred under hydrogen atmosphere at room temperature overnight. The reaction was followed by LC-MS until completion. The reaction solution was filtered and concentrated to give compound 16-2. MS m/z (ESI): 234.2 [M+H]+.

Step 3: the preparation method was the same as that of compound 4a-1, except that compound 3a in the preparation method of compound 4a-1 was replaced with compound 16-2. MS m/z (ESI): 318.2[M+H]+.

Step 4: the preparation method was the same as that of compound 4a, except that compound 4a-1 in the preparation method of compound 4a was replaced with compound 16-3. MS m/z (ESI): 346.2[M+H]+.

Step 5: the preparation method was the same as that of compound 13-11, except that compound 13-10 in the preparation method of compound 13-11 was replaced with compound 16-4. MS m/z (ESI): 332.2[M+H]+.

Step 6: the preparation method was the same as that of compound p-13, except that compound 13-11 in the preparation method of compound p-13 was replaced with compound 16-5. After purification by Prep-HPLC, compound p-16 (46 mg, 16%) was obtained as a white solid. MS m/z (ESI): 482.2[M+H]+; $^1$H NMR (400 MHz, DMSO) δ11.41 (s, 1H), 8.07 (s, 1H), 7.92 (t, 1H), 7.31 (s, 1H), 6.07 (s, 1H), 4.26 (d, 2H), 3.95 (s, 3H), 3.83-3.71 (m, 2H), 3.78 (s, 3H), 3.24-3.18 (m, 5H), 2.96-2.92 (m, 2H), 2.17 (s, 3H), 1.85 (s, 1H), 1.55 (s, 1H), 1.38-1.29 (m, 2H), 0.99 (t, 3H), 0.77 (t, 3H).

The preparation method was the same as that of compound p-13, except that compound 13-11 and compound 2a in the preparation method of compound p-13 were replaced with compound 16-5 and compound 1a. After purification by Prep-HPLC, compound p-17 (52 mg, 19%) was obtained as a white solid. MS m/z (ESI): 466.2[M+H]+; $^1$H NMR (400 MHz, DMSO) δ 11.44 (s, 1H), 8.10 (t, 1H), 8.07 (s, 1H), 7.30 (s, 1H), 5.84 (s, 1H), 4.27 (d, 2H), 3.93 (s, 3H), 3.82-3.70 (m, 2H), 3.23-3.12 (m, 5H), 2.95-2.92 (m, 2H), 2.21 (s, 3H), 2.08 (s, 3H), 1.88 (s, 1H), 1.52 (s, 1H), 1.32-1.27 (m, 2H), 0.94 (t, 3H), 0.77 (t, 3H).

Example 18: Preparation of N-((4,6-dimethyl-2-oxo-1,2-dihydropyridin-3-yl)methyl)-5-ethyl-4-(ethyl((1S,4S)-4-(3-methylazetiazin-1-yl) cyclohexyl)amino)-1-methyl-1H-indazole-6-carboxamide (Compound p-18)

Example 19: Preparation of N-((4,6-dimethyl-2-oxo-1,2-dihydropyridin-3-yl) methyl)-5-ethyl-4-(ethyl((1R, 4R)-4-(3-methylazetiazin-1-yl) cyclohexyl)amino)-1-methyl-1H-indazole-6-carboxamide (Compound p-19)

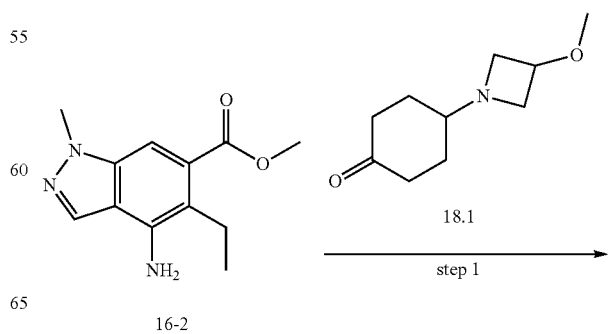

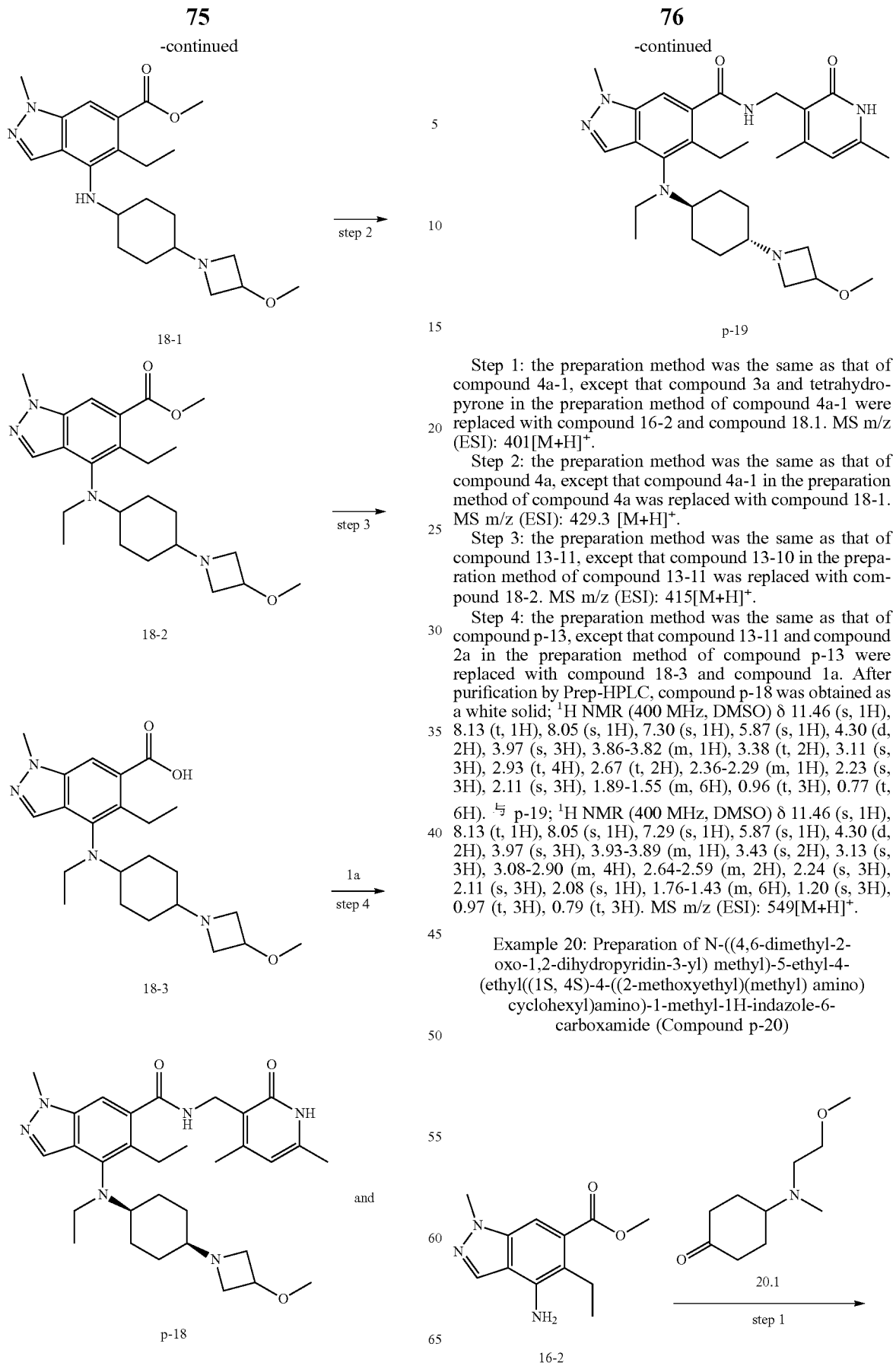

Step 1: the preparation method was the same as that of compound 4a-1, except that compound 3a and tetrahydropyrone in the preparation method of compound 4a-1 were replaced with compound 16-2 and compound 18.1. MS m/z (ESI): 401[M+H]$^+$.

Step 2: the preparation method was the same as that of compound 4a, except that compound 4a-1 in the preparation method of compound 4a was replaced with compound 18-1. MS m/z (ESI): 429.3 [M+H]$^+$.

Step 3: the preparation method was the same as that of compound 13-11, except that compound 13-10 in the preparation method of compound 13-11 was replaced with compound 18-2. MS m/z (ESI): 415[M+H]$^+$.

Step 4: the preparation method was the same as that of compound p-13, except that compound 13-11 and compound 2a in the preparation method of compound p-13 were replaced with compound 18-3 and compound 1a. After purification by Prep-HPLC, compound p-18 was obtained as a white solid; $^1$H NMR (400 MHz, DMSO) δ 11.46 (s, 1H), 8.13 (t, 1H), 8.05 (s, 1H), 7.30 (s, 1H), 5.87 (s, 1H), 4.30 (d, 2H), 3.97 (s, 3H), 3.86-3.82 (m, 1H), 3.38 (t, 2H), 3.11 (s, 3H), 2.93 (t, 4H), 2.67 (t, 2H), 2.36-2.29 (m, 1H), 2.23 (s, 3H), 2.11 (s, 3H), 1.89-1.55 (m, 6H), 0.96 (t, 3H), 0.77 (t, 6H). 与 p-19; $^1$H NMR (400 MHz, DMSO) δ 11.46 (s, 1H), 8.13 (t, 1H), 8.05 (s, 1H), 7.29 (s, 1H), 5.87 (s, 1H), 4.30 (d, 2H), 3.97 (s, 3H), 3.93-3.89 (m, 1H), 3.43 (s, 2H), 3.13 (s, 3H), 3.08-2.90 (m, 4H), 2.64-2.59 (m, 2H), 2.24 (s, 3H), 2.11 (s, 3H), 2.08 (s, 1H), 1.76-1.43 (m, 6H), 1.20 (s, 3H), 0.97 (t, 3H), 0.79 (t, 3H). MS m/z (ESI): 549[M+H]$^+$.

Example 20: Preparation of N-((4,6-dimethyl-2-oxo-1,2-dihydropyridin-3-yl) methyl)-5-ethyl-4-(ethyl((1S, 4S)-4-((2-methoxyethyl)(methyl) amino) cyclohexyl)amino)-1-methyl-1H-indazole-6-carboxamide (Compound p-20)

-continued

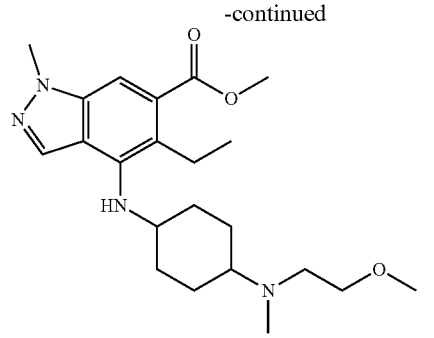

20-1

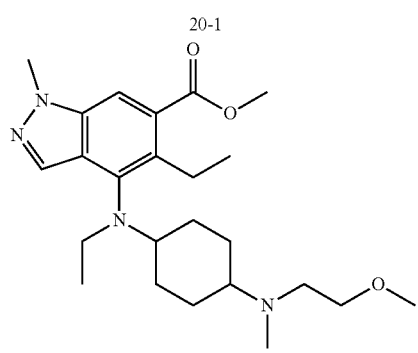

20-2

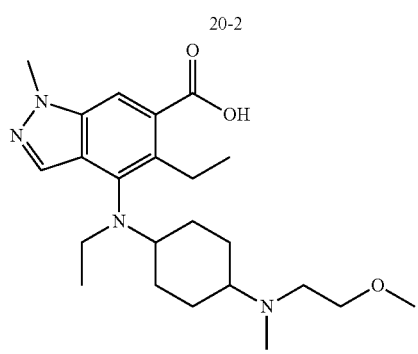

20-3

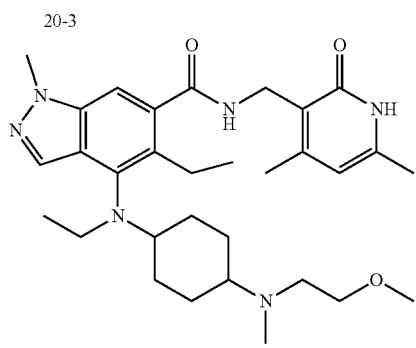

p-20

Step 1: the preparation method was the same as that of compound 4a-1, except that compound 3a and tetrahydropyrone in the preparation method of compound 4a-1 were replaced with compound 16-2 and compound 20.1. MS m/z (ESI): 403.3[M+H]$^+$.

Step 2: the preparation method was the same as that of compound 4a, except that compound 4a-1 in the preparation method of compound 4a was replaced with compound 20-1. MS m/z (ESI): 431.3[M+H]$^+$.

Step 3: the preparation method was the same as that of compound 13-11, except that compound 13-10 in the preparation method of compound 13-11 was replaced with compound 20-2. MS m/z (ESI): 417.4[M+H]$^+$.

Step 4: the preparation method was the same as that of compound p-13, except that compound 13-11 and compound 2a in the preparation method of compound p-13 were replaced with compound 20-3 and compound 1a. After purification by Prep-HPLC, compound p-20 was obtained as a white solid; $^1$H NMR (400 MHz, DMSO-6) δ 11.43 (s, 1H), 8.10 (t, 1H), 8.05 (s, 1H), 7.30 (s, 1H), 5.84 (s, 1H), 4.28 (d, 2H), 3.96 (s, 3H), 3.54-3.47 (m, 2H), 3.25 (s, 3H), 3.21-2.77 (m, 8H), 2.67-2.50 (m, 3H), 2.20 (s, 3H), 2.08 (s, 3H), 1.98-1.71 (m, 3H), 1.62-1.52 (m, 1H), 1.44-1.21 (m, 4H), 0.95 (t, 3H), 0.76 (t, 3H). MS m/z (ESI): 551.3[M+H]$^+$.

Example 21: Preparation of 5-ethyl-4-(methyl((1R, 4R)-4-((2-methoxyethyl) (methyl) amino) cyclohexyl)amino)-N-((4-methoxy-6-methyl-2-oxo-1,2-dihydropyridin-3-yl)methyl)-1-methyl-1H-indazole-6-carboxamide (Compound p-21)

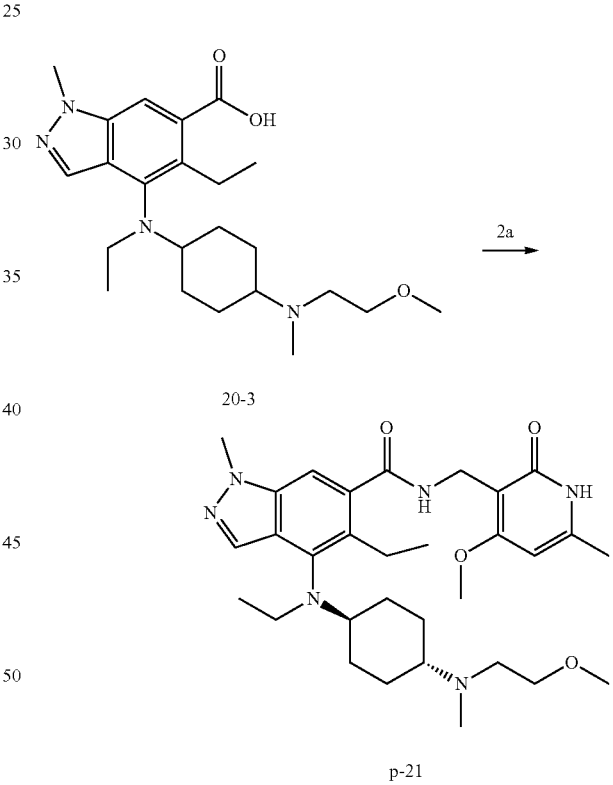

The preparation method was the same as that of compound p-13, except that compound 13-11 in the preparation method of compound p-13 was replaced with compound 20-3. After purification by Prep-HPLC, compound p-21 was obtained as a white solid. MS m/z (ESI): 567[M+H]$^+$; $^1$H NMR (400 MHz, DMSO-6) δ 11.42 (s, 1H), 9.12 (s, 1H), 8.04 (s, 1H), 7.94 (t, 1H), 7.29 (s, 1H), 6.07 (s, 1H), 4.22 (d, 2H), 3.94 (s, 3H), 3.77 (s, 3H), 3.60-3.54 (m, 2H), 3.33-3.20 (m, 5H), 3.15-2.86 (m, 6H), 2.63 (d, 3H), 2.14 (s, 3H), 1.97-1.82 (m, 3H), 1.63-1.54 (m, 1H), 1.45-1.27 (m, 4H), 0.98 (t, 3H), 0.75 (t, 3H).

Example 22: Preparation of 4-((4-(dimethylamino)cyclohexyl)(ethyl) amino)-5-ethyl-N-((4-methoxy-6-methyl-2-oxo-1,2-dihydropyridin-3-yl)methyl)1-methyl-1H-indazole-6-carboxamide (P-22)

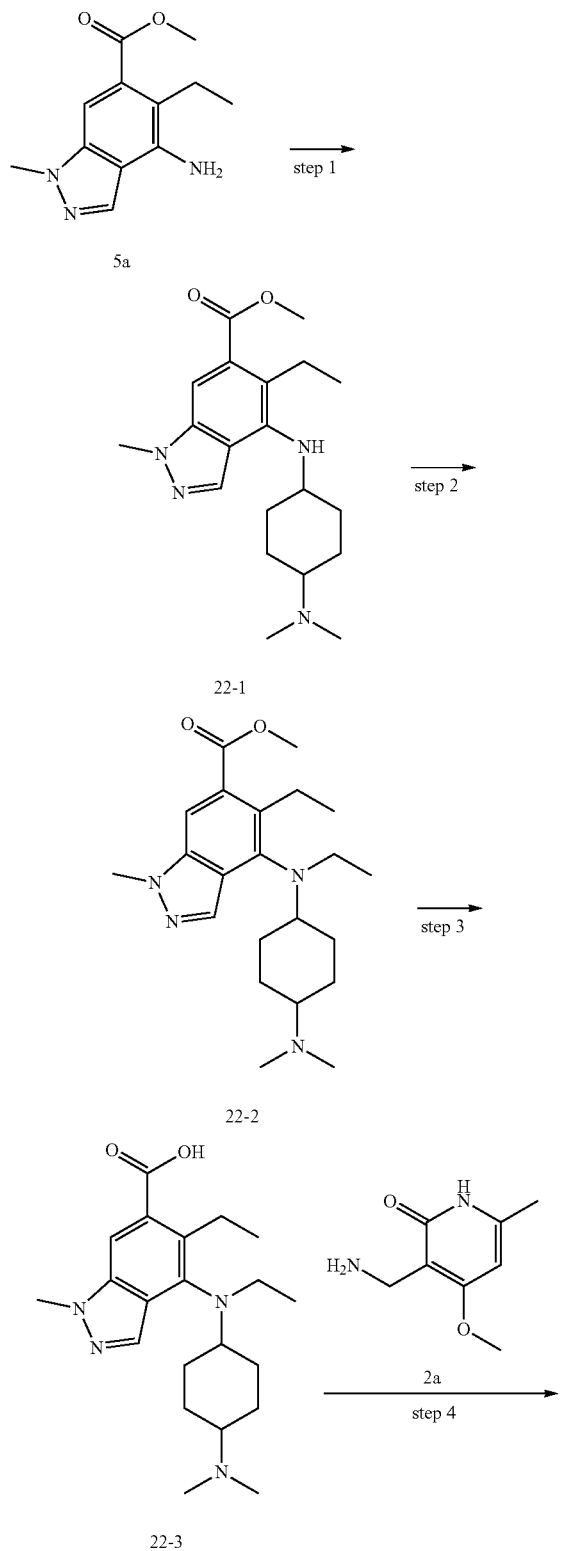

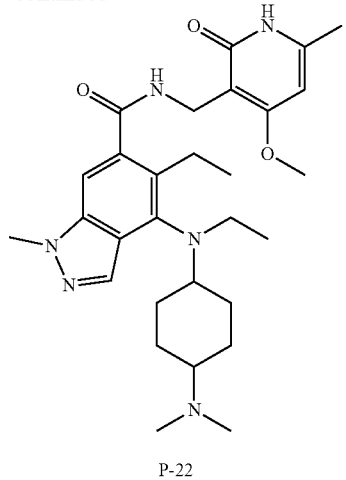

Step 1: a mixed solution of compound 5a (100 mg, 0.408 mmol), 4-dimethylcyclohexanone (121 mg, 0.857 mmol) in dioxane/trifluoroacetic acid (10 ml/2 ml) was stirred at room temperature for 2 h and sodium triacetoxyborohydride (272 mg, 1.29 mmol) was added, and the mixture was stirred at room temperature for 1 h. The reaction was followed by LC-MS until completion. The reaction was quenched with a saturated sodium bicarbonate solution, and the pH was adjusted to 8. The reaction solution was extracted with ethyl acetate, the organic phase was dried over anhydrous sodium sulfate, filtered, and concentrated to give compound 22-1 as a brown oil (150 mg). MS m/z (ESI): 359.3 [M+H]$^+$.

Step 2: a mixed solution of compound 22-1 (150 mg, 0.418 mmol), acetaldehyde (92 mg, 2.07 mmol) in dioxane/acetic acid (20 ml/2 ml) was stirred at room temperature for 1 h and sodium triacetoxyborohydride (443 mg, 2.09 mmol) was added. The mixture was stirred at room temperature for 1 h. The reaction was followed by LC-MS until completion. The reaction solution was quenched with saturated sodium bicarbonate solution and extracted with ethyl acetate. The organic phase was dried over anhydrous sodium sulfate, filtered, and concentrated to give compound 22-2 as a brown oil (150 mg), MS m/z (ESI): 387.4 [M+H]$^+$.

Step 3: to a solution of compound 22-2 (150 mg, 0.388 mmol) in methanol was added sodium hydroxide solution (4 M, 2 ml), and the mixture was stirred at 50° C. for 5 h. The reaction was followed by LC-MS until completion. The reaction solution was concentrated in vacuo to remove methanol, diluted with water, and extracted with ethyl acetate to remove impurities. The aqueous phase was adjusted to pH 4 with hydrochloric acid (3 M), and extracted with ethyl acetate, and the organic phase was dried over anhydrous sodium sulfate, filtered, and concentrated to give compound 22-3 as a black oil (150 mg), MS m/z (ESI): 373.4 [M+H]$^+$.

Step 4: to a solution of compound 22-3 (140 mg, 0.576 mmol) in DMF was added compound 2a (106 mg, 0.564 mmol), HATU (214 mg, 0.564 mmol), and DIPEA (194 mg, 1.50 mmol). The mixture was stirred at room temperature for 5 h. The reaction was followed by LC-MS until completion. The reaction solution was poured into water and extracted with ethyl acetate. The organic phase was washed with brine, dried over anhydrous sodium sulfate, filtered, concentrated, and purified by Pre-HPLC to give compound P-22 as a white solid (6 mg, 3%), MS m/z (ESI): 523.3[M+H]$^+$.

$^1$H NMR (400 MHz, DMSO) δ 11.40 (s, 1H), 8.22 (s, 1H), 8.03 (s, 1H), 7.92 (t, 1H), 7.26 (s, 1H), 6.06 (s, 1H), 4.22 (d, J=4.4 Hz, 2H), 3.99 (s, 3H), 3.94 (s, 3H), 3.18-3.05 (m, 2H), 2.93-2.88 (m, 4H), 2.16 (s, 6H), 2.14 (s, 3H), 1.72-1.52 (m, 4H), 1.34-1.11 (m, 4H), 0.98 (t, J=7.6 Hz, 3H), 0.75 (t, J=7.2 Hz, 3H).

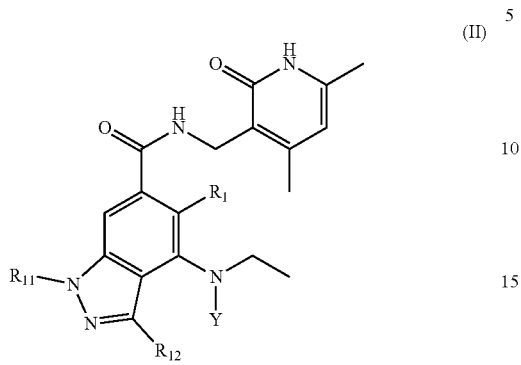

(II)

The target compounds of the examples were shown in formula (II), and the substituents $R_1$, $R_{11}$, $R_{12}$ and Y were shown in the following table.

General procedure: compounds P-23 to P-42 were prepared by a similar method to Example 22 using compounds 5a-12a and 14a-21a, 23a or corresponding ketones thereof as raw materials, except that compound 2a in step 4 was replaced with compound 1a (Et stands for ethyl, Me stands for methyl).

| Example No. | compound No. | $R_1$ | Y | $R_{11}$ | $R_{12}$ | MS $[M + H]^+$ |
|---|---|---|---|---|---|---|
| 23 | P-23 | Et | | Me | H | 507.3 |
| 24 | P-24 | Et | | Me | H | 549.4 |
| 25 | P-25 | Et | | Me | H | 547.3 |

-continued

| Example No. | compound No. | R₁ | Y | R₁₁ | R₁₂ | MS [M + H]⁺ |
|---|---|---|---|---|---|---|
| 26 | P-26 | Me | cyclohexyl-CH₂-N(Me)₂ | Me | H | 507.4 |
| 27 | P-27 | CN | tetrahydropyran-4-yl | Me | H | 463.3 |
| 28 | P-28 | cyclopropyl | tetrahydropyran-4-yl | Me | H | 478.4 |
| 29 | P-29 | Et | 4-(piperazin-1-yl)cyclohexyl | Me | H | 548 |
| 30 | P-30 | Et | 4-(4-methylpiperazin-1-yl)cyclohexyl | Me | H | 562 |
| 31 | P-31 | Me | 4-(3,3-difluoroazetidin-1-yl)cyclohexyl | Me | H | 541 |
| 32 | P-32 | Me | 4-(piperidin-1-yl)cyclohexyl | Me | H | 533.5 |

-continued
| Example No. | compound No. | R₁ | Y | R₁₁ | R₁₂ | MS [M + H]⁺ |
|---|---|---|---|---|---|---|
| 33 | P-33 | Me | 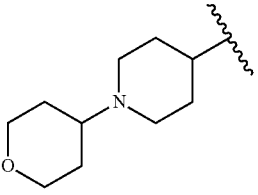 [SMILES: *C1CCN(C2CCOCC2)CC1] | Me | H | 535.4 |
| 34 | P-34 | Me | 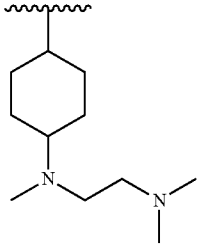 [SMILES: *C1CCC(N(C)CCN(C)C)CC1] | Me | H | 550.5 |
| 36 | P-36 | Et | 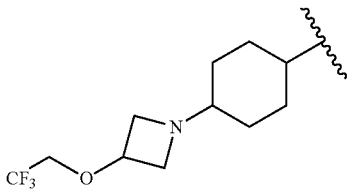 [SMILES: *C1CCC(N2CC(OCC(F)(F)F)C2)CC1] | Me | H | 617.4 |
| 37 | P-37 | Me | 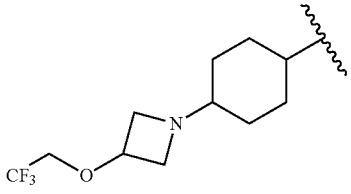 [SMILES: *C1CCC(N2CC(OCC(F)(F)F)C2)CC1] | Me | H | 603.3 |
| 39 | P-39 | Et | 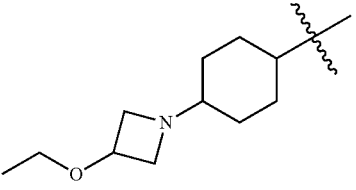 [SMILES: *C1CCC(N2CC(OCC)C2)CC1] | Me | H | 563.4 |
| 40 | P-40 | Me | 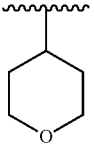 | 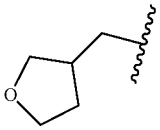 [SMILES: *CC1CCOC1] | H | 522.5 |
| 41 | P-41 | Me | 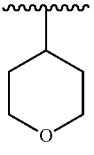 [SMILES: *C1CCOCC1] | Me | F | 470.5 |

| Example No. | compound No. | R₁ | Y | R₁₁ | R₁₂ | MS [M + H]⁺ |
|---|---|---|---|---|---|---|
| 42 | P-42 | Me | 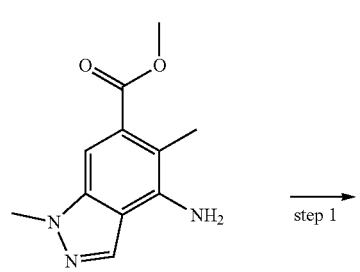 | Me | Me | 507.4 |
Example 44: Preparation of N-((4,6-dimethyl-2-oxo-1,2-dihydropyridin-3-yl) methyl)-4-(ethyl(4-(methyl(2, 2, 2-trifluoroethyl) amino)cyclohexyl) amino)-1,5-dimethyl-1H-indazole-6-carboxamide (Compound P-44)
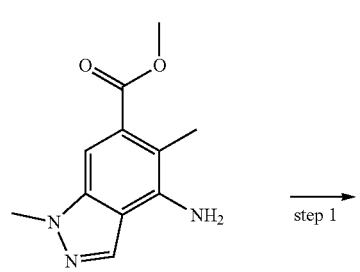
8a
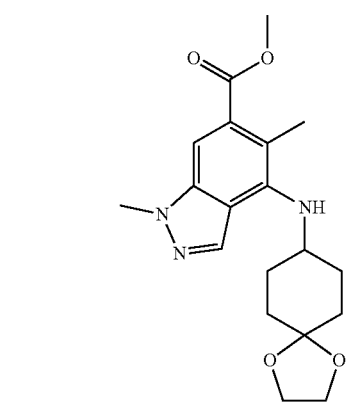
44-1
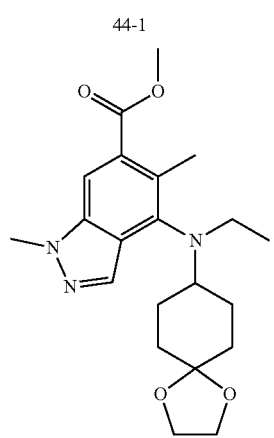
44-2
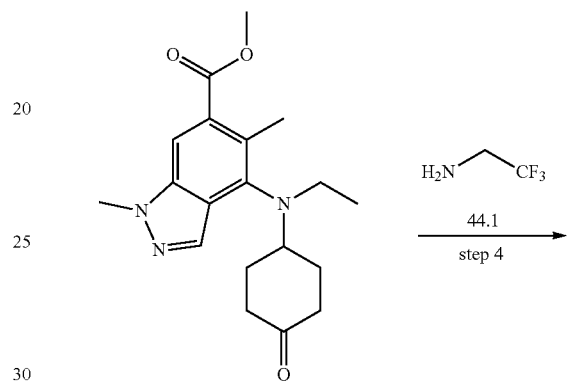
44-3
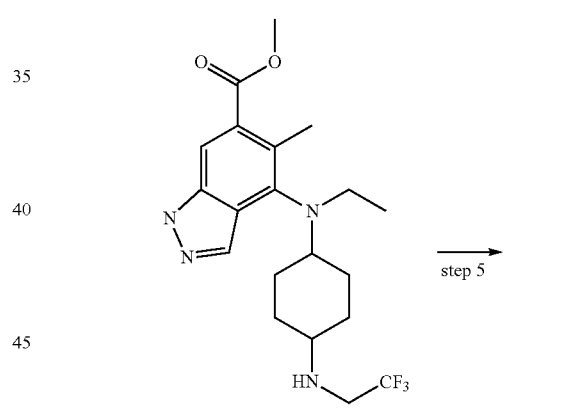
44-4
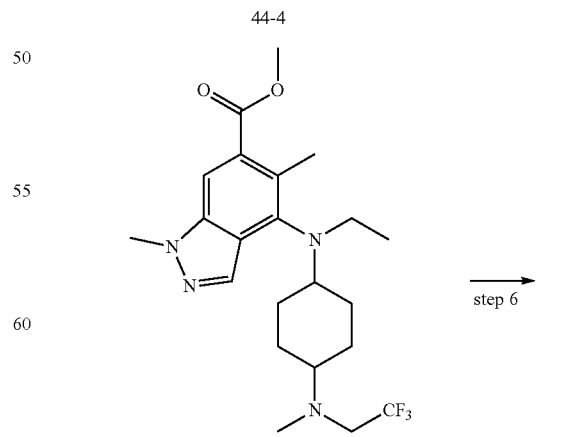
44-5

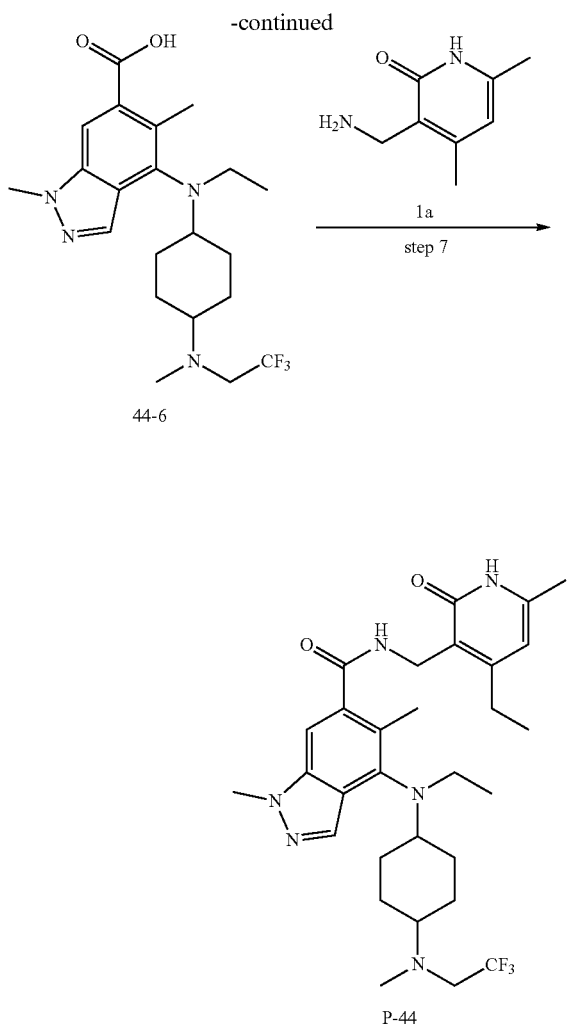

purified by column chromatography to obtain compound 44-4 (130 mg, 26%) as an oil, MS m/z (ESI): 427.3 [M+H]$^+$.

Step 5: the preparation method was the same as that of compound 44-4, except that compound 44-3 and compound 44.1 were replaced with compound 44-4 and formaldehyde, and the solvent was replaced with methanol/acetic acid solution. MS m/z (ESI): 441.3[M+H]$^+$.

Step 6: the preparation method was the same as that of compound 22-3, except that compound 22-2 was replaced with compound 44-5. MS m/z (ESI): 427.3[M+H]$^+$.

Step 7: the preparation method was the same as that of compound P-22, except that compound 22-3 and compound 2a were replaced with compound 44-6 and 1a. After purification by Prep-HPLC, compound P-44 (54 mg, 37%) was obtained as a white solid, MS m/z (ESI): 561.3[M+H]$^+$. $^1$H NMR (500 MHz, DMSO) δ 11.48 (s, 1H), 8.16 (t, J=4.8 Hz, 1H), 8.07 (s, 1H), 7.31 (s, 1H), 5.87 (s, 1H), 4.30 (d, J=4.8 Hz, 2H), 3.98 (s, 3H), 3.76-3.72 (m, 1H), 3.27-3.08 (m, 3H), 3.04-2.93 (m, 1H), 2.51-2.45 (m, 1H), 2.34 (s, 3H), 2.33 (s, 3H), 2.22 (s, 3H), 2.11 (s, 3H), 1.71-1.14 (m, 8H), 0.83 (t, J=7.2 Hz, 3H).

Example 45: Preparation of 4-((4-((2, 2-difluoroethyl) (methyl)amino) cyclohexyl)(ethyl) amino)-N-((4,6-dimethyl-2-oxo-1,2-dihydropyridin-3-yl) methyl)-1,5-dimethyl-1H-indazole-6-carboxamide (Compound P-45)

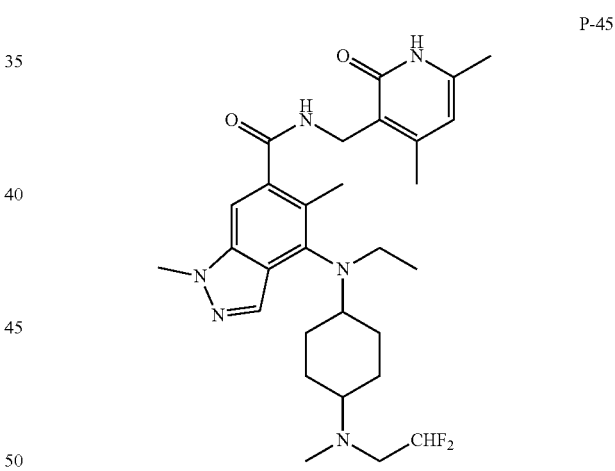

P-45

Step 1: the preparation method was the same as that of compound 22-1, except that compound 5a and 4-dimethyl-cyclohexanone were replaced with compound 8a and compound 14a-4, and the reaction temperature was 0° C. MS m/z (ESI): 360.2[M+H]$^+$.

Step 2: the preparation method was the same as that of compound 22-2, except that compound 22-1 was replaced with compound 44-1, and the reaction temperature was 0° C. MS m/z (ESI): 388.3[M+H]$^+$.

Step 3: a solution of compound 44-2 (750 mg, 1.94 mmol) in trifluoroacetic acid/water (10 ml/1 ml) was stirred at 50° C. for 5 h. After the reaction solution was cooled to room temperature, the reaction was quenched with saturated sodium bicarbonate aqueous solution, extracted with dichloromethane, and the organic phase was dried over anhydrous sodium sulfate, filtered, concentrated, and purified by column chromatography to give compound 44-3 as a white solid (650 mg, 97%), MS m/z (ESI): 344.3[M+H]$^+$.

Step 4: a solution of compound 44-3 (500 mg, 1.46 mmol) and compound 44.1 (288 mg, 2.91 mmol) in dichloromethane/acetic acid (10 ml/0.2 ml) was stirred at 0° C. for 1 h. Sodium triacetoxyborohydride (925 mg, 4.37 mmol) was added at 0° C. and the mixture was stirred at 0° C. for 2 h. The reaction was followed by LC-MS until completion. The reaction was quenched with saturated sodium bicarbonate aqueous solution and extracted with dichloromethane, dried over anhydrous sodium sulfate, filtered, concentrated, and The preparation method was the same as that of compound P-44, except that compound 44.1 in step 4 was replaced with 2,2-difluoroethylamine. After purification by Prep-HPLC, compound P-45 (123 mg, 71%) was obtained as a white solid, MS m/z (ESI): 543.3[M+H]$^+$. $^1$H NMR (400 MHz, DMSO) δ 11.45 (s, 1H), 8.15 (t, J=5.2 Hz, 1H), 8.09 (s, 1H), 7.35 (s, 1H), 5.83 (s, 1H), 4.31-4.26 (m, 4H), 3.77-3.72 (m, 3H), 3.59-3.56 (m, 2H), 3.46-3.44 (m, 1H), 3.28-3.12 (m, 4H), 2.76-2.73 (m, 1H), 2.24 (s, 3H), 2.19 (s, 3H), 2.07 (s, 3H), 1.85-1.81 (m, 2H), 1.63-1.57 (m, 2H), 1.46-1.22 (m, 3H), 0.74 (t, J=7.2 Hz, 3H).

Example 46: Preparation of 4-((4-amino-4-methyl-cyclohexyl) (ethyl)amino)-N-((4,6-dimethyl-2-oxo-1,2-dihydropyridin-3-yl)methyl)-1H-indazole-6-carboxamide (Compound P-46)

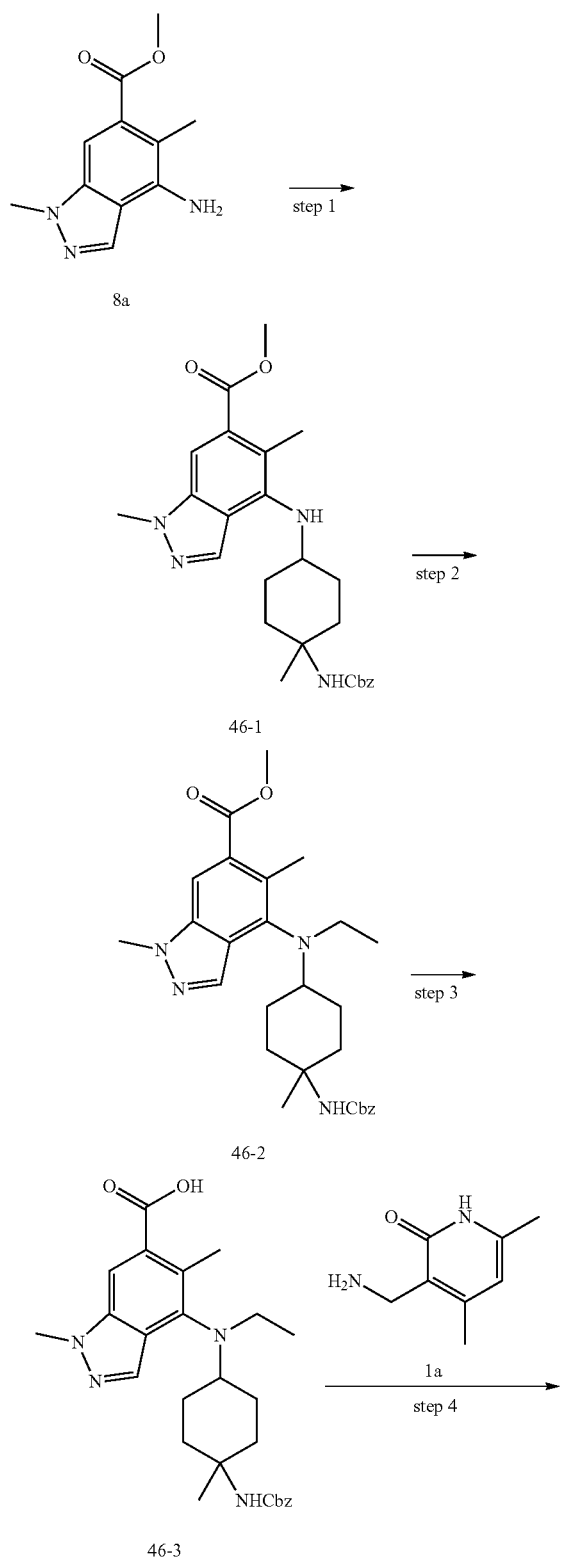

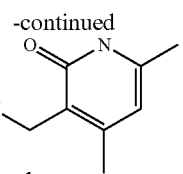

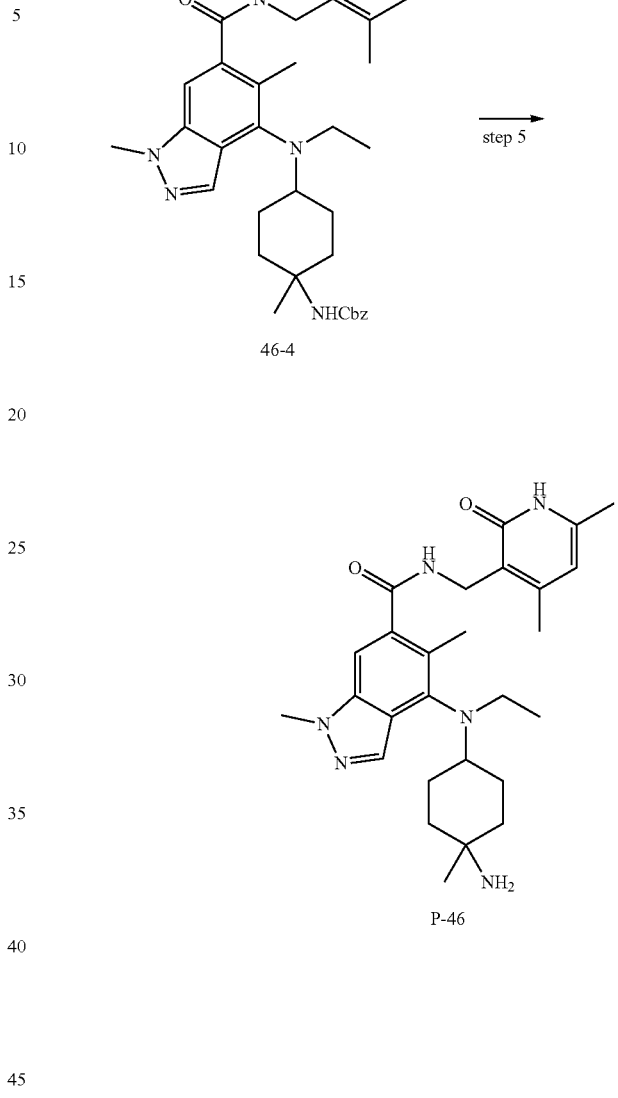

Step 1 to step 4: The preparation method was the same as that of compound P-22, except that compound 5a and compound 2-dimethylcyclohexanone in step 1 were replaced with compound 8a and 24a.

Step 5: to a solution of compound 46-4 (180 mg, 0.29 mmol) in ethanol/hydrochloric acid (10 ml/1 ml, 1 M) was added palladium on carbon (18 mg), and the mixture was stirred under hydrogen atmosphere at room temperature overnight. The reaction was followed by LC-MS until completion. The reaction solution was filtered, and the filtrate was concentrated, and purified by Pre-HPLC to give compound P-46 as a white solid (19.11 mg, 14%).

MS m/z (ESI): 479.3[M+H]$^+$. $^1$H NMR (400 MHz, DMSO) δ 11.43 (s, 1H), 8.40 (s, 1H), 8.14 (t, J=4.0 Hz, 1H), 8.07 (s, 1H), 7.32 (s, 1H), 5.87 (s, 1H), 4.30 (d, J=4.0 Hz, 2H), 3.98 (s, 3H), 3.33-3.32 (m, 2H), 3.05-3.04 (m, 1H), 2.27 (s, 3H), 2.23 (s, 3H), 2.11 (s, 3H), 1.59-1.58 (m, 4H), 1.43-1.42 (m, 4H), 1.19 (s, 3H), 0.77 (t, J=8.0 Hz, 3H).

Example 47: Preparation of N-((4,6-dimethyl-2-oxo-1,2-dihydropyridin-3-yl) methyl)-5-ethyl-4-(ethyl(4-(3-hydroxyazetidin-1-yl)cyclohexyl)amino)-1-methyl-1H-indazole-6-carboxamide (Compound P-47)
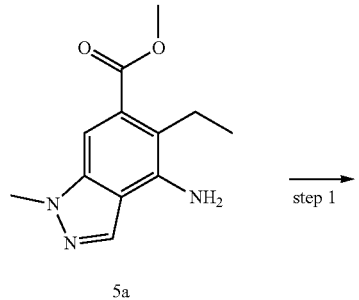
5a
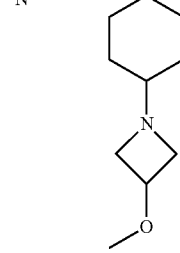
step 1
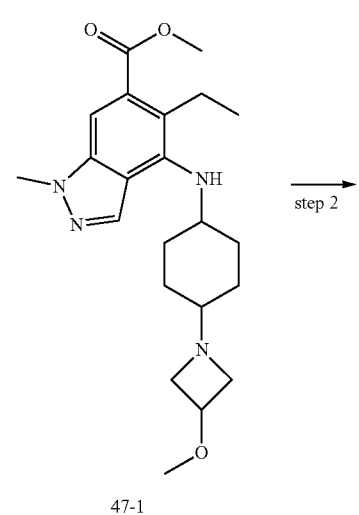
47-1
step 2
47-2
step 3
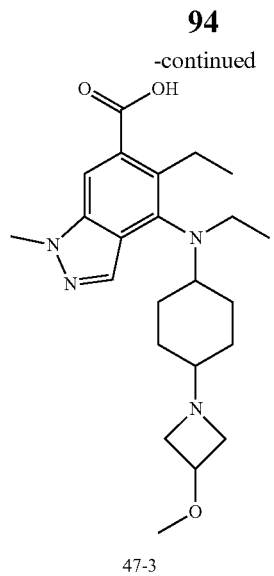
47-3
step 4
47-4
step 5

-continued

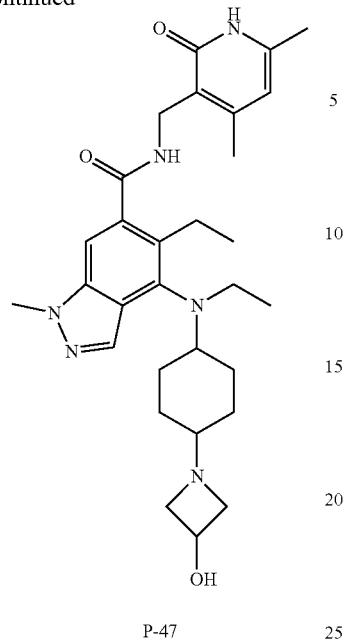

P-47

Step 1 to step 4: the preparation method was the same as that of compound P-22, except that compound 2-dimethyl-cyclohexanone in step 1 was replaced with compound 22a.

Step 5: to a solution of compound 47-4 (30 mg, 0.055 mmol) in dichloromethane was slowly added boron tribromide solution (IM, 0.27 ml) dropwise at −70° C., and the mixture was stirred at room temperature for 2 h. The reaction was followed by LC-MS until completion. The reaction solution was added with methanol (10 ml) and saturated sodium bicarbonate solution, extracted with dichloromethane, and the organic phase was dried over anhydrous sodium sulfate, filtered, concentrated, and purified by column chromatography to give compound P-47 as a white solid (7 mg, 24%). MS m/z (ESI): 535.3[M+H]$^+$. $^1$H NMR (400 MHz, DMSO) δ 11.45 (s, 1H), 8.12 (t, J=4.0 Hz, 1H), 8.02 (s, 1H), 7.27 (s, 1H), 5.84 (s, 1H), 5.20 (br, 1H), 4.26 (d, J=4.0 Hz, 2H), 4.04-4.03 (m, 1H), 3.94 (s, 3H), 3.39-3.38 (m, 2H), 3.14-3.13 (m, 1H), 2.89-2.87 (m, 3H), 2.61-2.60 (m, 2H), 2.20 (s, 3H), 2.07 (s, 3H), 1.91-1.81 (m, 2H), 1.65-1.47 (m, 4H), 1.30-1.20 (m, 2H), 0.92 (t, J=8.0 Hz, 3H), 0.75-0.72 (m, 5H).

Example 48: Preparation of N-((4,6-dimethyl-2-oxo-1,2-dihydropyridin-3-yl)methyl)-4-(ethyl(1-(oxetane-3-yl)piperidin-4-yl)amino)-1,5-dimethyl-1H-indazole-6-carboxamide (Compound P-48)

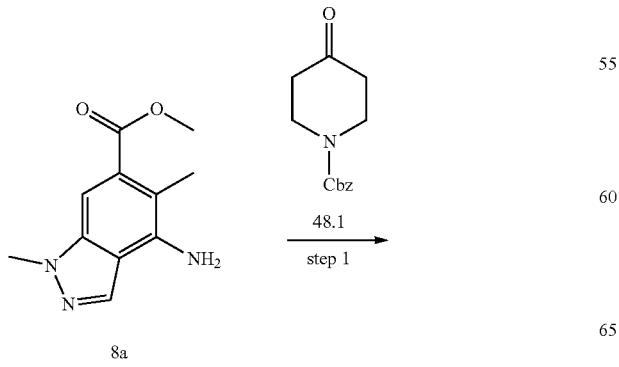

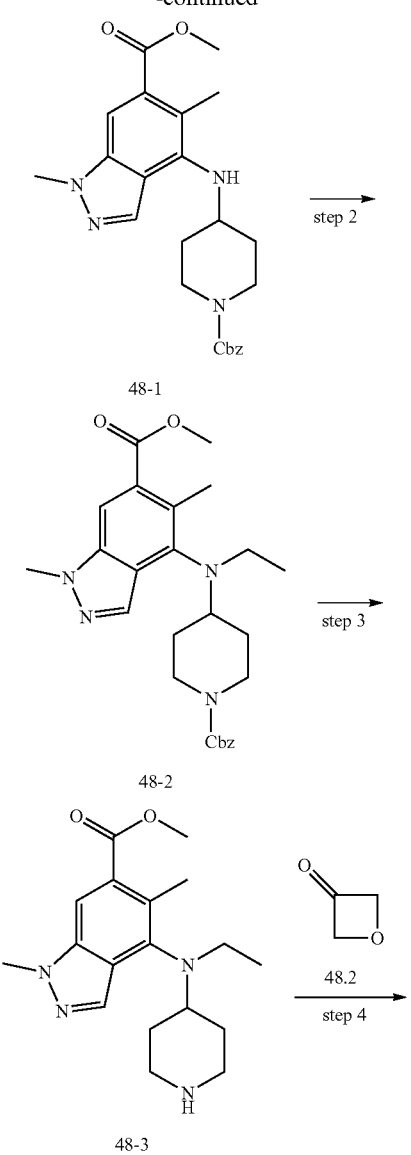

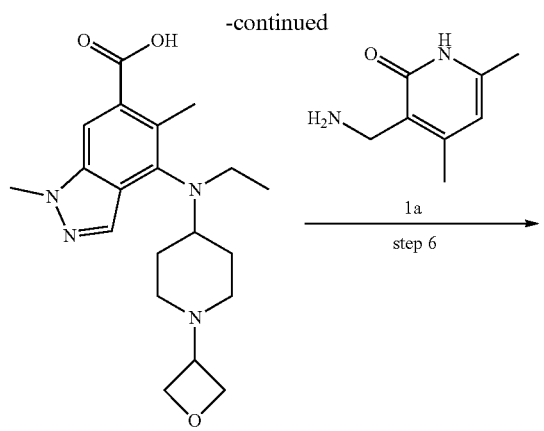

48-5

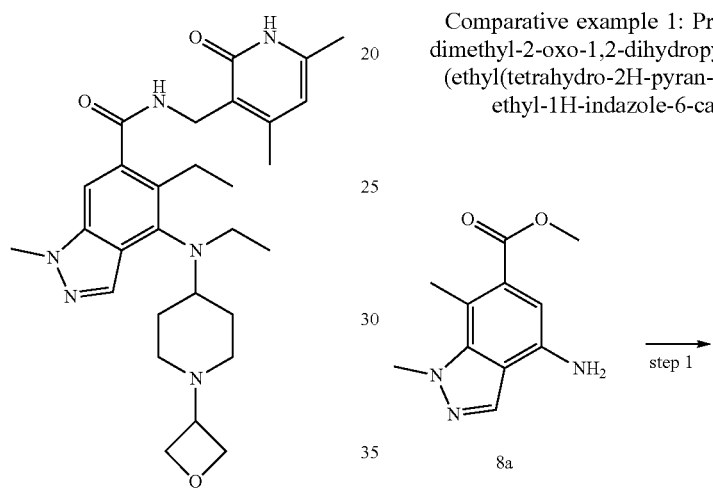

P-48

Step 1: the preparation method was the same as that of compound 22-1, except that compound 5a and 4-dimethylcyclohexanone were replaced with compound 8a and compound 48.1.

Step 2: the preparation method was the same as that of compound 22-2, except that compound 22-1 was replaced with compound 48-1.

Step 3: to a solution of compound 48-2 (358 mg, 0.77 mmol) in methanol was added a catalytic amount of hydrochloric acid (12 M) and palladium on carbon, and the mixture was stirred at room temperature under a hydrogen atmosphere for 16 h. The reaction was followed by LC-MS until completion. The reaction solution was filtered and the filtrate was concentrated to give compound 48-3 (240 mg). MS m/z (ESI): 331 [M+H]$^+$.

Step 4: a solution of compound 48-3 (240 mg, 0.72 mmol), and DIPEA (188 mg, 1.45 mmol) in dioxane was stirred at room temperature for 30 min, compound 48.2 (104 mg, 1.45 mmol) was added, and the mixture was stirred at room temperature for 30 min. Sodium triacetoxyborohydride (231 mg, 1.09 mmol) was added and the mixture was stirred at room temperature for 3 h. The reaction was followed by LC-MS until completion. The reaction was quenched with saturated sodium bicarbonate solution and the pH was adjusted to 8-9. The reaction solution was extracted with dichloromethane and the organic phase was washed with saturated brine, dried over anhydrous sodium sulfate, filtered and concentrated to give compound 48-4 (230 mg). MS m/z (ESI): 387 [M+H]$^+$.

Step 5: the preparation method was the same as that of compound 22-3, except that compound 22-2 was replaced with compound 48-4. MS m/z (ESI): 373[M+H]$^+$.

Step 6: the preparation method was the same as that of compound 22-4, except that compound 22-3 and compound 2a were replaced with compound 48-4 and compound 1a. MS m/z (ESI): 507[M+H]$^+$. $^1$H NMR (500 MHz, DMSO) δ 11.49 (s, 1H), 8.15 (t, J=5.0 Hz, 1H), 8.07 (s, 1H), 7.31 (s, 1H), 5.87 (s, 1H), 4.47 (t, J=6.4 Hz, 2H), 4.35 (t, J=6.0 Hz, 2H), 4.30 (d, J=5.0 Hz, 2H), 3.98 (s, 3H), 3.28 (m, 2H), 3.22-3.12 (m, 1H), 3.09-3.02 (m, 1H), 2.28 (s, 3H), 2.23 (s, 3H), 2.11 (s, 3H), 1.88 (m, 1H), 1.78-1.56 (m, 3H), 1.48-1.31 (m, 2H), 0.76 (t, J=7.1 Hz, 3H).

Comparative example 1: Preparation of N-((4,6-dimethyl-2-oxo-1,2-dihydropyridin-3-yl) methyl)-4-(ethyl(tetrahydro-2H-pyran-4-yl)amino)-1,7-dimethyl-1H-indazole-6-carboxamide (D1)

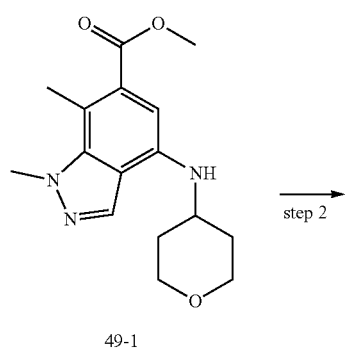

8a

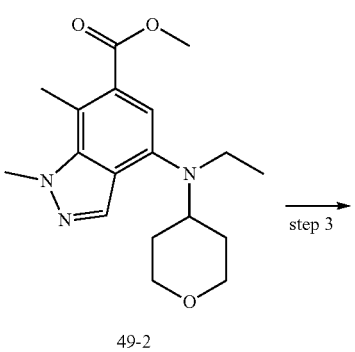

49-1

49-2

-continued

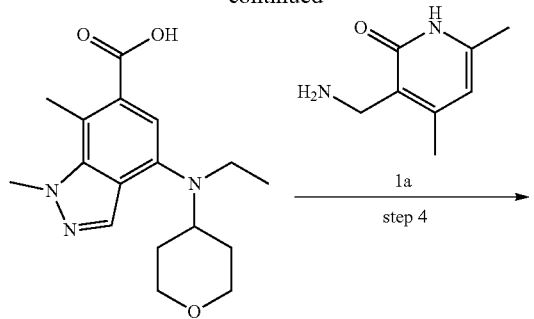

49-3

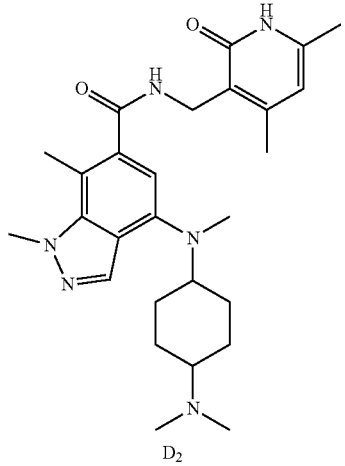

Comparative example 2

D$_2$
MS m/z(ESI): 493[M+H]$^+$

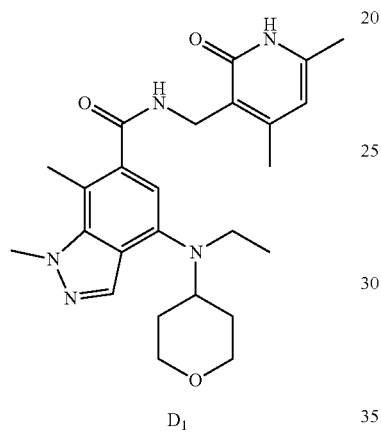

D$_1$

Step 1: the preparation method was the same as that of compound 22-1, except that compound 5a and 4-dimethylaminocyclohexanone in the preparation method were replaced with compound 13a and tetrahydropyrone. MS m/z (ESI): 304.2[M+H]$^+$.

Step 2: the preparation method was the same as that of compound 22-2, except that compound 22-1 in the preparation method was replaced with compound 49-1. MS m/z (ESI): 332.8[M+H]$^+$.

Step 3: the preparation method was the same as that of compound 22-3, except that compound 22-2 in the preparation method was replaced with compound 49-2. MS m/z (ESI): 318.3 [M+H]$^+$.

Step 4: the preparation method was the same as that of compound P-22, except that compound 22-3 and compound 2a in the preparation method were replaced with compound 49-3 and compound 1a. MS m/z (ESI): 452[M+H]$^+$. $^1$H NMR (400 MHz, DMSO) δ 11.49 (s, 1H), 8.05 (t, J=4.0 Hz, 1H), 7.88 (s, 1H), 6.36 (s, 1H), 5.87 (s, 1H), 4.28 (d, J=4.0 Hz, 2H), 4.24 (d, J=4.0 Hz, 3H), 3.88-3.85 (m, 2H), 3.64-3.63 (m, 1H), 3.29-3.23 (m, 4H), 2.56 (s, 3H), 2.21 (s, 3H), 2.11 (s, 3H), 1.68-1.66 (m, 4H), 0.96 (t, J=8.0 Hz, 3H).

Comparative Example 2-4

Comparative compounds D2 to D4 are prepared by referring to the preparation method of comparative compound D1.

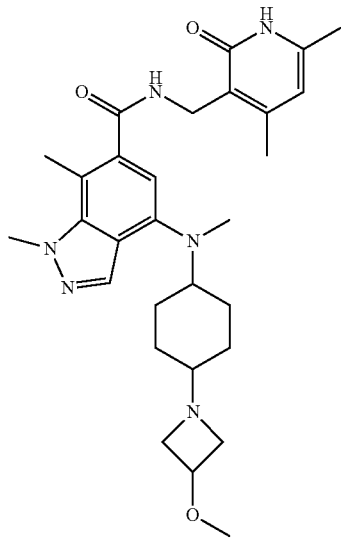

Comparative example 3

D$_3$
MS m/z(ESI): 535[M+H]$^+$

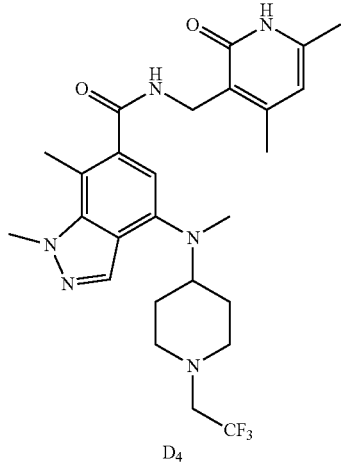

Comparative example 4

D$_4$
MS m/z(ESI): 533[M+H]$^+$

| Compound No. | Structure | ¹HNMR |
|---|---|---|
| P-23 | 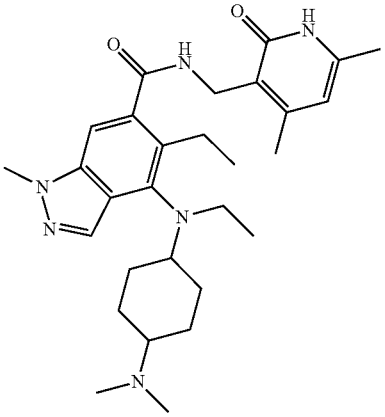 | ¹H NMR (400 MHz, DMSO) δ 11.46 (s, 1H), 9.27 (s, 1H), 8.12 (s, 1H), 8.06 (s, 1H), 7.31 (s, 1H), 5.85 (s, 1H), 4.27 (d, J = 4.4 Hz, 2H), 3.95 (s, 3H), 3.30-3.24 (m, 1H), 3.12-3.03 (m, 2H), 2.95-2.87 (m, 2H), 2.64 (s, 3H), 2.63 (s, 3H), 2.20 (s, 3H), 2.08 (s, 3H), 1.93-1.79 (m, 3H), 1.61-1.52 (m, 1H), 1.41-1.22 (m, 4H), 0.94 (t, J = 7.2 Hz, 3H), 0.75 (t, J = 7.2 Hz, 3H). |
| P-24 | 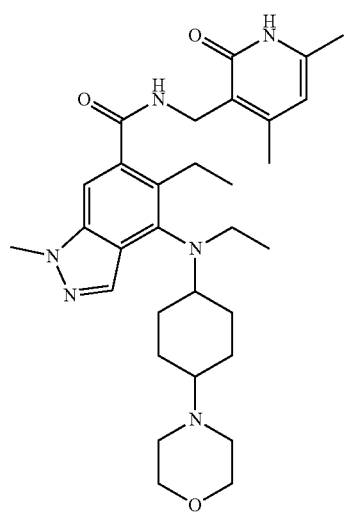 | ¹H NMR (400 MHz, DMSO) δ 11.46 (s, 1H), 8.13 (t, J = 5.1 Hz, 1H), 8.06 (s, 1H), 7.30 (s, 1H), 5.87 (s, 1H), 4.30 (d, J = 5.1 Hz, 2H), 3.98 (s, 3H), 3.54-3.47 (m, 4H), 3.01-2.87 (m, 4H), 2.67 (s, 1H), 2.43-2.36 (m, 4H), 2.33 (s, 1H), 2.23 (s, 3H), 2.11 (s, 3H), 1.89-1.63 (m, 4H), 1.29-1.08 (m, 4H), 0.96 (t, J = 7.5 Hz, 3H), 0.78 (t, J = 7.2 Hz, 3H). |
| P-25 | 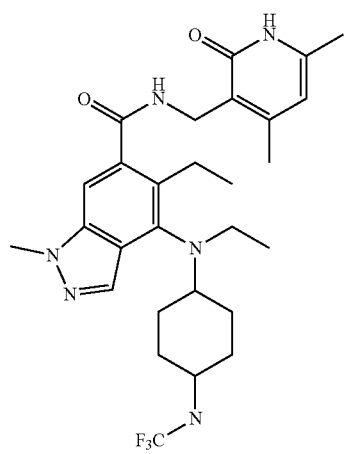 | ¹H NMR (400 MHz, DMSO) δ 11.44 (s, 1H), 8.11 (t, J = 4.8 Hz, 1H), 8.05 (s, 1H), 7.29 (s, 1H), 5.83 (s, 1H), 4.26 (d, J = 5.2 Hz, 2H), 3.94 (s, 3H), 3.29-2.78 (m, 10H), 2.29-2.13 (m, 4H), 2.07 (s, 3H), 1.91-1.80 (m, 1H), 1.36-1.26 (m, 4H), 0.93 (t, J = 7.6 Hz, 3H), 0.75 (t, J = 6.8 Hz, 3H). |

-continued
| Compound No. | Structure | ¹HNMR |
|---|---|---|
| P-26 | 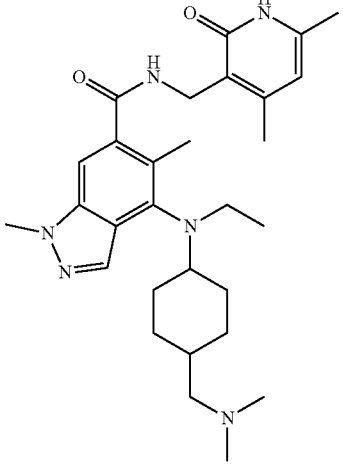 | ¹H NMR (400 MHz, DMSO) δ 11.44 (s, 1H), 8.10 (s, 1H), 8.09 (t, J = 4.8 Hz, 1H), 8.02 (s, 1H), 7.28 (s, 1H), 5.84 (s, 1H), 4.27 (d, J = 4.8 Hz, 2H), 3.95 (s, 3H), 3.00-2.59 (m, 11H), 2.24 (s, 3H), 2.19 (s, 3H), 2.08 (s, 3H), 1.72-1.51 (m, 4H), 1.38-1.25 (m, 3H), 0.89-0.84 (m, 2H), 0.74 (t, J = 7.2 Hz, 3H). |
| P-27 | 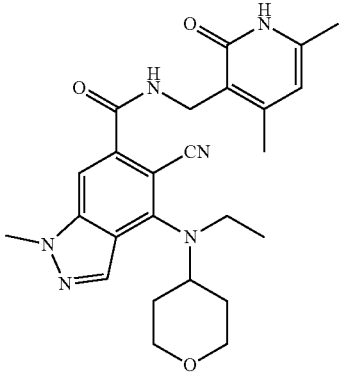 | ¹H NMR (400 MHz, DMSO) δ 11.47 (s, 1H), 8.46 (t, J = 4.0 Hz, 1H), 8.34 (s, 1H), 7.55 (s, 1H), 5.85 (s, 1H), 4.29 (d, J = 4.0 Hz, 2H), 4.01 (s, 3H), 3.82-3.80 (m, 2H), 3.64-3.63 (m, 1H), 3.46-3.42 (m, 2H), 3.25-3.22 (m, 2H), 2.19 (s, 3H), 2.08 (s, 3H), 1.71-1.66 (m, 4H), 0.84 (t, J = 8.0 Hz, 3H). |
| P-28 | 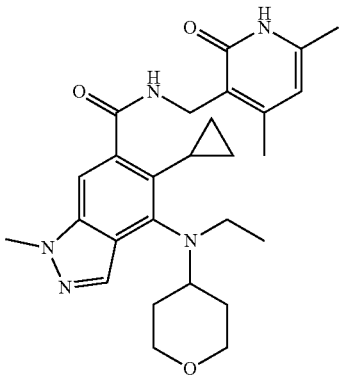 | ¹H NMR (400 MHz, DMSO) δ 11.43 (s, 1H), 8.05 (s, 1H), 7.95 (t, J = 4.0 Hz, 1H), 7.15 (s, 1H), 5.84 (s, 1H), 4.26 (d, J = 4.0 Hz, 2H), 3.92 (s, 3H), 3.81-3.79 (m, 2H), 3.43-3.42 (m, 2H), 3.24-3.23 (m, 2H), 2.23 (s, 3H), 2.08 (s, 3H), 1.81-1.80 (m, 1H), 1.63-1.61 (m, 4H), 1.21-1.19 (m, 1H), 0.82 (t, J = 8.0 Hz, 3H), 0.70-0.68 (m, 2H), 0.41-0.39 (m, 2H). |

| Compound No. | Structure | ¹HNMR |
|---|---|---|
| P-29 | 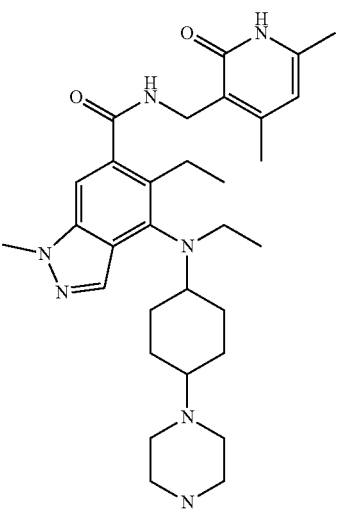 | ¹H NMR (400 MHz, dmso) δ 11.46 (s, 1H), 8.32 (s, 1H), 8.14 (t, 7 = 5.0 Hz, 1H), 8.06 (s, 1H), 7.31 (s, 1H), 5.87 (s, 1H), 4.30 (d, J = 5.0 Hz, 2H), 3.98 (s, 3H), 3.35-2.88 (m, 8H), 2.82 (s, 3H), 2.23 (s, 3H), 2.18 (d, J = 9.7 Hz, 1H), 2.11 (s, 3H), 2.07-1.99 (m. 1H), 1.83-1.51 (m, 4H), 1.42-1.07 (m, 5H), 0.96 (t, J = 7.4 Hz, 3H), 0.78 (t, 7 = 7.1 Hz, 3H). |
| P-30 | 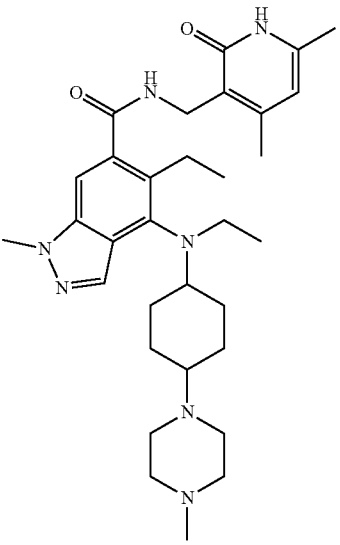 | ¹H NMR (400 MHz, dmso) δ 11.47 (s, 1H), 8.23 (s, 1H), 8.14 (t, J = 5.1 Hz, 1H), 8.06 (s, 1H), 7.30 (s, 1H), 5.87 (s, 1H), 4.30 (d, J = 5.0 Hz, 2H), 3.98 (s, 3H), 3.24-2.80 (m, 8H), 2.42 (s, 3H), 2.23 (s, 4H), 2.11 (s, 6H), 1.86-1.57 (m, 4H), 1.41-1.11 (m, 5H), 0.96 (t, J = 7.4 Hz, 3H), 0.77 (t, J = 7.1 Hz, 3H). |
| P-31 | 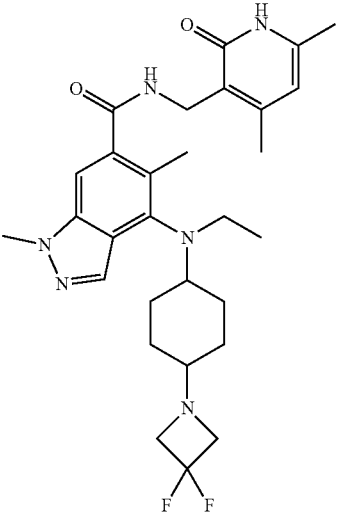 | ¹H NMR (400 MHz, DMSO) δ 11.44 (s, IH), 8.09 (t, J = 5.2 Hz, 1H), 8.02 (s, 1H), 7.26 (s, 1H), 5.84 (s, 1H), 4.27 (d, J = 5.1 Hz, 2H), 3.95 (s, 3H), 3.43 (t, J = 12.4 Hz, 4H), 3.28-3.25 (m, 1H), 2.94 (t, J = 13.2 Hz, 2H), 2.23 (s, 3H), 2.19 (s, 3H), 2.08 (s, 3H), 1.99 (s, 1H), 1.71-1.56 (m, 3H), 1.37-1.17 (m, 3H), 0.93-0.85 (m, 2H), 0.73 (t, J = 7.1 Hz, 3H). |

| Compound No. | Structure | ¹HNMR |
|---|---|---|
| P-32 | 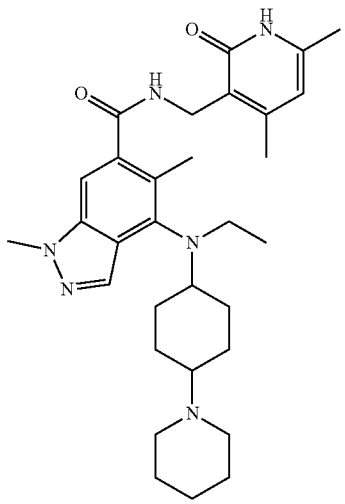 | ¹H NMR (400 MHz, DMSO) δ 11.43 (s, 1H), 8.23 (s, 1H), 8.10 (t, J = 5.2 Hz, 1H), 8.02 (s, 1H), 7.26 (s, 1H), 5.83 (s, 1H), 4.26 (d, J = 5.2 Hz, 2H), 3.94 (s, 3H), 3.45-3.09 (m, 5H), 2.92-2.86 (m, 1H), 2.31-2.27 (m, 1H), 2.22 (s, 3H), 2.19 (s, 3H), 2.07 (s, 3H), 1.69-1.20 (m, 14H), 0.72 (t, J = 7.2 Hz, 3H). |
| P-33 | 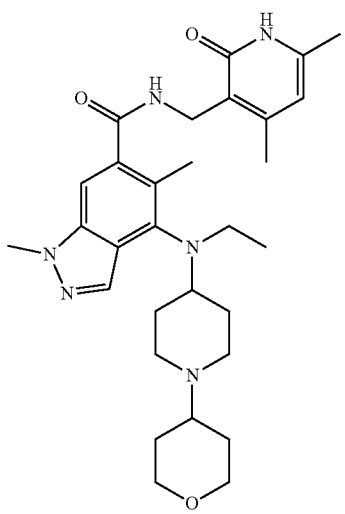 | ¹H NMR (400 MHz, DMSO) δ 11.44 (s, IH), 8.11 (t, J = 4.8 Hz, 1H), 8.03 (s, 1H), 7.27 (s, 1H), 5.84 (s, 1H), 4.26 (d, J = 4.8 Hz, 2H), 3.94 (s, 3H), 3.81-3.79 (m, 2H), 3.21-3.15 (m, 4H), 2.99-2.63 (m, 5H), 2.34-2.29 (m, 1H), 2.24 (s, 3H), 2.19 (s, 3H), 2.00 (s, 3H), 1.58-1.30 (m, 8H), 0.73 (t, J = 7.2 Hz, 3H). |
| P-34 | 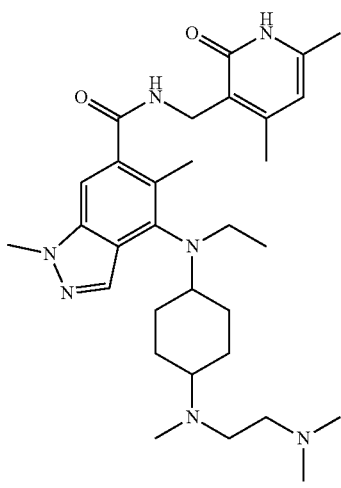 | ¹H NMR (400 MHz, DMSO) δ 11.49 (s, 1H), 8.14 (t, J = 4.0 Hz, 1H), 8.06 (s, 1H), 7.31 (s, 1H), 5.88 (s, 1H), 4.30 (d, J = 4.0 Hz, 2H), 3.99 (s, 3H), 3.32-3.22 (m, 2H), 2.98-2.96 (m, 1H), 2.72-2.70 (m, 4H), 2.59-2.58 (m, 1H), 2.42 (s, 6H), 2.36 (s, 3H), 2.30 (s, 3H), 2.23 (s, 3H), 2.11 (s, 3H), 1.99-1.96 (m, 1H), 1.75-1.70 (m, 3H), 1.30-1.29 (m, 4H), 0.77 (t, J = 8.0 Hz, 3H). |

| Compound No. | Structure | ¹HNMR |
|---|---|---|
| P-36 | 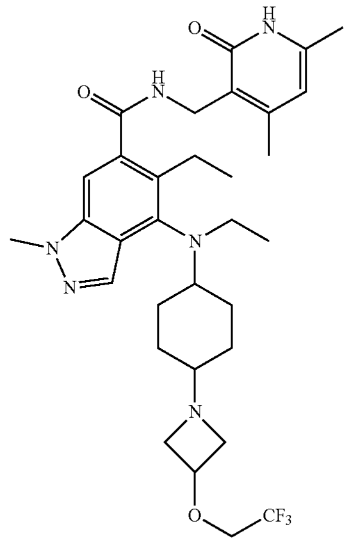 | ¹H NMR (400 MHz, DMSO) δ 11.44 (s, 1H), 8.11 (t, J = 5.2 Hz, 1H), 8.02 (s, 1H), 7.26 (s, 1H), 5.83 (s, 1H), 4.25 (d, J = 5.2 Hz, 2H), 4.11-4.08 (m, 1H), 3.98-3.91 (m, 5H), 3.38-3.35 (m, 4H), 3.15-3.04 (m, 1H), 2.93-2.82 (m, 3H), 2.73-2.69 (m, 2H), 2.19 (s, 3H), 2.06 (s, 3H), 1.93-1.78 (m, 2H), 1.62-1.56 (m, 2H), 1.33-1.19 (m, 2H), 0.91 (t, J = 7.2 Hz, 3H), 0.84-0.71 (m, 5H). |
| P-37 | 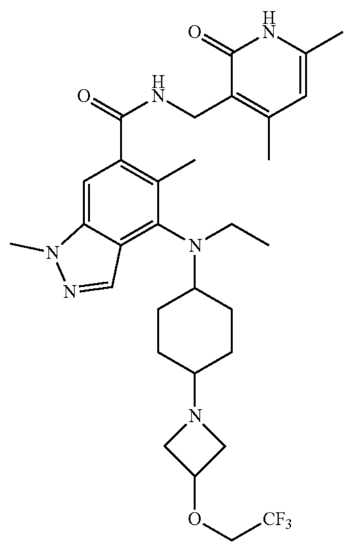 | ¹H NMR (400 MHz, DMSO) δ 11.44 (s, 1H), 8.09 (t, J = 4.8 Hz, 1H), 8.00 (s, 1H), 7.24 (s, 1H), 5.82 (s, 1H), 4.26 (d, J = 5.2 Hz, 2H), 4.11-4.08 (m, 1H), 3.98-3.91 (m, 5H), 3.37-3.34 (m, 3H), 3.23-3.07 (m, 2H), 2.92-2.86 (m, 1H), 2.92-2.69 (m, 2H), 2.21 (s, 3H), 2.18 (s, 3H), 2.06 (s, 3H), 1.89-1.77 (m, 2H), 1.64-1.57 (m, 2H), 1.25-1.13 (m, 2H), 0.79-0.69 (m, 5H). |
| P-39 | 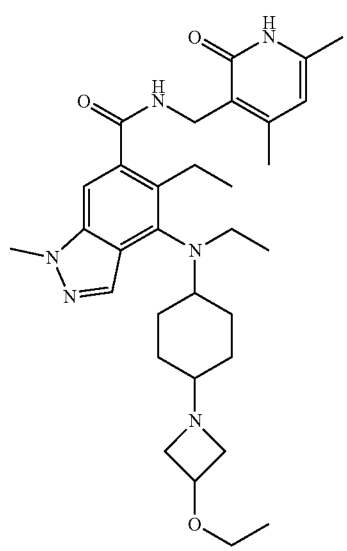 | ¹H NMR (500 MHz, DMSO) δ 11.46 (s, 1H), 8.13 (t, 1H), 8.05 (s, 1H), 7.29 (s, 1H), 5.86 (s, 1H), 4.29 (d, 2H), 3.97 (s, 3H), 3.93-3.87 (m, 1H), 3.39-3.27 (m, 5H), 3.20-3.12 (m, 1H), 2.98-2.87 (m, 4H), 2.67-2.64 (m, 2H), 2.22 (s, 3H), 2.10 (s, 3H), 1.94-1.22 (m, 6H), 1.05 (t, 3H), 0.95 (t, 3H), 0.85-0.74 (m, 5H). |

-continued

| Compound No. | Structure | ¹HNMR |
|---|---|---|
| P-40 | 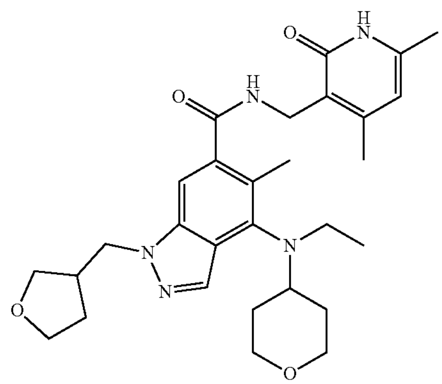 [SMILES: CCN(c1c(C)c(C(=O)NCc2c(C)cc(C)[nH]c2=O)cc2c1cnn2CC1CCOC1)C1CCOCC1] | ¹H NMR (400 MHz, DMSO) δ 11.45 (s, 1H), 8.15 (t, J = 5.2 Hz, 1H), 8.09 (s, 1H), 7.35 (s, 1H), 5.83 (s, 1H), 4.31-4.26 (m, 4H), 3.77-3.72 (m, 3H), 3.59-3.56 (m, 2H), 3.46-3.44 (m, 1H), 3.28-3.12 (m, 4H), 2.76-2.73 (m, 1H), 2.24 (s, 3H), 2.19 (s, 3H), 2.07 (s, 3H), 1.85-1.81 (m, 2H), 1.63-1.57 (m, 2H), 1.46-1.22 (m, 3H), 0.74 (t, J = 7.2 Hz, 3H). |
| P-41 | 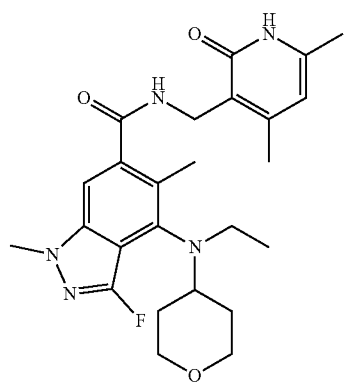 | ¹H NMR (400 MHz, DMSO) δ 11.50 (s, 1H), 8.25 (t, J = 4.0 Hz, 1H), 7.34 (s, 1H), 5.87 (s, 1H), 4.30 (d, J = 8.0 Hz, 2H), 3.87-3.86 (m, 4H), 3.71-3.68 (m, 1H), 3.31-3.20 (m, 5H), 3.13-3.12 (m, 1H), 2.28 (s, 3H), 2.22 (s, 3H), 2.11 (s, 3H), 1.98-1.95 (m, 1H), 1.50-1.49 (m, 1H), 1.22-1.20 (m, 2H), 0.77 (t, J = 8.0 Hz, 3H). |
| P-42 | 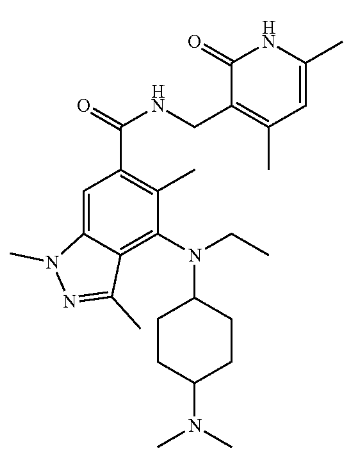 | ¹H NMR (500 MHz, DMSO) δ 11.57 (s, 1H), 9.29 (s, 1H), 8.21 (s, 1H), 7.27 (s, 1H), 5.91 (s, 1H), 4.30 (d, J = 4.7 Hz. 2H), 3.88 (s, 3H), 3.16 (m. 3H), 2.67 (d, J = 4.6 Hz, 6H), 2.56 (s, 3H), 2.23 (s, 3H), 2.20 (s, 3H), 2.12 (s, 3H), 1.90 (m, 12.9 Hz, 3H), 1.67 (m, 1H), 1.52 -1.36 (m, 3H), 1.26 (m, 1H), 1.07 (m, 1H), 0.83 (t, J = 7.0 Hz, 3H). |

| Compound No. | Structure | $^1$HNMR |
|---|---|---|
| P-43 | 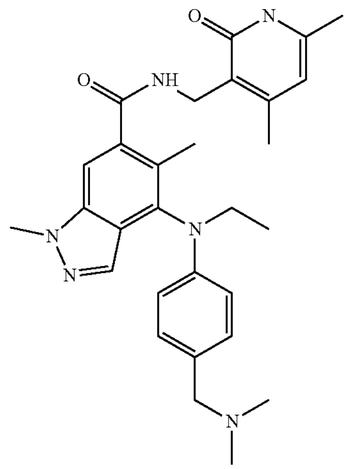 | $^1$H NMR (400 MHz, MeOD) δ 7.57 (s, 1H), 7.55 (s, 1H), 7.17 (d, J = 4.8 Hz, 2H), 6.55 (d, J = 4.8 Hz, 2H), 6.11 (s, 1H), 4.50 (s, 2H), 4.04 (m, 5H), 3.85-3.72 (m, 2H), 2.72 (s, 6H), 2.39 (s, 3H), 2.23 (s, 3H), 2.17 (s, 3H), 1.20 (t, J = 7.2 Hz, 3H). |

Bioassay

Test Example 1 In Vitro Methyltransferase Activity Assay

Recombinant PRC2 (EZH2-Y641F) was purchased from Active motif, S-adenosyl-methionine (SAM) and Poly-L-lysine (PLL) were purchased from Sigma-Aldrich, and H3(1-50)K27me1 peptide was purchased from Cisbio. LANCEUltrasystem (Perkinelmer) was used for detection system. In the enzyme activity test, compounds to be tested were diluted by 8 gradient points in a ratio of 1:3, and added into each well in a reaction plate, and 100 ng recombinase was added, followed by a buffer [20 mM Tris pH8.5, 2 mM MgCl2, 0.01% Tween-20, 1 mM TCEP] containing 2.5 μM SAM/250 nM H3 (1-50)K27me1 premixtures. Enzymatic reaction thus began at room temperature. After reacted for 3 hours, a detection solution premixed with PLL, detection antibody and Ulight was added, and reacted for 1 hour at room temperature. The fluorescence value was then read on a Tecan infinite pro. IC50 was calculated by fitting in a four-factor model in the XLfit software. The results are shown in Table 1:

TABLE 1

Inhibitory Activity of Compounds against EZH2 Y641F

| compound | EZH2 Y641F IC$_{50}$(μM) | compound | EZH2 Y641F IC$_{50}$(μM) | compound | EZH2 Y641F IC$_{50}$(μM) |
|---|---|---|---|---|---|
| P-1 | 0.025 | P-2 | 0.024 | P-3 | 0.154 |
| P-4 | 0.502 | P-7 | 0.012 | P-8 | 0.053 |
| P-9 | 0.009 | P-10 | 0.061 | P-11 | 0.013 |
| P-12 | 0.117 | P-13 | 0.023 | P-14 | 0.005 |
| P-15 | 0.007 | P-16 | 0.008 | P-17 | 0.008 |
| P-18 | 0.012 | P-19 | 0.045 | P-20 | 0.018 |
| P-21 | 0.014 | P-22 | 0.005 | P-23 | 0.005 |
| P-24 | 0.009 | P-25 | 0.046 | P-26 | 0.008 |
| P-27 | 1.750 | P-28 | 0.402 | P-29 | 0.034 |
| P-30 | 0.046 | P-31 | 0.015 | P-32 | 0.012 |
| P-33 | 0.037 | P-34 | 0.026 | P-36 | 0.013 |
| P-37 | 0.012 | P-38 | 0.038 | P-39 | 0.007 |
| P-41 | 0.425 | P-42 | 0.253 | P-43 | 0.033 |
| P-44 | 0.060 | P-45 | 0.027 | P-46 | 0.053 |
| P-47 | 0.007 | P-48 | 0.049 | P-50 | 0.148 |

TABLE 1-continued

Inhibitory Activity of Compounds against EZH2 Y641F

| compound | EZH2 Y641F IC$_{50}$(μM) | compound | EZH2 Y641F IC$_{50}$(μM) | compound | EZH2 Y641F IC$_{50}$(μM) |
|---|---|---|---|---|---|
| D1 | >10 | D2 | 4.820 | D3 | >10 |
| D4 | >10 | | | | |

Test Example 2 Cell Proliferation Assay

The used cell lines Pfeiffer (CRL-2632), suDHL-6 (CRL-2959) and suDHL-10 (CRL-2963) were obtained from American Type Culture Collection (ATCC). All cell lines were cultured in RPMI-1640 medium (Gibco) containing 10% fetal bovine serum (Gibco). The cultured cells were harvested by centrifugation and the cell density was determined using a CounterStar cell counter. Appropriate number of cells were plated in a 96-well culture plate and incubated overnight. Compounds to be tested were diluted by 8 gradient points in a ratio of 1:3 and added into corresponding wells. After continuing to culture for 6 days, the number of viable cells was measured with Cell counting kit-8, and the absorbance value was read on Tecan infinite pro. The IC50 was calculated by fitting in a four-parameter model in the XLfit software. The results are shown in Table 2:

TABLE 2

Inhibitory Activity of Compounds Against Pfeiffer cells

| compound | Pfeiffer IC$_{50}$(μM) | compound | Pfeiffer IC$_{50}$(μM) | compound | Pfeiffer IC$_{50}$(μM) |
|---|---|---|---|---|---|
| P-1 | 0.093 | P-5 | 0.071 | P-9 | 0.032 |
| P-7 | 0.158 | P-11 | 0.292 | P-15 | 0.076 |
| P-10 | 0.141 | P-14 | 0.212 | P-18 | 0.007 |
| P-16 | 0.007 | P-17 | 0.036 | P-21 | 0.032 |
| P-19 | 0.076 | P-20 | 0.031 | P-22 | 0.066 |
| P-23 | 0.025 | P-24 | 0.169 | P-25 | 0.278 |
| P-26 | 0.048 | P-27 | >10 | P-28 | 0.702 |
| P-29 | 0.191 | P-30 | 0.201 | P-31 | 0.130 |
| P-32 | 0.059 | P-34 | 0.196 | P-35 | 0.032 |
| P-36 | 0.003 | P-37 | 0.297 | P-39 | 0.005 |

TABLE 2-continued

Inhibitory Activity of Compounds Against Pfeiffer cells

| compound | Pfeiffer IC$_{50}$(μM) | compound | Pfeiffer IC$_{50}$(μM) | compound | Pfeiffer IC$_{50}$(μM) |
|---|---|---|---|---|---|
| P-40 | 0.268 | P-41 | 1.997 | P-43 | 0.123 |
| P-44 | 0.300 | P-47 | 0.178 | P-48 | 0.305 |
| D1 | >10 | D2 | >3 | D3 | >3 |
| D4 | >3 | | | | |

It can be seen from Table 1 and Table 2 that the representative compounds of the present disclosure has high inhibitory activity against EZH2 enzymes and cells. It was found that the types of $R_0$ and $R_1$ in the compound of formula (I) have a great influence on the enzyme inhibitory activity of the compound. When $R_0$ is hydrogen and $R_1$ is alkyl, it has good inhibitory activity against the enzyme, and when $R_0$ is alkyl and $R_1$ is hydrogen or other substituents, the inhibitory activity against the enzyme is greatly reduced. In addition, the types of five-membered benzoheterocyclic ring have a great influence on the inhibitory activity of the enzyme, and when the formula B-1 in the compound structure is replaced with formula B-2, formula B-3 or formula B-4 (e.g., P-3, P-4 or P-50 and P-7), the inhibitory activity against the enzyme is significantly reduced. In addition, when the formula B-1 is adopted in the compound structure, the presence or absence of substituent at 3 position as well as the change of the substituent at 5 position of the benzene ring all have a great influence on the inhibitory activity of the enzyme. When the hydrogen at 3-position is substituted by methyl or fluorine (such as P-42 and P-13/14, P-41 and P-7), the enzyme inhibitory activity is greatly reduced, and when the methyl at 5-position of the benzene ring is replaced by other substituents such as cyano, cyclopropyl, the inhibitory activity against the enzyme is significantly reduced.

All publications mentioned herein are incorporated by reference as if each individual document is cited as a reference, as in the present application. It should also be understood that, after reading the above teachings of the present disclosure, those skilled in the art can make various changes or modifications, equivalents of which fall in the scope of claims as defined in the appended claims.

The invention claimed is:

1. A compound of formula (I), or a pharmaceutically acceptable salt, solvate, or stereoisomer thereof:

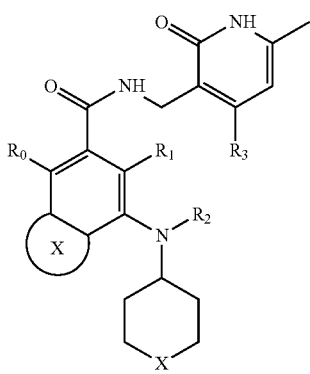

(I)

wherein, $R_0$ is hydrogen;

$R_1$ is CN, halogen, $C_{1-8}$ alkyl, halogenated $C_{1-8}$ alkyl, $C_{1-8}$ alkoxy, $C_{3-8}$ cycloalkyl or $C_{3-8}$ cycloalkoxy;

$R_2$ is hydrogen, $C_{1-8}$ alkyl, halogenated $C_{1-8}$ alkyl or $C_{3-8}$ cycloalkyl;

$R_3$ is hydrogen, halogen, hydroxy, CN, $C_{1-8}$ alkyl, halogenated $C_{1-8}$ alkyl, $C_{3-8}$ cycloalkyl, $C_{1-8}$ alkoxy, halogenated $C_{1-8}$ alkoxy, $C_{3-8}$ cycloalkoxy, $C_{6-10}$ aryl, —C(O)$C_{1-8}$ alkyl, —C(O)O$C_{1-8}$ alkyl, —CONR$_a$R$_b$ or NR$_a$R$_b$;

X is NR$_4$, CR$_5$R$_6$, O, S or S(O)$_2$;

$R_4$ is hydrogen or —(CH$_2$)$_m$-L$_2$; wherein L$_2$ is CN, $C_{1-8}$ alkyl, NR$_{a3}$R$_{b3}$, $C_{1-8}$ alkoxy, halogenated $C_{1-8}$ alkyl, C(O)$C_{1-8}$ alkyl, C(O)O$C_{1-8}$ alkyl, CONR$_{a1}$R$_{b1}$, $C_{3-8}$ cycloalkyl, —SO$_2$C$_{1-8}$ alkyl, —C(O)CH$_2$CN, —C(O)CH$_2$OH, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle; m is 0, 1 or 2; the alkyl, alkoxy, cycloalkyl, 4 to 6 membered saturated heteromonocycle, 5 to 6 membered monocylic heteroaryl ring, 8 to 10 membered bicyclic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, NR$_{a3}$R$_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran;

$R_5$ is hydrogen and $R_6$ is —(CH$_2$)$_p$-L$_3$; L$_3$ is CN, $C_{1-8}$ alkyl, $C_{1-8}$ alkoxy, halogenated $C_{1-8}$ alkyl, $C_{3-8}$ cycloalkyl, NR$_{a3}$R$_{b3}$, 4 to 6 membered saturated heteromonocycle, 5 to 6 membered monocylic heteroaryl ring, spiro, spiroheterocycle, bridged ring or bridged heterocycle; p is 0, 1 or 2; the alkyl, alkoxy, cycloalkyl, 4 to 6 membered saturated heteromonocycle, 5 to 6 membered monocylic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, NR$_{a3}$R$_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran;

$R_a$, $R_b$, $R_{a1}$, $R_{b1}$, are each independently hydrogen, $C_{1-8}$ alkyl, or C(O)$C_{1-8}$ alkyl;

ring A is a structure represented by formula (A-1), formula (A-2), formula (A-3) or formula (A-4):

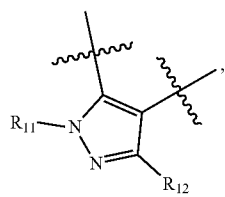

(A-1)

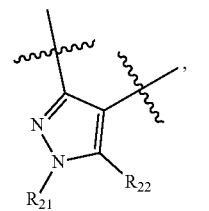

(A-2)

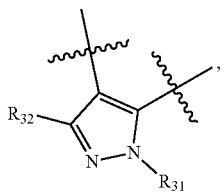

(A-3)

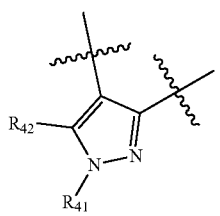

(A-4)

wherein, $R_{11}$, $R_{21}$, $R_{31}$, $R_{41}$, are each independently hydrogen or —$(CH_2)_n$-$L_1$; wherein $L_1$ is CN, $NR_{a3}R_{b3}$, $C_{1-8}$ alkyl, $C_{1-8}$ alkoxy, halogenated $C_{1-8}$ alkyl, $C_{3-8}$ cycloalkyl, 4 to 6 membered saturated heteromonocycle, 5 to 6 membered monocylic heteroaryl ring, spiro, spiroheterocycle, bridged ring or bridged heterocycle; n is 0, 1 or 2; the alkyl, alkoxy, cycloalkyl, 4 to 6 membered saturated heteromonocycle, 5 to 6 membered monocylic heteroaryl ring, spiro, spiroheterocycle, bridged ring or bridged heterocycle are unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran;

$R_{12}$, $R_{22}$, $R_{32}$, $R_{42}$ are each independently hydrogen, halogen, $C_{1-8}$ alkyl, halogenated $C_{1-8}$ alkyl or $C_{3-8}$ cycloalkyl;

the alkyl, or cycloalkyl are unsubstituted or substituted by 1, 2 or 3 substituents selected from the group consisting of CN, acetyl, hydroxy, hydroxymethyl, hydroxyethyl, carboxyl, —C(O)O$C_{1-6}$ alkyl, $C_{1-8}$ alkyl, $C_{1-8}$ alkoxy, halogenated $C_{1-8}$ alkyl, $C_{3-8}$ cycloalkyl, halogenated $C_{1-8}$ alkoxy, $NR_{a3}R_{b3}$, 4 to 6 membered saturated heteromonocycle, 5 to 6 membered monocylic heteroaryl ring, 8 to 10 membered bicyclic heteroaryl ring, spiro, spiroheterocycle, bridged ring and bridged heterocycle;

$R_{a3}$, $R_{b3}$ are each independently hydrogen, $C_{1-8}$ alkyl or $C_{1-8}$ alkyl substituted by $C_{1-8}$ alkoxy.

2. The compound of claim 1 or the pharmaceutically acceptable salt, solvate, or stereoisomer thereof, wherein $R_1$ is $C_{1-3}$ alkyl.

3. The compound of claim 1 or the pharmaceutically acceptable salt, solvate, or stereoisomer thereof, wherein $R_2$ is hydrogen, $C_{1-3}$ alkyl or halogenated $C_{1-3}$ alkyl.

4. The compound of claim 1 or the pharmaceutically acceptable salt, solvate, or stereoisomer thereof, wherein $R_3$ is hydrogen, halogen, $C_{1-3}$ alkyl or $C_{1-3}$ alkoxy.

5. The compound of claim 1 or the pharmaceutically acceptable salt, solvate, or stereoisomer thereof, wherein $R_0$ is hydrogen and $R_1$ is $C_{1-3}$ alkyl.

6. The compound of claim 1 or the pharmaceutically acceptable salt, solvate, or stereoisomer thereof, wherein $R_{11}$, $R_{21}$, $R_{31}$, $R_{41}$ are each independently hydrogen or —$(CH_2)_n$-$L_1$; wherein $L_1$ is CN, $NR_{a3}R_{b3}$, $C_{1-8}$ alkyl, $C_{1-8}$ alkoxy, halogenated $C_{1-8}$ alkyl, $C_{3-8}$ cycloalkyl, or 4 to 6 membered saturated heteromonocycle; n is 0, 1 or 2;

the alkyl, alkoxy, cycloalkyl, or 4 to 6 membered saturated heteromonocycle, are unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as defined in claim 1.

7. The compound of claim 1 or the pharmaceutically acceptable salt, solvate, or stereoisomer thereof, wherein $R_{12}$, $R_{22}$, $R_{32}$, $R_{42}$ are each independently hydrogen, methyl, ethyl, n-propyl, or isopropyl.

8. The compound of claim 1 or the pharmaceutically acceptable salt, solvate, or stereoisomer thereof, wherein $R_4$ is hydrogen or —$(CH_2)_m$-$L_2$; wherein $L_2$ is halogenated $C_{1-8}$ alkyl or 4 to 6 membered saturated heteromonocycle; m is 0, 1 or 2;

the 4 to 6 membered saturated heteromonocycle is unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as defined in claim 1.

9. The compound of claim 1 or the pharmaceutically acceptable salt, solvate, or stereoisomer thereof, wherein $R_5$ is hydrogen and $R_6$ is —$(CH_2)_p$-$L_3$; $L_3$ is $NR_{a3}R_{b3}$ or 4 to 6 membered saturated heteromonocycle; p is 0, 1 or 2;

the 4 to 6 membered saturated heteromonocycle is unsubstituted or substituted by one substituent selected from the group consisting of acetyl, hydroxy, hydroxymethyl, hydroxyethyl, carboxyl, —C(O)O$C_{1-6}$ alkyl, $C_{1-3}$ alkyl, $C_{1-3}$ alkoxy, halogenated $C_{1-3}$ alkyl, $C_{3-6}$ cycloalkyl, $NR_{a3}R_{b3}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide and tetrahydropyran; and $R_{a3}$, $R_{b3}$ are as defined in claim 1.

10. The compound of claim 1 or the pharmaceutically acceptable salt, solvate, or stereoisomer thereof, wherein, $R_0$ is hydrogen,

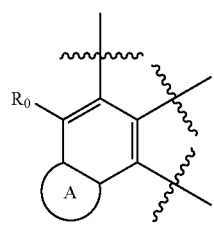
is a structure represented by formula (B-1):
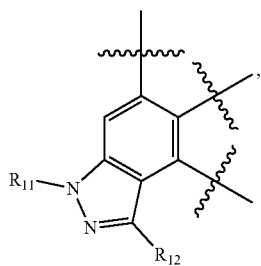
(B-1)
and
wherein $R_{11}$, $R_{12}$ are as defined in claim 1.
11. The compound of claim 1, or the pharmaceutically acceptable salt, solvate, or stereoisomer thereof, wherein the compound is selected from:
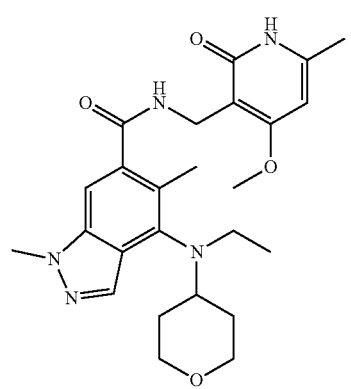
,
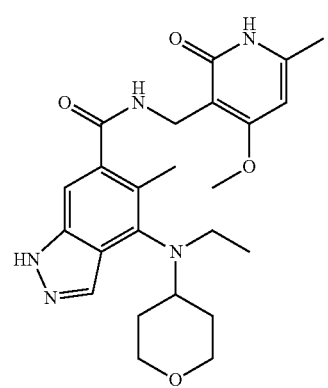
,
-continued
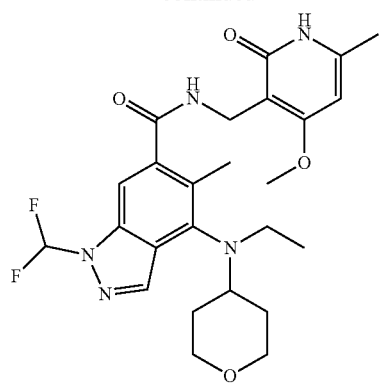
,
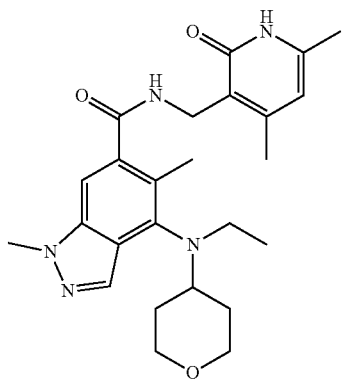
,
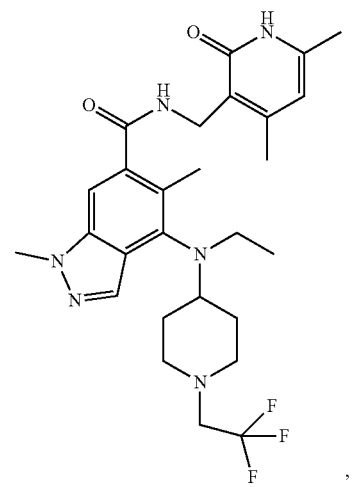
, 121
-continued
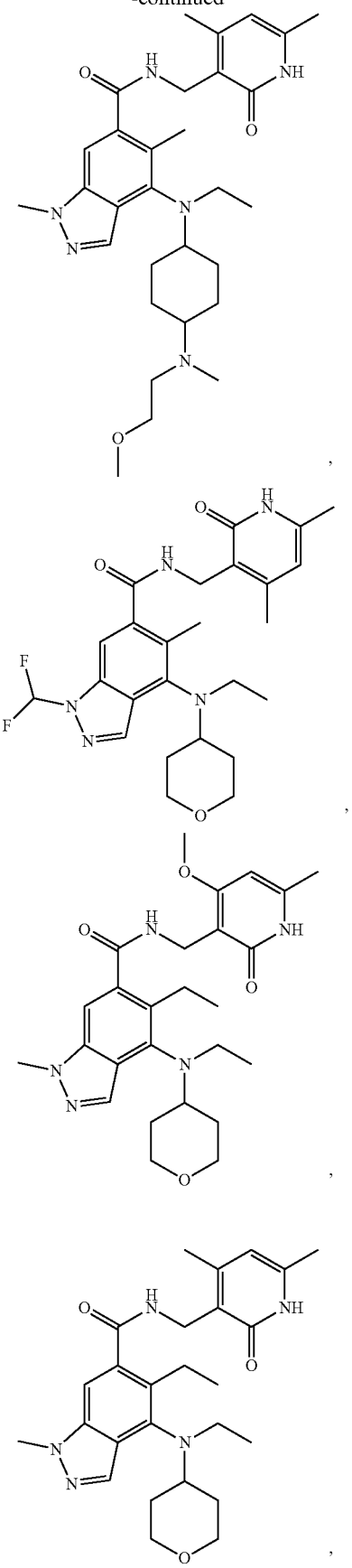
122
-continued
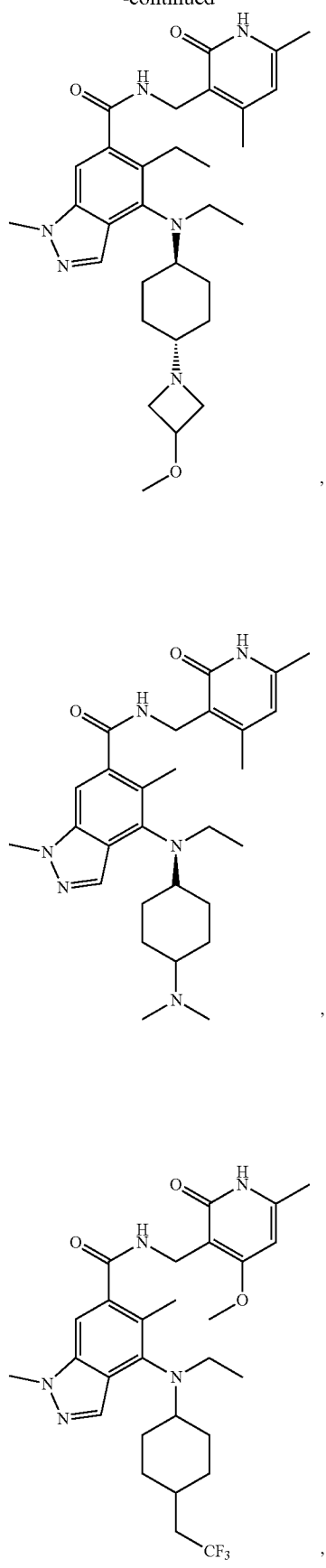

123
-continued
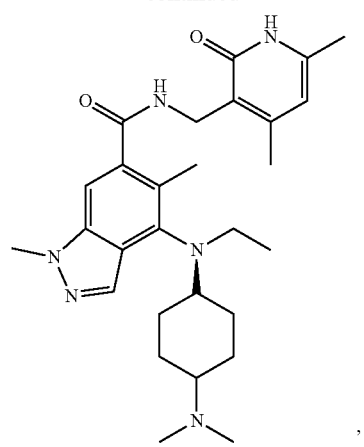
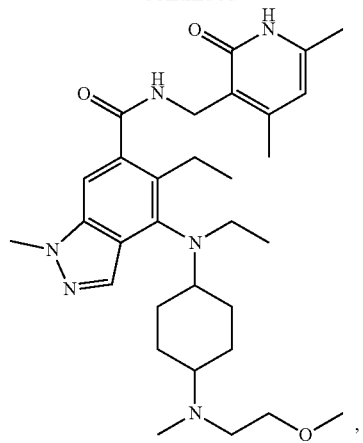
124
-continued
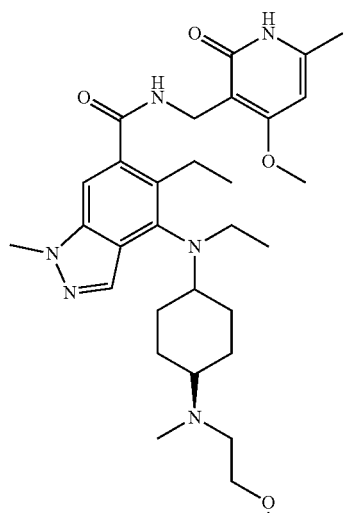
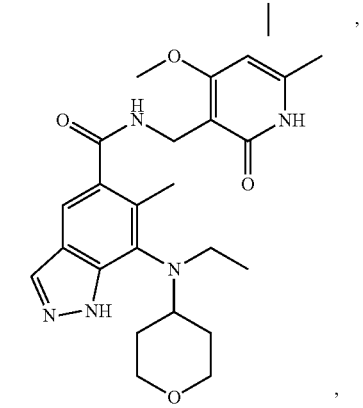
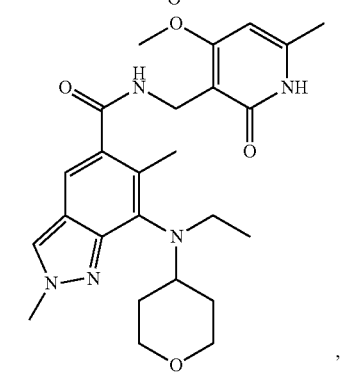

125

-continued

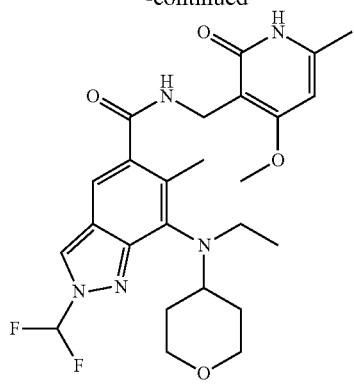

or

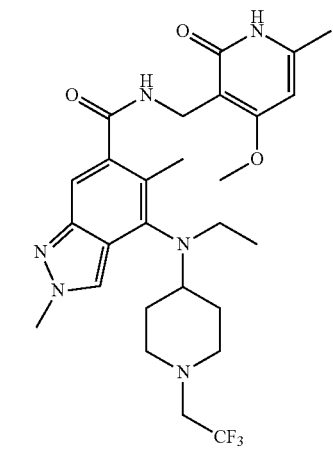

126

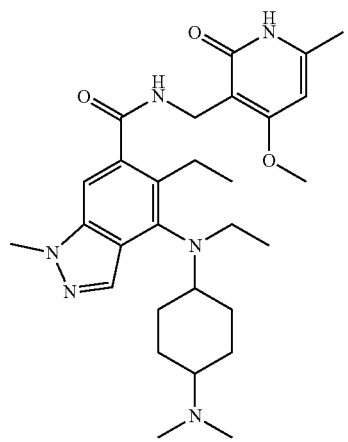

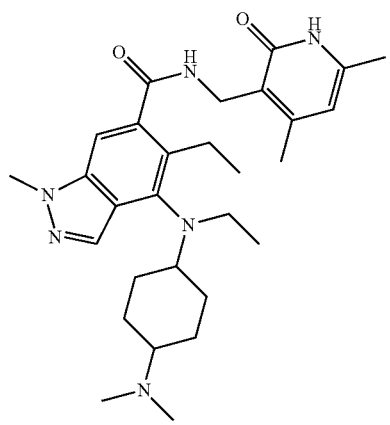

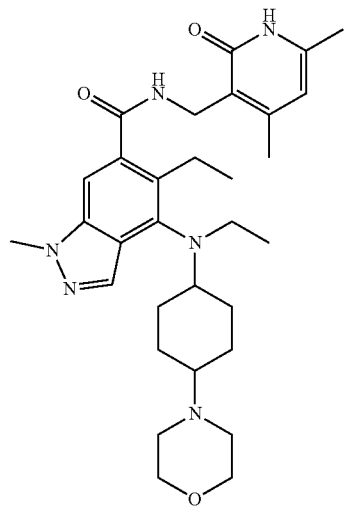

12. A pharmaceutical composition comprising the compound of claim 1, or the pharmaceutically acceptable salt, solvate, or stereoisomer thereof; and a pharmaceutically acceptable carrier.

13. A method of delaying the progression of or alleviating a disease or condition mediated by EZH2, comprising administering to a patient in need thereof a therapeutically effective amount of the compound of claim 1, or the pharmaceutically acceptable salt, solvate, or stereoisomer thereof, wherein the disease or condition mediated by EZH2 is cancer, the cancer is selected from the group consisting of thyroid cancer, cardiac sarcoma, lung cancer, gastrointestinal cancer, genitourinary tract tumor, liver cancer, mantle cell lymphoma, osteosarcoma, nervous system sarcoma, gynecological cancer, hematological system tumor, adrenal neuroblastoma, skin cancer, astrocytic tumor, breast cancer, colorectal cancer, endometrial cancer, head and neck cancer and oral cavity cancer.

14. A compound, or the pharmaceutically acceptable salt, solvate, or stereoisomer thereof, wherein the compound is selected from:

127
-continued
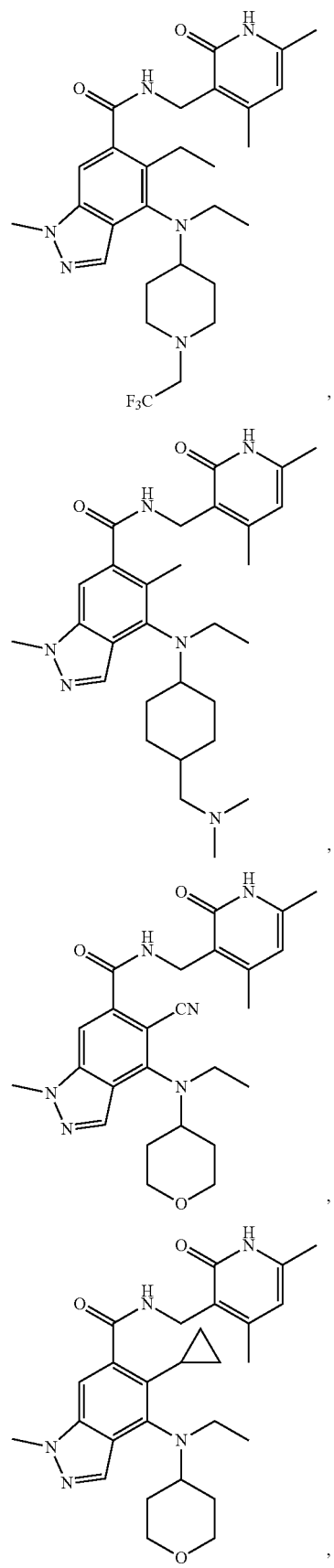
128
-continued
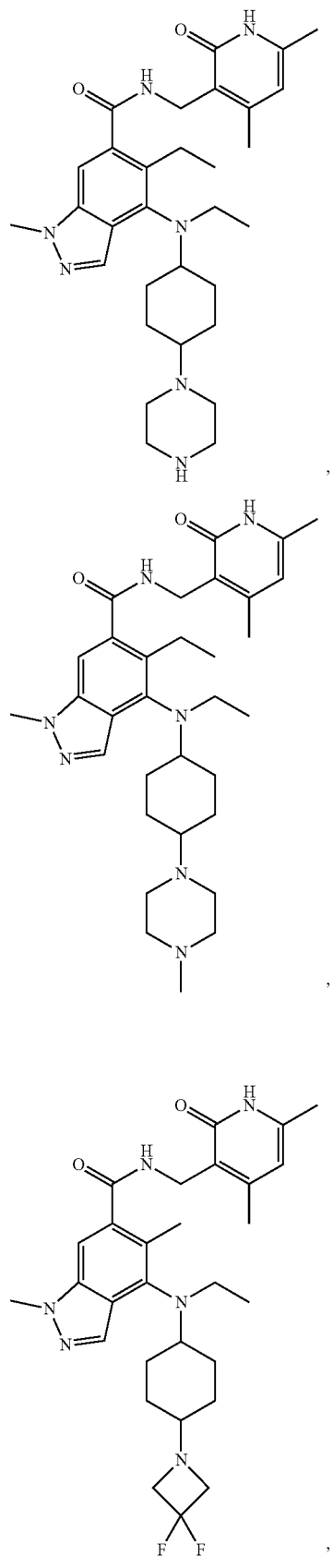

129
-continued
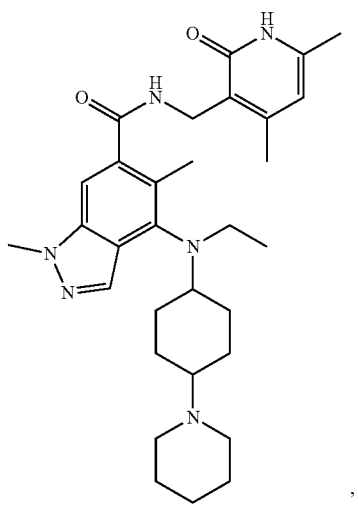
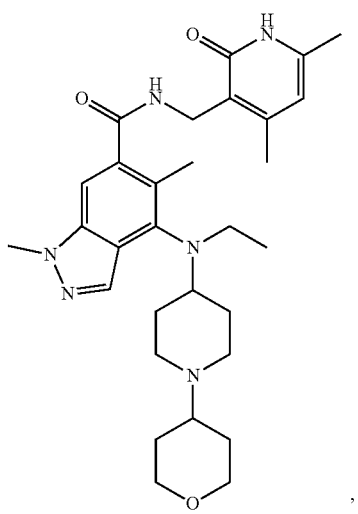
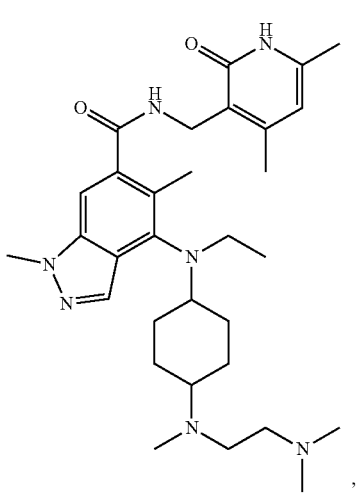
130
-continued
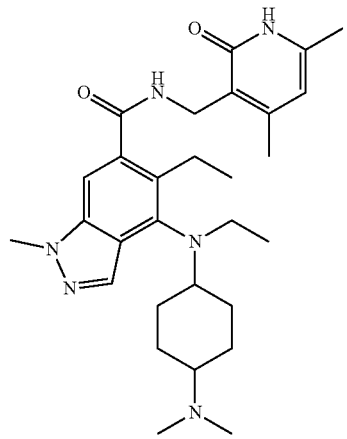
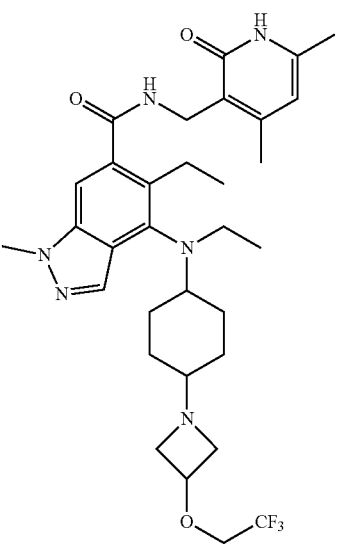
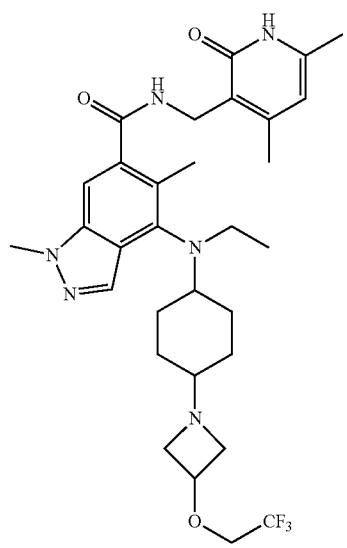

131
-continued
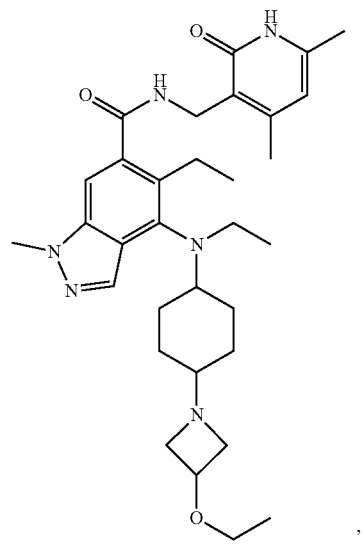
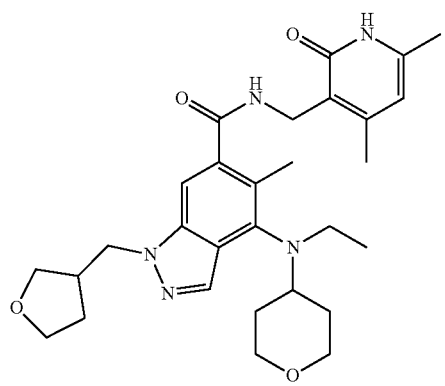
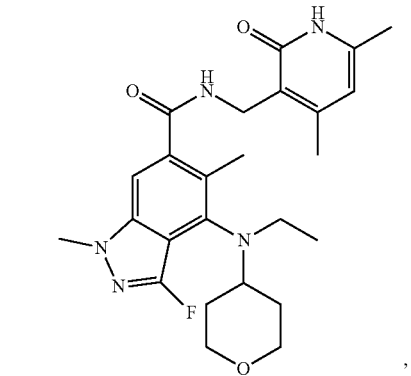
132
-continued
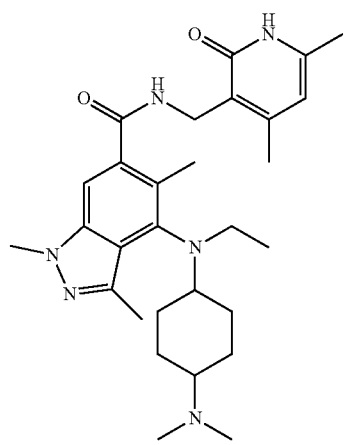
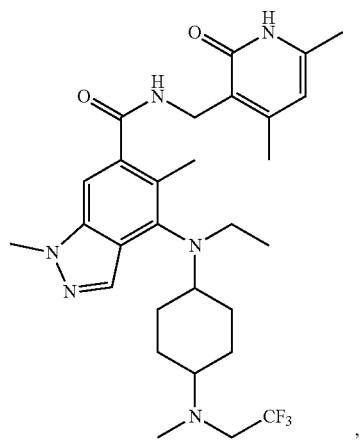
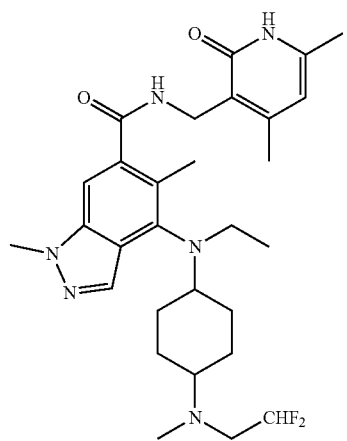

133
-continued
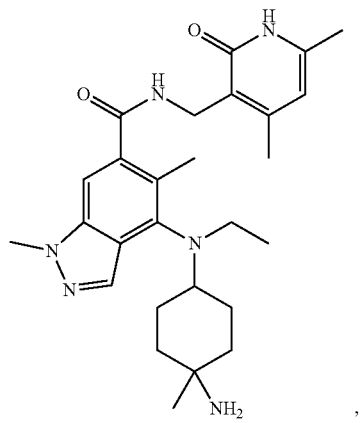
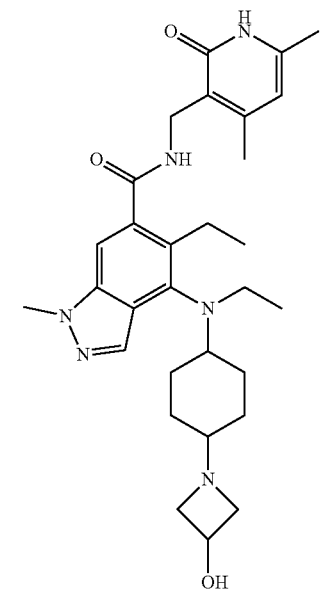
134
-continued
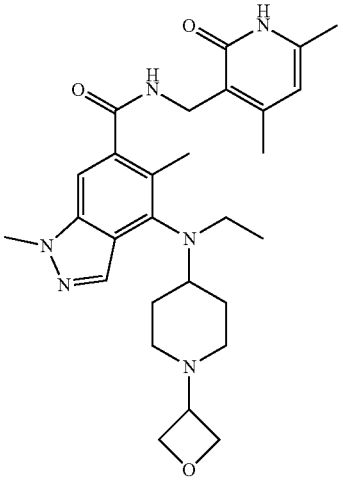
or
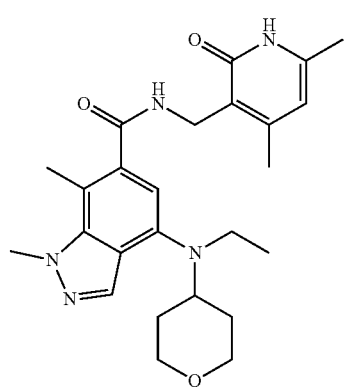
.
* * * * *